(12) United States Patent
Watanabe et al.

(10) Patent No.: US 8,436,172 B2
(45) Date of Patent: May 7, 2013

(54) MATERIAL SELECTING METHOD UPON PURIFYING IRIDIUM COMPLEX BY SUBLIMATION

(75) Inventors: Kousuke Watanabe, Kanagawa (JP); Keiju Tonosaki, Kanagawa (JP)

(73) Assignee: UDC Ireland Limited, Dublin (IE)

( * ) Notice: Subject to any disclaimer, the term of this patent is extended or adjusted under 35 U.S.C. 154(b) by 0 days.

(21) Appl. No.: 13/393,243

(22) PCT Filed: Aug. 27, 2010

(86) PCT No.: PCT/JP2010/065086
§ 371 (c)(1),
(2), (4) Date: Feb. 29, 2012

(87) PCT Pub. No.: WO2011/025064
PCT Pub. Date: Mar. 3, 2011

(65) Prior Publication Data
US 2012/0184743 A1    Jul. 19, 2012

(30) Foreign Application Priority Data

Aug. 31, 2009  (JP) ................................ 2009-201160
Sep. 28, 2009  (JP) ................................ 2009-223454

(51) Int. Cl.
*C07F 15/00*    (2006.01)
*H01L 51/50*    (2006.01)

(52) U.S. Cl.
USPC ............................. 546/10; 313/504; 428/690

(58) Field of Classification Search ............... 546/10; 313/504; 428/690
See application file for complete search history.

(56) References Cited

U.S. PATENT DOCUMENTS

| 6,583,583 | B1 | 6/2003 | Soeda et al. |
| 2001/0015617 | A1 | 8/2001 | Kawamura et al. |
| 2007/0278936 | A1 | 12/2007 | Herron et al. |
| 2008/0166472 | A1 | 7/2008 | MacKenzie et al. |
| 2008/0297033 | A1 | 12/2008 | Knowles et al. |

FOREIGN PATENT DOCUMENTS

| JP | 11-171801 A | 6/1999 |
| JP | 2004-59433 A | 2/2004 |
| JP | 3516671 B1 | 4/2004 |
| JP | 3525034 B2 | 5/2004 |
| JP | 2004-155728 A | 6/2004 |
| JP | 2004-161661 A | 6/2004 |
| JP | 2006-131561 A | 5/2006 |
| JP | 2008-303205 A | 12/2008 |
| JP | 2009108041 A | 5/2009 |
| WO | WO 2005/118606 A1 | 12/2005 |
| WO | WO 2008/109824 A2 | 9/2008 |
| WO | WO 2009/073245 A1 | 6/2009 |

OTHER PUBLICATIONS

Communication dated Nov. 17, 2009, issued by the Japanese Patent Office in corresponding Japanese Patent Application No. 2009-223454.
International Search Report (PCT/ISA/210), dated Oct. 19, 2010, issued in International Application No. PCT/JP2010/065086.
Written Opinion (PCT/ISA/237) dated Oct. 19, 2010, issued in International Application No. PCT/JP2010/065086.

*Primary Examiner* — Charanjit Aulakh
(74) *Attorney, Agent, or Firm* — Morgan, Lewis & Bockius LLP

(57) ABSTRACT

Provided is a material selecting method used upon purifying an iridium complex by sublimation which includes: selecting an iridium complex having a specific structure and having a rate of weight loss of 45% or greater when heated to 500° C. at a heating rate of 2° C./min under the degree of vacuum of from $1 \times 10^{-3}$ Pa to $1 \times 10^{-1}$ Pa; and carrying out sublimation purification.

5 Claims, 30 Drawing Sheets

MATERIAL SELECTING METHOD UPON PURIFYING IRIDIUM COMPLEX BY SUBLIMATION

TECHNICAL FIELD

The present invention relates to a material selecting method upon sublimation purification of an iridium complex, more specifically, to a material selecting method upon sublimation purification of an iridium complex to be used for an organic electroluminescence device (which may hereinafter be called "device" or "organic EL device").

BACKGROUND ART

Research and development are being vigorously made on organic electroluminescence devices because they can emit light with high brightness even by low voltage driving. In general, organic electroluminescence devices each has one or more organic layers including a light emitting layer and a pair of electrodes sandwiching them therebetween. For light emission, they utilize energy of an exciton generated as a result of recombination, in the light emitting layer, of electrons injected from a cathode and holes injected from an anode.

For the light emitting layer of organic electroluminescence devices, fluorescent materials or phosphorescent materials are used and as these light emitting materials, metal complexes can be used. For example, U.S. Patent Application Publication No. 2008/297033, WO09/073,245, and WO08/109,824 describe iridium complexes containing a condensed-ring azole ligand.

It is the common practice to employ sublimation purification for the purification of materials to be used for organic electroluminescence devices. Various techniques have been proposed for improving the efficiency in sublimation purification. For example, Japanese Patent No. 3516671 describes tris(8-oxyquinolinolato)aluminum characterized by that it has an exotherm of 2 J/g at a temperature between 350 to 400° C. in differential scanning calorimetry under nitrogen flow and has an endotherm of from 70 to 120 J/g at a temperature between 400 to 450° C. with a temperature near 420° C. as an endothermic peak. Japanese Patent No. 3525034 describes a technique of performing sublimation purification of an organic compound at a temperature lower by at least 30° C. than the thermal decomposition temperature thereof. Japanese Patent Laid-Open No. 11/171,801 describes a sublimation purification method of an organic compound including stirring or vibrating the organic compound.

SUMMARY OF INVENTION

Techniques as described above have been proposed, but they have such a problem that when they are employed, the sublimation purification yield of an iridium complex having a condensed-ring structure is markedly low.

An object of the invention is to provide a selecting method of an iridium complex having a condensed-ring structure and providing a high sublimation purification yield.

Finding during sublimation purification of various iridium complexes that even if compounds are the same, the sublimation purification yield varies greatly, depending on their synthesis process, the present inventors have carried out an intensive investigation with a view to improving the sublimation purification yield. As a result, it has been found that iridium complexes showing a specific thermal decomposition behavior are excellent in sublimation purification yield, leading to the completion of the invention.

The invention has been achieved by using the following means.

(1) A material selecting method comprising:
selecting an iridium complex represented by the following formula (1) and having a rate of weight loss of 45% or greater when the iridium complex is heated to 500° C. at 2° C./min under a degree of vacuum of from $1 \times 10^{-3}$ Pa to $1 \times 10^{-1}$ Pa; and
carrying out a sublimation purification of the iridium complex:

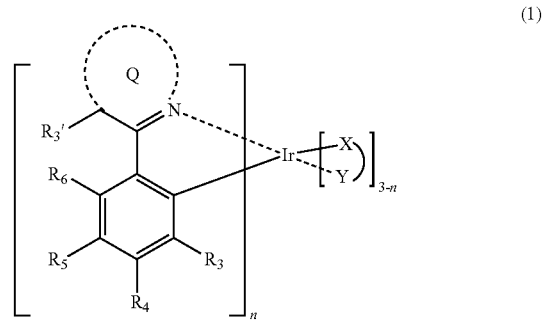

(1)

wherein
each of $R_3$, $R_4$, $R_5$, $R_6$, and $R_3'$ independently represents a hydrogen atom or a substituent;
$R_3'$ and $R_6$ may be linked to form a ring via a linking group selected from $-CR_2-CR_2-$, $-CR=CR-$, $-CR_2-$, $-O-$, $-O-CR_2-$, $-NR-CR_2-$, and $-N=CR-$, wherein each of Rs independently represents a hydrogen atom, an alkyl group, an alkenyl group, an alkynyl group, a heteroalkyl group, an aryl group or a heteroaryl group and may further have a substituent, and a plurality of the Rs may be coupled to each other to form a five- or six-membered ring;
$R_3$ and $R_4$ may be coupled to each other to form a condensed four- to seven-membered ring and the condensed four- to seven-membered ring is a cycloalkane ring, cycloheteroalkane ring, aromatic hydrocarbon ring, or heteroaromatic ring and may further have a substituent;
$R_4$ and $R_5$ may be coupled to each other to form a ring;
the ring Q represents an aromatic heterocycle or condensed aromatic heterocycle having at least one nitrogen atom coordinated to iridium, with the proviso that either one of the ring Q or a benzene ring coupled to the ring Q is condensed;
(X-Y) represents an ancillary ligand; and
n stands for an integer from 1 to 3.

(2) The material selecting method according to (1), wherein when the iridium complex is heated at 10° C./min under ordinary pressure, the iridium complex shows an endothermic change as a thermal change in a range of a rate of weight loss of from 1 to 5 mass %.

(3) The material selecting method according to (1) or (2), wherein the ring Q is condensed and at least one of $R_3$, $R_4$, $R_5$, and $R_6$ represents a methyl group or a phenyl group, with the proviso that when at least one of $R_3$, $R_4$, $R_5$, and $R_6$ represents a phenyl group, the phenyl group may further have a substituent or the phenyl group may be coupled to the ring Q via a linking group or a single bond.

(4) The material selecting method according to any one of (1) to (3), wherein the iridium complex is represented by the following formula (T-4):

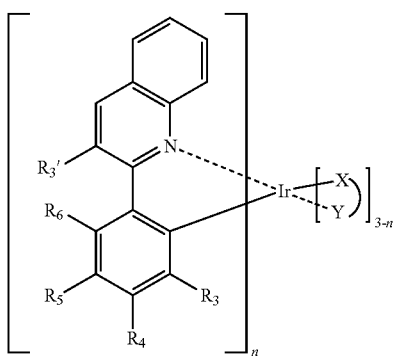

(T-4)

wherein $R_3'$ represents a hydrogen atom, an alkyl group, a heteroalkyl group, an aryl group, or a heteroaryl group and may further have a substituent Z;

each of $R_3$, $R_4$, $R_5$, and $R_6$ independently represents a hydrogen atom, an alkyl group, an alkenyl group, an alkynyl group, —CN, —CF$_3$, —C$_n$F$_{2n+1}$, a trifluorovinyl group, —CO$_2$R, —C(O)R, —NR$_2$, —NO$_2$, —OR, a halogen atom, an aryl group, or a heteroaryl group and may further have a substituent Z, wherein each of Rs independently represents a hydrogen atom, an alkyl group, an alkenyl group, an alkynyl group, a heteroalkyl group, an aryl group, or a heteroaryl group and may further have a substituent;

each of Zs independently represents a halogen atom, —R', —OR', —N(R')$_2$, —SR', —C(O)R', —C(O)OR', —C(O)N(R')$_2$—, —CN, —NO$_2$, —SO$_2$, —SOR', —SO$_2$R', or —SO$_3$R', each of R's independently represents a hydrogen atom, an alkyl group, a perhaloalkyl group, an alkenyl group, an alkynyl group, a heteroalkyl group, an aryl group, or a heteroaryl group;

$R_4$ and $R_5$ may be coupled to each other to form a ring;

(X-Y) represents an ancillary ligand; and n stands for an integer from 1 to 3.

(5) The material selecting method according to any one of (1) to (4), wherein the iridium complex is purified by column chromatography.

(6) A method of manufacturing an organic electroluminescence device, comprising using an iridium complex selected according to a material selecting method as described in any one of (1) to (5).

Advantageous Effects of Invention

Using a material selecting method of the invention makes it possible to improve the sublimation purification yield of iridium complexes and thereby manufacture organic electroluminescence devices at a low cost.

DESCRIPTION OF EMBODIMENTS

Figure 1:
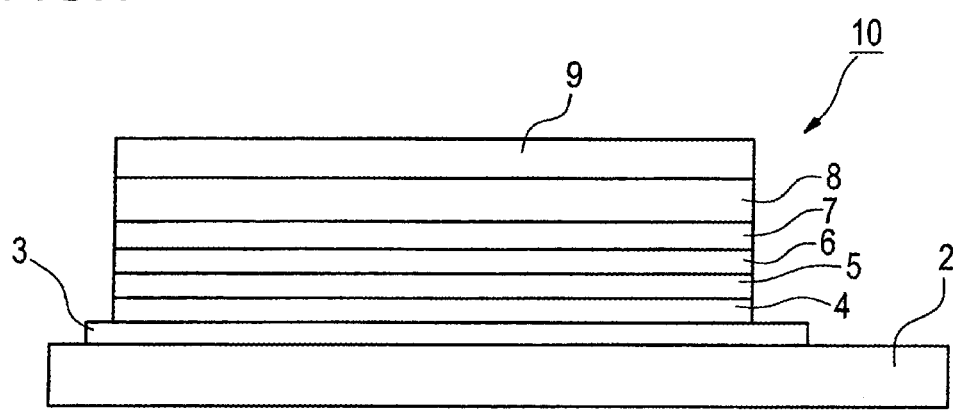
FIG. 1 is a schematic view illustrating an example (first exemplary embodiment) of a layer constitution of an organic EL device.
Figure 2:
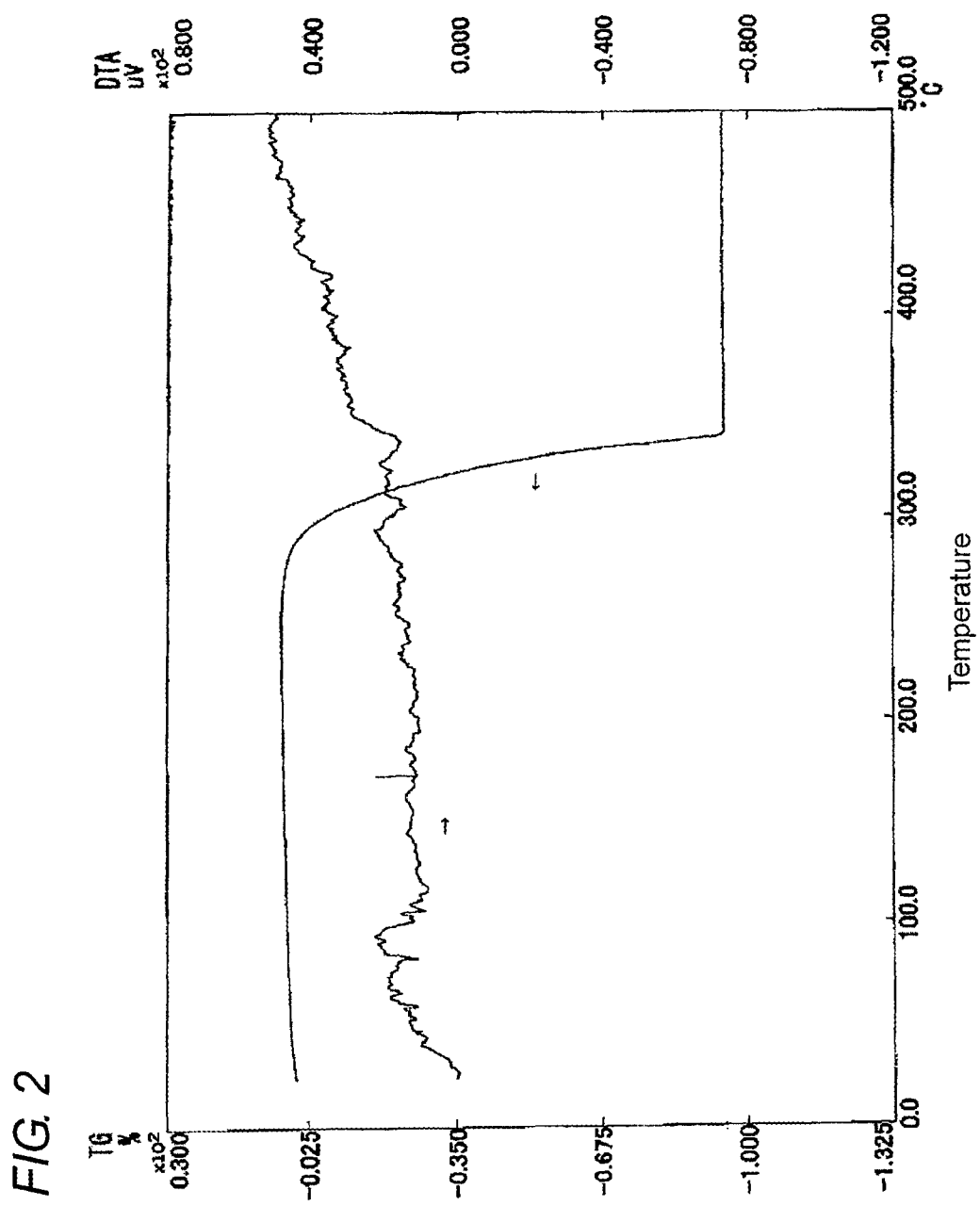
FIG. 2 shows a TG/DTA curve of Compound (1)-1 under vacuum.

A hydrogen atom in each of formulae described below embraces isotopes thereof (such as deuterium) and atoms constituting substituents also embrace isotopes thereof.

In the invention, the number of carbon atoms of a substituent such as alkyl group includes the number of carbon atoms, in the case where the substituent such as alkyl group has been substituted with another substituent, of the another substituent.

The term "heteroalkyl" group means an alkyl group having at least one carbon atom substituted with O, NR, or S.

In the present invention, "$C_{k-1}$ group" means that the number of carbon atoms in the group is from k to l.

The invention relates to a material selecting method used upon purifying an iridium complex by sublimation, which includes, prior to sublimation purification, selecting an iridium complex represented by formula (1) and having a rate of weight loss of 45% or greater when heated to 500° C. at a heating rate of 2° C./min under the degree of vacuum of from $1 \times 10^{-3}$ Pa to $1 \times 10^{-1}$ Pa.

A high rate of weight loss of a material when heated to 500° C. at a heating rate of 2° C./min under the degree of vacuum of from $1 \times 10^{-3}$ Pa to $1 \times 10^{-1}$ Pa is presumed to provide an indication of the ease of sublimation. Since this method using a rate of weight loss as an indication and actual sublimation differ in heating rate or a temperature at which a material is retained, the rate of weight loss does not always correspond to the sublimation purification yield. It is presumed that when a material is heated to 500° C. at a heating rate of 2° C./min under vacuum, the greater a rate of weight loss, the greater a sublimation purification yield. It has been revealed unexpectedly, however, that such a relationship does not occur in practice. During sublimation purification, the material is kept in a temperature region as high as about 200 to 500° C. for long hours so that an unsublimed portion of the material is exposed to a high-temperature condition for long hours. It is presumed that when slight decomposition occurs at this time, the decomposition product promotes further decomposition and deteriorates the sublimation purification yield. As a result of intensive investigation while thinking that a change in heat quantity upon decomposition under ordinary pressure has an influence on such a state, it has been found that compounds selected according to the method of the invention and providing a rate of weight loss of 45% or greater when heated to 500° C. at 2° C./min show an endothermic change upon thermal decomposition under ordinary pressure but have an improved sublimation purification yield. This result can be explained from the mechanism that when heat is generated upon decomposition, further decomposition is caused by application of heat at a temperature exceeding, due to the heat thus generated, that set upon sublimation purification. The reason why the reaction upon decomposition varies between an exothermic reaction and an endothermic reaction is because a change in heat quantity is large upon fusing or decomposition of trace impurities contained in the material, or when a change in the crystal form due to a difference in the crystal form occurs during the heating procedure even if the material has the utterly same composition, an exothermic reaction occurs along with the stabilization of the crystal state.

[Compound Represented by Formula (1)]

A compound represented by formula (1) will next be described.

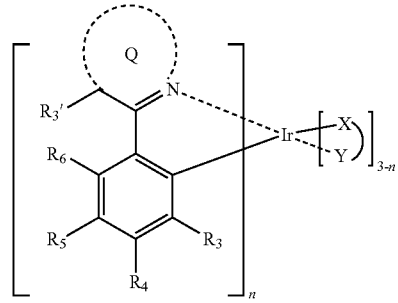

(1)

(In formula (1), each of $R_3$, $R_4$, $R_5$, $R_6$, and $R_3'$ independently represents a hydrogen atom or a substituent, with the proviso that $R_3'$ and $R_6$ may be linked to form a ring via a linking group selected from —$CR_2$—$CR_2$—, —CR=CR—, —$CR_2$—, —O—, —NR—, —O—$CR_2$—, —NR—$CR_2$—, and —N=CR—, in which each of Rs independently represents a hydrogen atom, an alkyl group, an alkenyl group, an alkynyl group, a heteroalkyl group, an aryl group, or a heteroaryl group and may further have a substituent or a plurality of the Rs may be coupled to each other to form a five- or six-membered ring, $R_3$ and $R_4$ may be coupled to each other to form a condensed four- to seven-membered ring and the condensed four- to seven-membered ring is a cycloalkane ring, cycloheteroalkane ring, aromatic hydrocarbon ring, or heteroaromatic ring and may further have a substituent, and $R_4$ and $R_5$ may be coupled to each other to form a ring;

the ring Q represents an aromatic heterocycle or condensed aromatic heterocycle having at least one nitrogen atom coordinated to iridium, with the proviso that either one of the ring Q or a benzene ring coupled to the ring Q is a condensed ring;

(X-Y) represents an ancillary ligand; and n stands for an integer from 1 to 3).

The substituent is preferably selected from the following Substituent group A.

Specific examples of substituents belonging to Substituent group A include alkyl groups, alkenyl groups, alkynyl groups, aryl groups, heteroaryl groups, amino groups, alkoxy groups, aryloxy groups, heterocyclic oxy groups, acyl groups, alkoxycarbonyl groups, aryloxycarbonyl groups, acyloxy groups, acylamino groups, alkoxycarbonylamino groups, aryloxycarbonylamino groups, sulfonylamino groups, sulfamoyl groups, carbamoyl groups, alkylthio groups, arylthio groups, heteroarylthio groups, sulfonyl groups, sulfinyl groups, ureido groups, phosphoric acid amide groups, a hydroxy group, a mercapto group, halogen groups, a cyano group, a sulfo group, a carboxyl group, a nitro group, a hydroxamic acid group, a sulfino group, a hydrazino group, an imino group, and heterocyclic groups other than the heteroaryl groups, silyl groups, silyloxy groups, and deuterium. These substituents may be substituted further with another substituent.

The alkyl groups are preferably $C_{1-30}$, more preferably $C_{1-20}$, especially preferably $C_{1-10}$ alkyl groups. Examples include methyl, ethyl, n-propyl, isopropyl, n-butyl, tert-butyl, n-octyl, n-nonyl, n-decyl, n-dodecyl, n-octadecyl, n-hexadecyl, cyclopropyl, cyclobutyl, cyclopentyl, cyclopentyl, cyclohexyl, cyclooctyl, neopentyl, 1-adamantyl, and trifluoromethyl.

The alkenyl groups are preferably $C_{2-30}$, more preferably $C_{2-20}$, especially preferably $C_{2-10}$ alkenyl groups. Examples include vinyl, allyl, 1-propenyl, 1-isopropenyl, 1-butenyl, 2-butenyl, and 3-pentenyl.

The alkynyl groups are preferably $C_{2-30}$, more preferably $C_{2-20}$, especially preferably $C_{2-10}$ alkynyl groups. Examples include ethynyl, propargyl, 1-propinyl, and 3-pentynyl.

The term "aryl group" means an aromatic hydrocarbon monoradical. When the aryl group is substituted, preferred examples of the substituent include a fluoro group, a hydrocarbon substituent, a hetero-substituted hydrocarbon substituent, and a cyano group. The aryl groups are preferably $C_{6-30}$, more preferably $C_{6-20}$, especially preferably $C_{6-12}$ aryl groups. Examples include phenyl, o-methylphenyl, m-methylphenyl, p-methylphenyl, 2,6-xylyl, p-cumenyl, mesityl, naphthyl, and anthranyl.

The term "heteroaryl group" means an aromatic heterocyclic monoradical. When it is substituted, preferred examples of the substituent include a fluoro group, a hydrocarbon substituent, a hetero-substituted hydrocarbon substituent, and a cyano group. Examples of the heterocyclic group include imidazolyl, pyrazolyl, pyridyl, pyrazyl, pyrimidyl, triazinyl, quinolyl, isoquinolinyl, pyrrolyl, indolyl, furyl, thienyl, benzoxazolyl, benzimidazolyl, benzthiazolyl, carbazolyl, and azepinyl.

The amino groups are preferably $C_{0-30}$, more preferably $C_{0-20}$, especially preferably $C_{0-10}$ amino groups. Examples include amino, methylamino, dimethylamino, diethylamino, dibenzylamino, diphenylamino, and ditolylamino.

The alkoxy groups are preferably $C_{1-30}$, more preferably $C_{1-20}$, especially preferably $C_{1-10}$ alkoxy groups. Examples include methoxy, ethoxy, butoxy, and 2-ethylhexyloxy.

The aryloxy groups are preferably $C_{6-30}$, more preferably $C_{6-20}$, especially preferably $C_{6-12}$ aryloxy groups. Examples include phenyloxy, 1-naphthyloxy, and 2-naphthyloxy.

The heterocyclic oxy groups are preferably $C_{1-30}$, more preferably $C_{1-20}$, especially preferably $C_{1-12}$ heterocyclic oxy groups. Examples include pyridyloxy, pyrazyloxy, pyrimidyloxy, and quinolyloxy.

The acyl groups are preferably $C_{2-30}$, more preferably $C_{2-20}$, especially preferably $C_{2-12}$ acyl groups. Examples include acetyl, benzoyl, formyl, and pivaloyl.

The alkoxycarbonyl groups are preferably $C_{2-30}$, more preferably $C_{2-20}$, especially preferably $C_{2-12}$ alkoxycarbonyl groups. Examples include methoxycarbonyl and ethoxycarbonyl.

The aryloxycarbonyl groups are preferably $C_{7-30}$, more preferably $C_{7-20}$, especially preferably $C_{7-12}$ aryloxycarbonyl groups. Examples include phenyloxycarbonyl.

The acyloxy groups are preferably $C_{2-30}$, more preferably $C_{2-20}$, especially preferably $C_{2-10}$ acyloxy groups. Examples include acetoxy and benzoyloxy.

The acylamino groups are preferably $C_{2-30}$, more preferably $C_{2-20}$, especially preferably $C_{2-10}$ acylamino groups. Examples include acetylamino and benzoylamino. The alkoxycarbonylamino groups are preferably $C_{2-30}$, more preferably $C_{2-20}$, especially preferably $C_{2-12}$ alkoxycarbonyl amino groups. Examples include methoxycarbonylamino.

The aryloxycarbonylamino groups are preferably $C_{7-30}$, more preferably $C_{7-20}$, especially preferably $C_{7-12}$ aryloxycarbonylamino groups. Examples include phenyloxycarbonylamino.

The sulfonylamino groups are preferably $C_{1-30}$, more preferably $C_{1-20}$, especially preferably $C_{1-12}$ sulfonylamino groups. Examples include methanesulfonylamino and benzenesulfonylamino.

The sulfamoyl groups are preferably $C_{0-30}$, more preferably $C_{0-20}$, especially preferably $C_{0-12}$ sulfamoyl groups. Examples include sulfamoyl, methylsulfamoyl, dimethylsulfamoyl, and phenylsulfamoyl.

The carbamoyl groups are preferably $C_{1-30}$, more preferably $C_{1-20}$, especially preferably $C_{1-12}$ carbamoyl groups. Examples include carbamoyl, methylcarbamoyl, diethylcarbamoyl, and phenylcarbamoyl.

The alkylthio groups are preferably $C_{1-30}$, more preferably $C_{1-20}$, especially preferably $C_{1-12}$ alkylthio groups. Examples include methylthio and ethylthio.

The arylthio groups are preferably $C_{6-30}$, more preferably $C_{6-20}$, especially preferably $C_{6-12}$ arylthio groups. Examples include phenylthio.

The heteroarylthio groups are preferably $C_{1-30}$, more preferably $C_{1-20}$, especially preferably $C_{1-12}$ heteroarylthio groups. Examples include pyridylthio, 2-benzimidazolylthio, 2-benzoxazolylthio, and 2-benzthiazolylthio.

The sulfonyl groups are preferably $C_{1-30}$, more preferably $C_{1-20}$, especially preferably $C_{1-12}$ sulfonyl groups. Examples include mesyl, tosyl, and trifluoromethanesulfonyl.

The sulfinyl groups are preferably $C_{1-30}$, more preferably $C_{1-20}$, especially preferably $C_{1-12}$ sulfinyl groups. Examples include methanesulfinyl and benzenesulfinyl.

The ureido groups are preferably $C_{1-30}$, more preferably $C_{1-20}$, especially preferably $C_{1-12}$ ureido groups. Examples include ureido, methylureido, and phenylureido.

The phosphoric acid amide groups are preferably $C_{1-30}$, more preferably $C_{1-20}$, especially preferably $C_{1-12}$ phosphoric acid amide groups. Examples include diethylphosphoric acid amide and phenylphosphoric acid amide.

Examples of the halogen atoms include fluorine, chlorine, bromine, and iodine atoms.

The heterocyclic groups other than the heteroaryl groups are preferably $C_{1-30}$, more preferably $C_{1-12}$ heterocyclic groups other than the heteroaryl groups and having, as a heteroatom, a nitrogen atom, an oxygen atom, or a sulfur atom. Specific examples include piperidyl, morpholino, and pyrrolidyl.

The silyl groups are preferably $C_{3-40}$, more preferably $C_{3-30}$, especially preferably $C_{3-24}$ silyl groups. Examples include trimethylsilyl, triethylsilyl, triisopropylsilyl, dimethyl-tert-butylsilyl, dimethylphenylsilyl, diphenyl-tert-butylsilyl, triphenylsilyl, tri-1-naphthylsilyl, and tri-2-naphthylsilyl.

The silyloxy groups are preferably $C_{3-40}$, more preferably $C_{3-30}$, especially preferably $C_{3-24}$ silyloxy groups. Examples include trimethylsilyloxy and triphenylsilyloxy.

The term "hydrocarbon substituent" means a monovalent or divalent, linear, branched, or cyclic substituent composed only of a carbon atom and a hydrogen atom. Examples of the monovalent hydrocarbon substituent include $C_{1-20}$ alkyl groups; $C_{1-20}$ alkyl groups substituted with at least one group selected from $C_{1-20}$ alkyl groups, $C_{3-8}$ cycloalkyl groups, and aryl groups; $C_{3-8}$ cycloalkyl groups; $C_{3-8}$ cycloalkyl groups substituted with at least one group selected from $C_{1-20}$ alkyl groups, $C_{3-8}$ cycloalkyl groups, and aryl groups; $C_{6-18}$ aryl groups; and aryl groups substituted with at least one group selected from $C_{1-20}$ alkyl groups, $C_{3-8}$ cycloalkyl groups, and aryl groups.

Examples of the divalent hydrocarbon group include —$CH_2$—, $CH_2CH_2$—, —$CH_2CH_2CH_2$—, and 1,2-phenylene.

These substituents may have another substituent further and substituents exemplified above as those belonging to Substituent group A can be used as the another substituent. A plurality of these substituents may be coupled to each other to form a ring.

The substituent represented by $R_3'$ is preferably an alkyl group, an aryl group, a heteroaryl group, or a halogen atom, more preferably an alkyl group or an aryl group, still more preferably an alkyl group. The alkyl group is preferably a methyl group, an ethyl group, a propyl group, a butyl group, or a pentyl group, more preferably a methyl group or an ethyl group, still more preferably a methyl group. The aryl group is preferably a phenyl group. The heteroaryl group is preferably a thienyl group. The halogen atom is preferably a fluorine atom.

$R_3'$ is preferably a hydrogen atom or an alkyl group, more preferably a hydrogen atom, a methyl group, an ethyl group, a propyl group, a butyl group, or a pentyl group, still more preferably a hydrogen atom, a methyl group, or an ethyl group, especially preferably a hydrogen atom or a methyl group.

The substituent represented by $R_5$ is preferably an alkyl group, an aryl group, or a heteroaryl group and the aryl group or heteroaryl group may have another substituent further. Examples of the another substituent include substituents selected from the Substituent group A. The alkyl group is preferably a methyl group, an ethyl group, a propyl group, a butyl group, or a pentyl group, more preferably a methyl group or an ethyl group, still more preferably a methyl group. The aryl group is preferably a phenyl group or a naphthyl group, more preferably a phenyl group. The heteroaryl group is preferably a pyridyl group, an imidazolyl group, a pyrazolyl group, a pyrazyl group, a pyrimidyl group, a triazinyl group, a quinolyl group, an isoquinolinyl group, a pyrrolyl group, an indolyl group, a furyl group, a thienyl group, a benzoxazolyl group, a benzimidazolyl group, a benzothiazolyl group, a carbazolyl group, or an azepinyl group, more preferably a pyridyl group or dibenzofuran.

$R_5$ is preferably a hydrogen atom, a methyl group, or a phenyl group, more preferably a hydrogen atom or a phenyl group.

The substituent represented by $R_3$, $R_4$, or $R_6$ is preferably an alkyl group, an aryl group, a halogen atom, or a fluoroalkyl group, more preferably an alkyl group or an aryl group. The alkyl group is preferably a methyl group, an ethyl group, a propyl group, a butyl group, or a pentyl group, more preferably a methyl group or an ethyl group, more preferably a methyl group. The aryl group is preferably a phenyl group. The halogen atom is preferably a fluorine atom. The fluoroalkyl group is preferably a trifluoromethyl group.

$R_3$ is preferably a hydrogen atom or an alkyl group, more preferably a hydrogen atom or a methyl group.

$R_4$ is preferably a hydrogen atom, an alkyl group, an aryl group, a halogen atom, or a fluoroalkyl group, more preferably a hydrogen atom, an alkyl group, or an aryl group, still more preferably a hydrogen atom or an aryl group, especially preferably a hydrogen atom or a phenyl group.

$R_6$ is preferably a hydrogen atom or a halogen atom, more preferably a hydrogen atom or a fluorine atom, still more preferably a hydrogen atom.

It is also preferred that $R_4$ and $R_5$ are coupled to each other to form a ring. In this case, $R_4$ and $R_5$ are coupled to each other to form preferably a five- or six-membered ring. The ring may further have a substituent. As the substituent, those belonging to Substituent group A can be employed.

It is especially preferred that $R_4$ and $R_5$ are coupled to each other to form a naphthalene ring together with a benzene ring coupled to the ring Q.

Examples of the aromatic heterocycle represented by the ring Q include a pyridine ring, a pyrazine ring, a pyrimidine ring, a pyrazole ring, an imidazole ring, a triazole ring, an oxazole ring, an oxadiazole ring, a thiazole ring, and a thiadiazole ring. Of these, a pyridine ring and a pyrazine ring are preferred, with a pyridine ring being more preferred.

Examples of the condensed aromatic heterocycle represented by the ring Q include a quinoline ring, an isoquinoline ring, and a quinoxaline ring. Of these, a quinoline ring and an isoquinoline ring are preferred, with a quinoline ring being more preferred.

In formula (1), either one of the ring Q or the benzene ring coupled to the ring Q is condensed.

The ring Q is preferably condensed. It is preferred that the benzene ring coupled to the ring Q has a substituent or is condensed, more preferred that it has a substituent. The substituent in this case is preferably an alkyl group or an aryl group, more preferably an aryl group.

It is especially preferred that the ring Q is condensed and at least any one of $R_3$, $R_5$, and $R_6$ represents a methyl group or a phenyl group. When any one of $R_3$, $R_4$, $R_5$, and $R_6$ represents a phenyl group, the phenyl group may further have a substituent or the phenyl group may be coupled to the ring Q via a linking group or a single bond. As the substituent, those belonging to Substituent group A can be employed. Of these, a cyano group and alkyl groups are preferred, with a cyano group and a methyl group being more preferred.

(X-Y) represents an ancillary ligand. The ligand is called "ancillary ligand", because it is presumed that the ligand does not directly contribute to photoactive properties but can change the photoactive properties of the molecule. The definition of the terms "photoactive" and "ancillary" aims at nonrestrictive theory. For example, in the bidentate ligand of Ir, n may be any of 0, 1 or 2. The ancillary ligand to be used in the light emitting material may be selected from those known in the art. Non-restrictive examples of the ancillary ligand are described in Lamansky, et al., WO02/15645A1, 89-90 incorporated by reference. Preferred examples of the ancillary ligand include acetylacetonate (acac) and picolinate (pic), and derivatives thereof. From the standpoint of stability of a complex and contribution to a high emission efficiency, the ancillary ligand is preferably acetylacetonate.

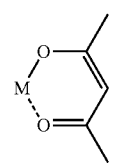

acac

The compound represented by formula (1) is more preferably a compound represented by the following formula (T-4).

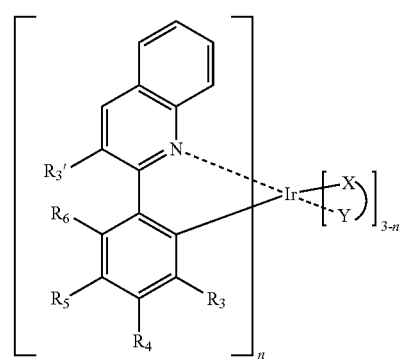

(T-4)

(In formula (T-4), $R_3'$ represents a hydrogen atom, an alkyl group, a heteroalkyl group, an aryl group, or a heteroaryl group and it may further have a substituent Z;

each of $R_3$, $R_4$, $R_5$, and $R_6$ independently represents a hydrogen atom, an alkyl group, an alkenyl group, an alkynyl group, —CN, —CF$_3$, —C$_n$F$_{2n+1}$, a trifluorovinyl group, —CO$_2$R—, —C(O)R, —NR$_2$, —NO$_2$, —OR, a halogen atom, an aryl group, or a heteroaryl group and it may further have a substituent Z. Each of Rs independently represents a hydrogen atom, an alkyl group, an alkenyl group, an alkynyl group, a heteroalkyl group, an aryl group, or a heteroaryl group and it may further have a substituent;

each of is independently represents a halogen atom, —R', —OR', —N(R')$_2$, —SR', —C(O)R', —C(O)OR', —C(O)N (R')₂—, —CN, —NO₂, —SO₂, —SOR', —SO₂R', or —SO₃R', each of R's independently represents a hydrogen atom, an alkyl group, a perhaloalkyl group, an alkenyl group, an alkynyl group, a heteroalkyl group, an aryl group, or a heteroaryl group;

R₄ and R₅ may be coupled to each other to form a ring;

(X-Y) represents an ancillary ligand; and n stands for an integer from 1 to 3).

$R_3'$, $R_3$, $R_4$, $R_5$, $R_6$, (X-Y), R, and n in formula (T-4) have the same meanings as $R_3'$, $R_3$, $R_4$, $R_5$, $R_6$, (X-Y), R, and n in formula (1) and preferred examples of them are also the same.

The following are specific examples of the compound represented by formula (1) but the invention is not limited to them.

TM-1
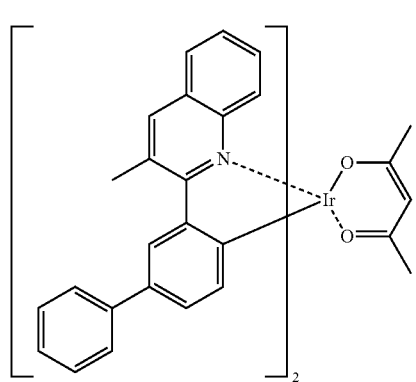

TM-2
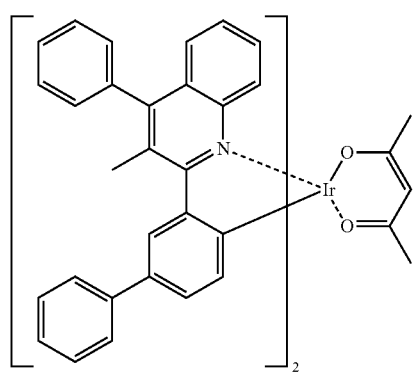

TM-3
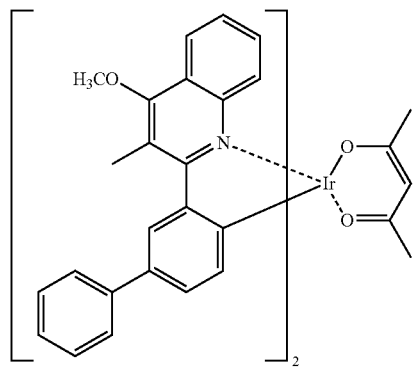

TM-4
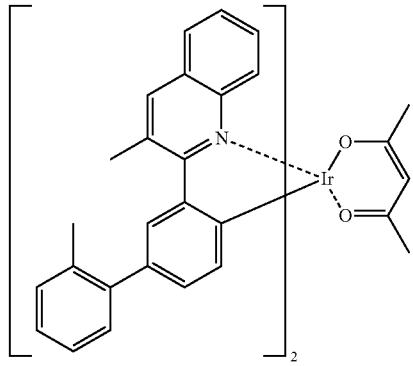

TM-5
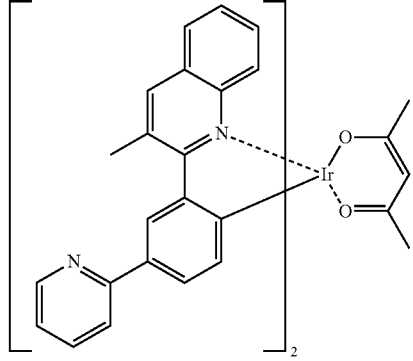

TM-6
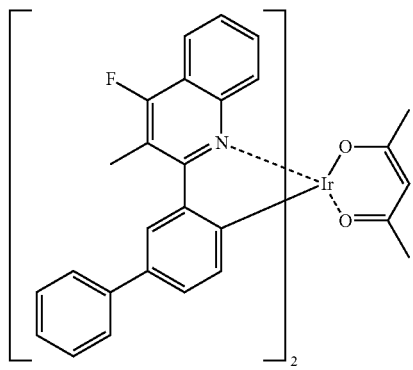

TM-7
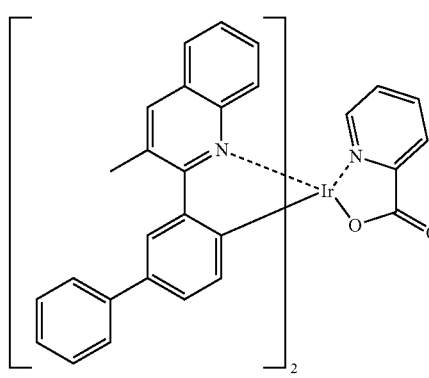

TM-8
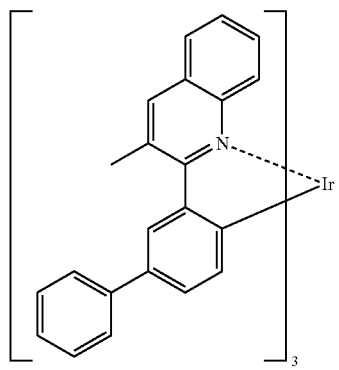
TM-9
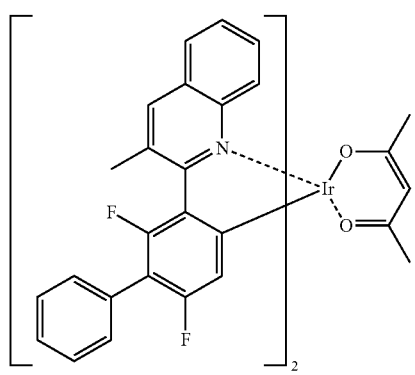
TM-10
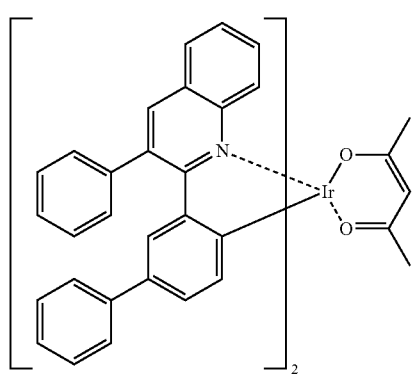
TM-11
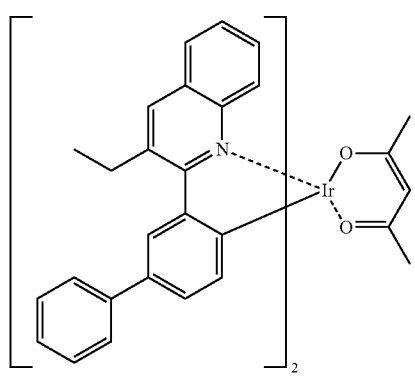
TM-12
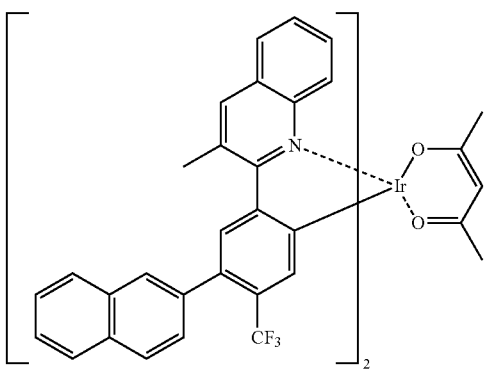
TM-13
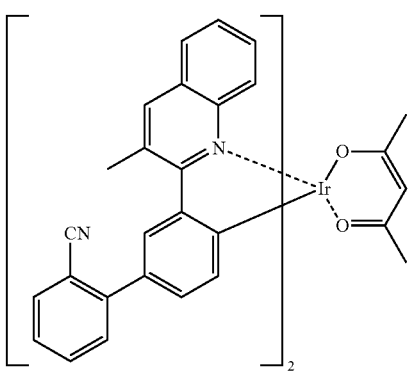
TM-14
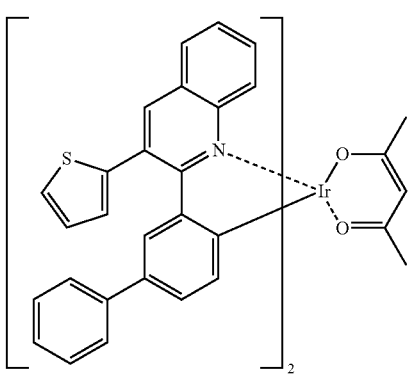
TM-15
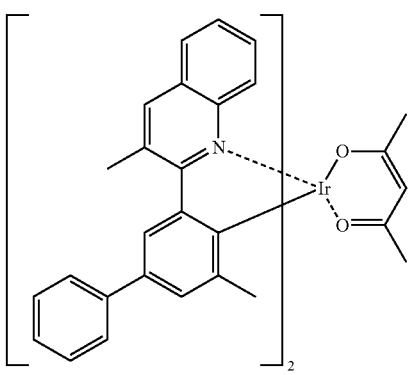

TM-16
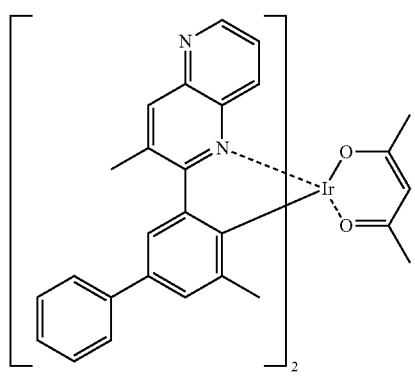
TM-17
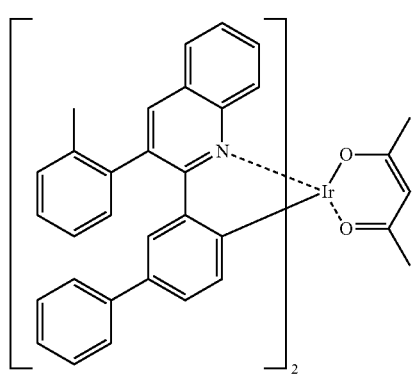
TM-18
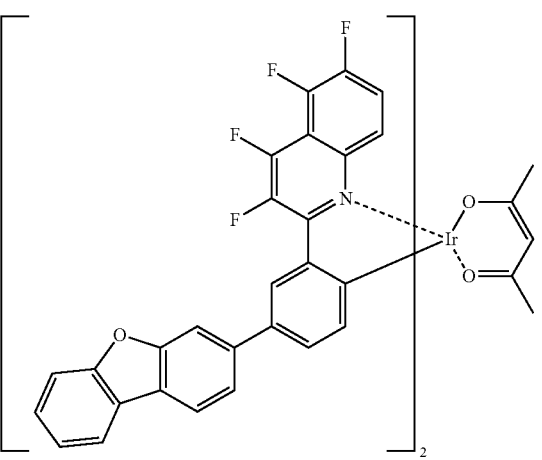
TM-19
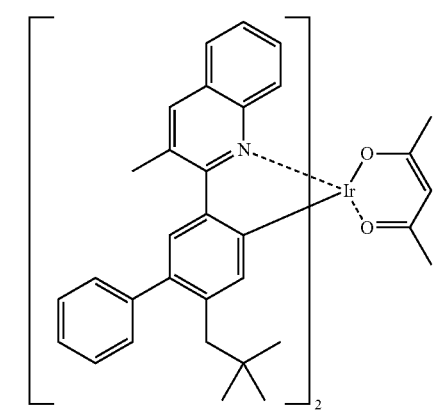
TM-20
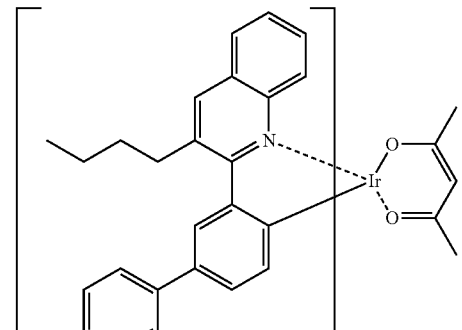
TM-21
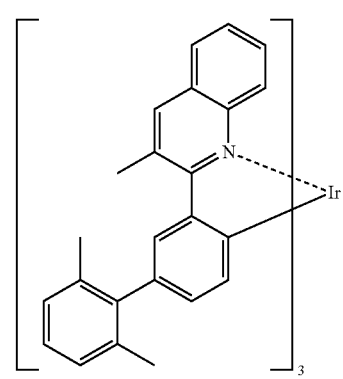
TM-22
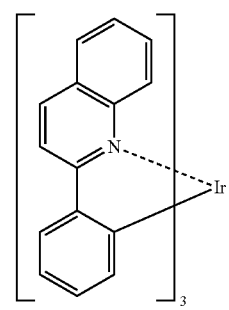
TM-23
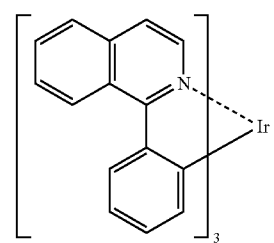
TM-24
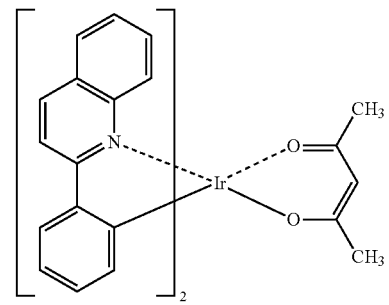

TM-25
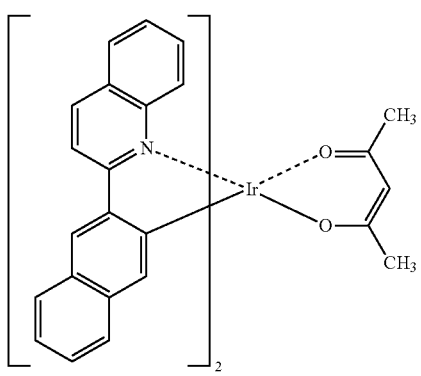
TM-26
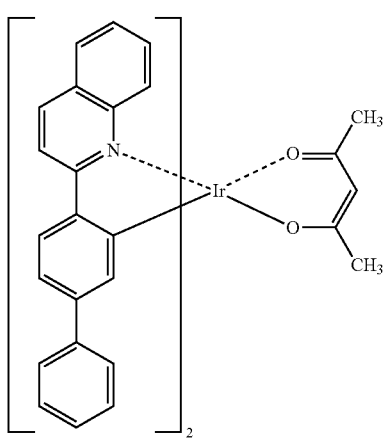
TM-27
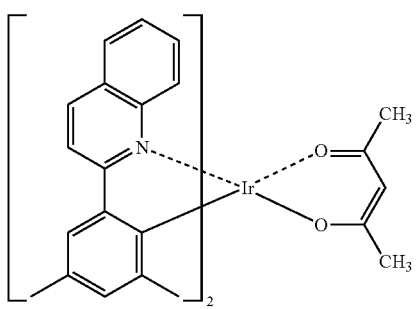
TM-28
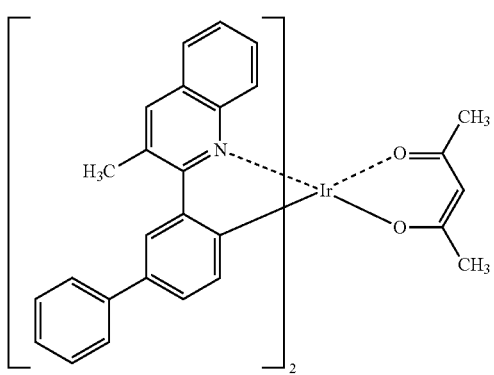
TM-29
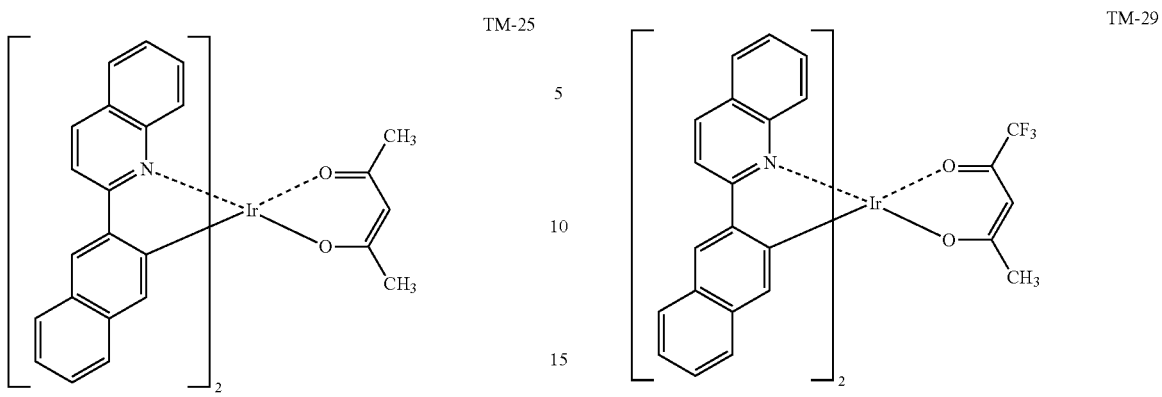
TM-30
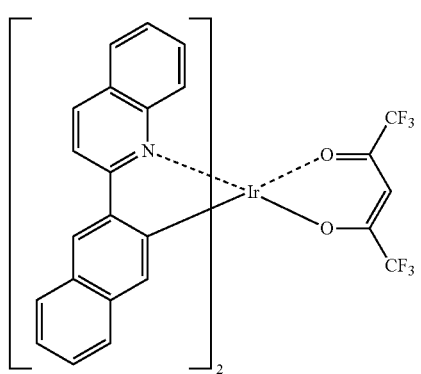
TM-31
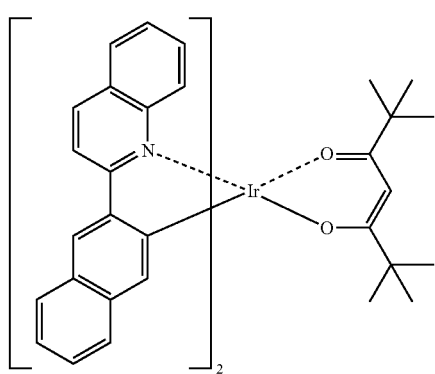
TM-32
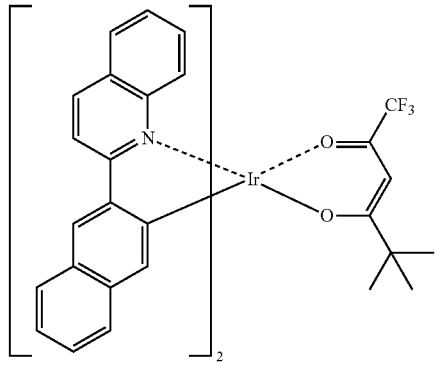
In another embodiment of the invention, the compound represented by formula (1) is preferably a compound represented by the following formula (A1) or (A3).

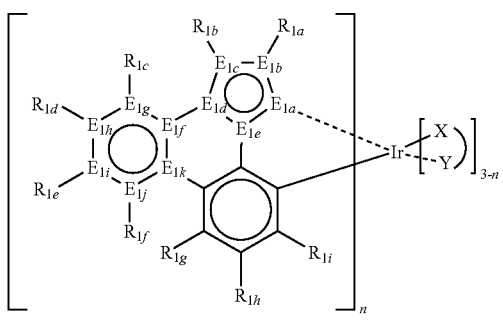

(A1)

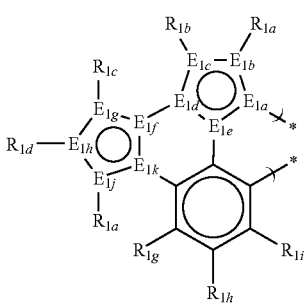

(A3')

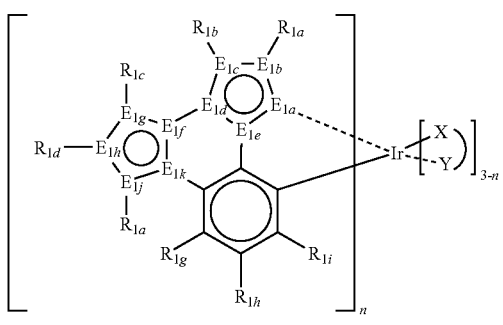

(A3)

(In formulae (A1) and (A3), each of $E_{1a}$ to $E_{1k}$ independently represents a carbon atom or a hetero atom and each of $R_{1a}$ to $R_{1i}$ independently represents a hydrogen atom or a substituent; (X-Y) represents an ancillary ligand; n stands for an integer from 1 to 3; and the compound represented by formula (A1) and the compound represented by formula (A3) each has a 18π electron structure in total).

The compound represented by formula (A1) or (A3) has a monoanionic bidentate ligand represented by formula (A1') or (A3'), respectively. The mark * in formula representing the ligand in the invention is a coordination site to iridium and each of the bond of $E_{la}$ and iridium and the bond of a carbon atom of a benzene ring having $R_{1g}$ to $R_{1i}$ and iridium may independently a covalent bond or a coordination bond.

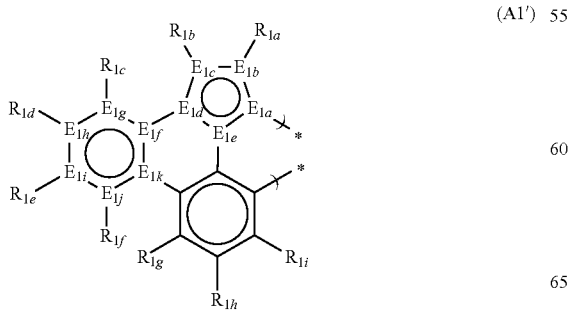

(A1')

(In formula (A1') or (A3'), each of $E_{1a}$ to $E_{1k}$ independently represents a carbon atom or a hetero atom and each of $R_{1a}$ to $R_{1i}$ independently represents a hydrogen atom or a substituent; and the bidentate ligand represented by formula (A1') and the bidentate ligand represented by formula (A3') each has a 18π electron structure in total).

The bidentate ligand represented by formula (A1') or (A3') may be coupled to another ligand to form a tridentate, a tetradentate, a pentadentate, or a hexadentate ligand.

$E_{1a}$ to $E_{1k}$ may be selected from a carbon atom and hetero atoms, preferably from a carbon atom and a nitrogen atom. $E_{1a}$ and $E_{1p}$ are preferably atoms different from each other. The metal complex has an 18π electron structure.

The ring formed of $E_{1a}$ to $E_{1e}$ represents a five-membered heterocycle and specific examples of it include oxazole, thiazole, isoxazole, isothiazole, pyrrole, imidazole, pyrazole, triazole, and tetrazole. Of these, imidazole and pyrazole are preferred, with imidazole being more preferred.

Each of the rings formed of $E_{1f}$ to $E_{1k}$ and $E_{1l}$ to $E_{1k}$ is independently selected from six-membered aromatic hydrocarbon rings and five- or six-membered heterocycles. Examples include benzene, oxazole, thiazole, isoxazole, isothiazole, oxadiazole, thiadiazole, furan, thiophene, pyrrole, imidazole, pyrazole, triazole, pyridine, pyrazine, pyrimidine, pyridazine, and triazine.

Each of $R_{1a}$ to $R_{1i}$ is independently selected from Substituent group A described above and is preferably a hydrogen atom, a hydrocarbon substituent, a cyano group, a fluoro group, $OR_{2a}$, $SR_{2a}$, $NR_{2a}R_{2b}$, $BR_{2a}R_{2b}$, or $SiR_{2a}R_{2b}R_{2c}$. Each of $R_{2a}$ to $R_{2c}$ independently represents a hydrocarbon substituent, or a hydrocarbon substituent substituted with a hetero atom. Two of $R_{1a}$ to $R_{1i}$ and $R_{2a}$ to $R_{2c}$ may be coupled to each other to form a saturated or unsaturated, aromatic or non-aromatic ring. When each of $R_{1a}$ to $R_{1i}$ is coupled to a nitrogen atom, it is not a hydrogen atom.

The hetero atom means an atom other than a carbon atom or a hydrogen tom. Examples of the hetero atom include oxygen, nitrogen, phosphorus, sulfur, selenium, arsenic, chlorine, bromine, silicon and fluorine.

At least one of $R_{1a}$ to $R_{1i}$ is an aryl group having a dihedral angle of 70 degrees or greater with its basic structure, more preferably a substituent represented by the below-described formula ss-1, still more preferably a 2,6-disubstituted aryl group. It is most preferred that $R_{1b}$ is a 2,6-disubstituted aryl group.

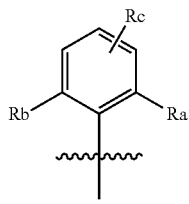

(In formula ss-1, each of Ra, Rb, and Rc independently represents any of a hydrogen atom, an alkyl group, and an aryl group).

The alkyl group represented by Ra, Rb, or Rc is preferably a $C_{1-30}$, more preferably $C_{1-20}$, especially preferably $C_{1-10}$ alkyl group. Examples include methyl, ethyl, n-propyl, isopropyl, n-butyl, tert-butyl, n-octyl, n-nonyl, n-decyl, n-dodecyl, n-octadecyl, n-hexadecyl, cyclopropyl, cyclobutyl, cyclopentyl, cyclohexyl, cyclooctyl, 1-adamantyl, and trifluoromethyl. Of these, methyl and isopropyl groups are preferred.

The aryl group represented by Ra, Rb, or Rc is preferably a $C_{6-30}$, more preferably $C_{6-20}$, especially preferably $C_{6-12}$ aryl group. Examples include phenyl, o-methylphenyl, m-methylphenyl, p-methylphenyl, 2,6-xylyl, p-cumenyl, mesityl, naphthyl, and anthranyl. Of these, a phenyl group is preferred.

It is preferred that at least one of Ra and Rb is selected from the alkyl groups and the aryl groups. It is more preferred that at least one of Ra and Rb is selected from the alkyl groups, still more preferred that both of Ra and Rb are selected from the alkyl groups, most preferred that both of Ra and Rb are methyl groups or isopropyl groups.

The 2,6-disubstituted aryl group is preferably a 2,6-dimethylphenyl group, a 2,4,6-trimethylphenyl group, a 2,6-diisopropylphenyl group, a 2,4,6-triisopropylphenyl group, a 2,6-dimethyl-4-phenylphenyl group, a 2,6-dimethyl-4-(2,6-dimethylpyridin-4-yl)phenyl group, a 2,6-diphenylphenyl group, a 2,6-diphenyl-4-isopropylphenyl group, a 2,4,6-triphenylphenyl group, a 2,6-diisopropyl-4-(4-isopropylphenyl)phenyl group, a 2,6-diisopropyl-4-(3,5-dimethylphenyl)phenyl group, a 2,6-diisopropyl-4-(pyridin-4-yl)phenyl group, or a 2,6-di-(3,5-dimethylphenyl)phenyl group.

It is preferred that at least one of $R_{1a}$ to $R_{1i}$ is the alkyl group, more preferred that $R_{1e}$ is the alkyl group. The alkyl group is preferably composed of four or more carbon atoms and branched at a site distant from the benzyl position.

In the invention, the metal complex having the ligand of formula may be composed of a main ligand or tautomer thereof and an ancillary ligand or tautomer thereof; or all the ligands of the metal complex may be composed of a partial structure represented by the main ligand or tautomer thereof.

The metal complex may contain, as an ancillary ligand, ligands which are used for the formation of conventionally known metal complexes and are known, as a so-called ligand, to those skilled in the art (which may also be called "coordination compounds") as needed.

In order to successfully gain the advantage described in the invention, the complex contains preferably one or two ligands, more preferably one ligand. When a reactive group is introduced into the molecule of the complex, using two ligands is also preferred from the standpoint of ease of synthesis.

As the ligands used for the formation of conventionally known metal complexes, there are various known ligands. Examples include those described in H. Yersin, *Photochemistry and Photophysics of Coordination Compounds*, Springer-Verlag A.G. (1987) and Akio Yamamoto, *Organometallic Chemistry—Fundamental and Application—* Shokabo Publishing Co., Ltd. (1982) (for example, halogen ligands, preferably a chlorine ligand, nitrogen-containing heteroaryl ligands such as bipyridyl and phenanthroline, and diketone ligands such as acetylacetone). Of these, the diketones and picolinic acid derivatives are preferred.

The following are specific examples of the ancillary ligand but the invention is not limited thereto.

(I-1)

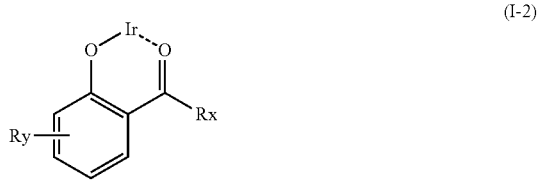

(I-2)

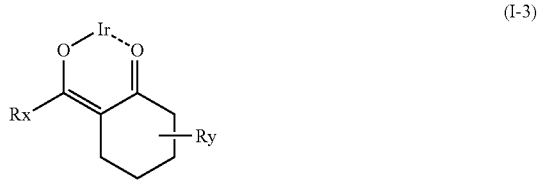

(I-3)

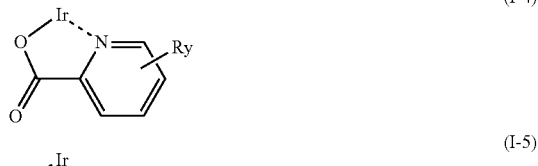

(I-4)

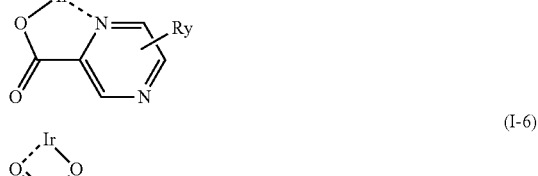

(I-5)

(I-6)

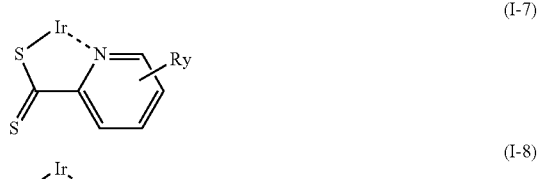

(I-7)

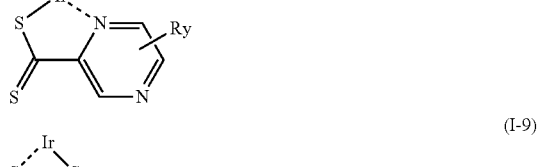

(I-8)

(I-9)

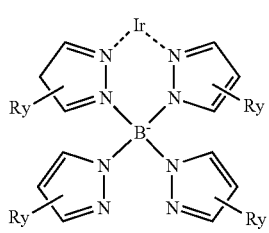
(I-10)

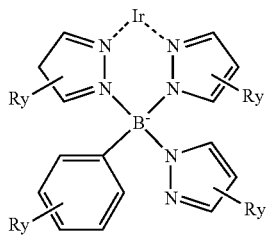
(I-11)

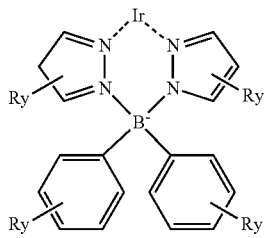
(I-12)

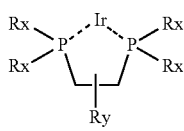
(I-13)

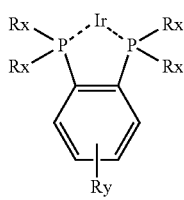
(I-14)

In the above examples of the ancillary ligand, each of Rx, Ry, and Rz independently represents a hydrogen atom or a substituent.

The compound represented by formula (A1) or (A3) is preferably a compound represented by the following formula (A1-1) or (A3-1), respectively.

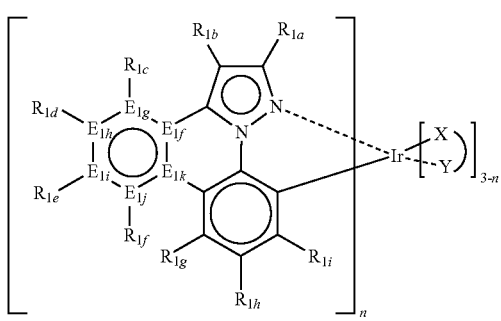
(A1-1)

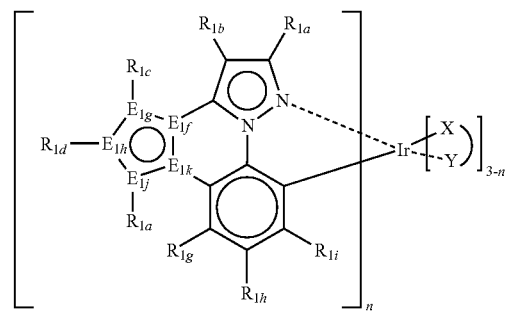
(A3-1)

(In formulae (A1-1) and (A3-1), each of $E_{1f}$ to $E_{1k}$ independently represents a carbon atom or a hetero atom and each of $R_{1a}$ to $R_{1i}$ independently represents a hydrogen atom or a substituent; (X-Y) represents an ancillary ligand; n stands for an integer from 1 to 3; and the compound represented by formula (A1-1) and the compound represented by formula (A3-1) each has a 18π electron structure in total).

In formulae (A1-1) and (A3-1), $E_{1a}$ to $E_{1e}$, $E_{1o}$ to $E_{1q}$, $E_{1l}$ to $E_{1n}$, and $R_{1a}$ to $R_{1i}$ respectively have the same meanings as $E_{1a}$ to $E_{1e}$, $E_{1o}$ to $E_{1q}$, $E_{1l}$ to $E_{1n}$, and $R_{1a}$ to $R_{1i}$ defined in formulae (A1) and (A3). Preferred examples of them are also the same.

The compounds represented by formula (A1) or (A3) are preferably compounds represented by the following formulae (A1-2) or (A3-2), respectively.

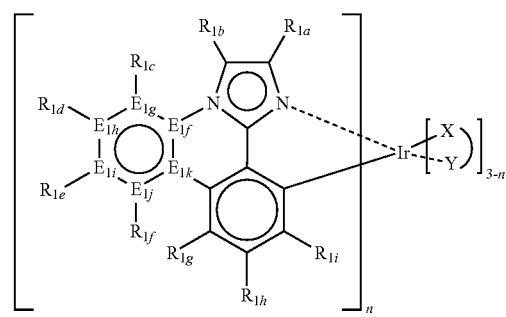
(A1-2)

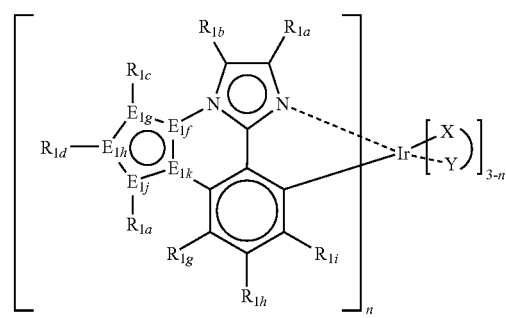
(A3-2)

(In formulae (A1-2) and (A3-2), each of $E_{1f}$ to $E_{1k}$ independently represents a carbon atom or a hetero atom; each of $R_{1a}$ to $R_{1i}$ independently represents a hydrogen atom or a substituent; (X-Y) represents an ancillary ligand; n stands for an integer from 1 to 3; and the compound represented by formula (A1-2) and the compound represented by formula (A3-2) each has a 18π electron structure in total).

In formulae (A1-2) and (A3-2), $E_{1o}$ to $E_{1q}$, $E_{1l}$ to $E_{1n}$, and $R_{1a}$ to $R_{1i}$ respectively have the same meanings as $E_{1o}$ to $E_{1q}$, $E_{1l}$ to $E_{1n}$, and $R_{1a}$ to $R_{1i}$ defined in formulae (A1-1) and (A3-1). Preferred examples of them are also the same.

In the invention, the compound represented by formula (A1-2) is more preferred and the compound of formula (A1-2) is still more preferably the compound represented by formula (A1-3).

(A1-3)

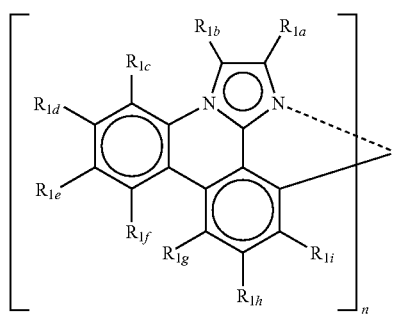

(In formula (A1-3), each of $R_{1a}$ to $R_{1i}$ independently represents a hydrogen atom or a substituent; (X-Y) represents an ancillary ligand; n stands for an integer from 1 to 3; and the compound represented by formula (A1-3) has a 18π electron structure).

In formula (A1-3), $R_{1a}$ to $R_{1i}$ respectively have the same meanings as $R_{1a}$ to $R_{1i}$ defined in formula (A1). Preferred examples of them are also the same.

The following are specific preferred examples of the compounds represented by formulae (A1') and (A3'). Of these, compounds (X-64) to (X-68) are preferred.

X-1

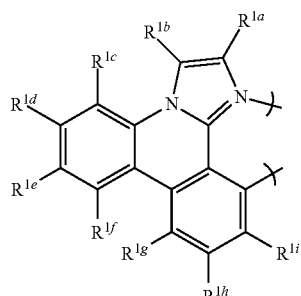

X-2

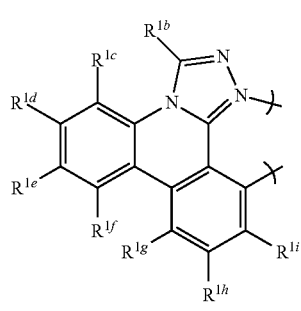

X-3

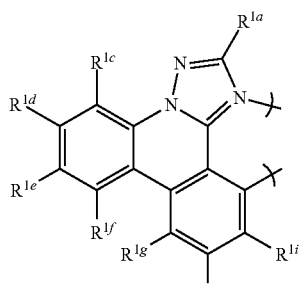

X-4

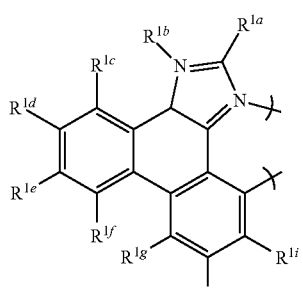

X-5

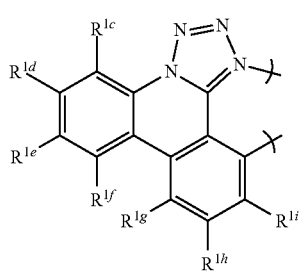

X-6

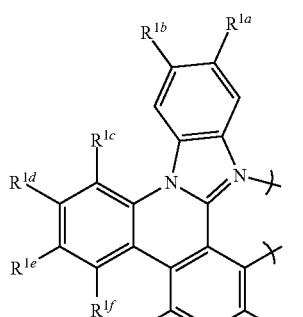

X-7

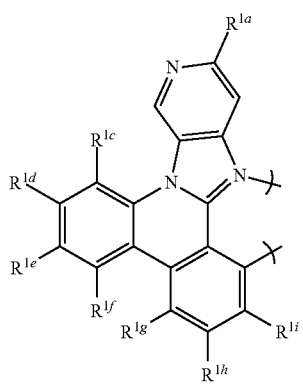

X-8, X-9, X-10, X-11, X-12, X-13, X-14, X-15

X-16
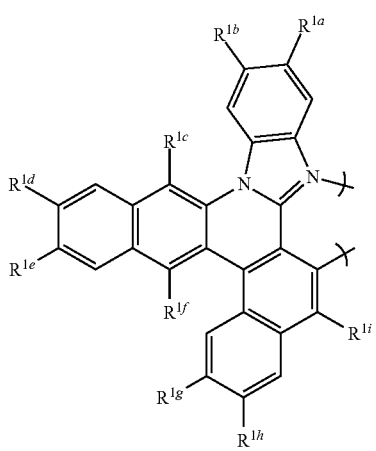
X-17
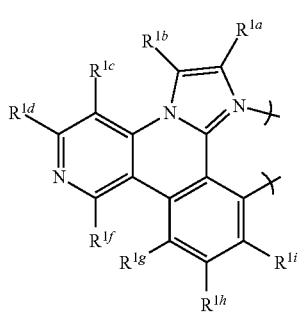
X-18
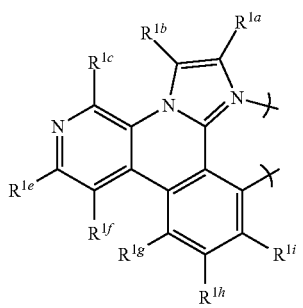
X-19
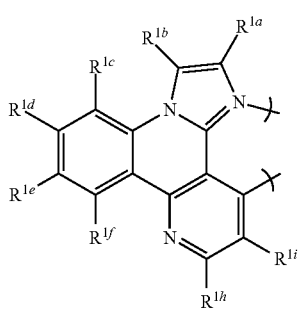
X-20
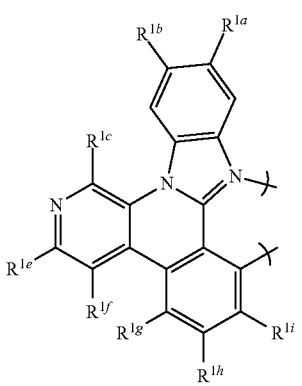
X-21
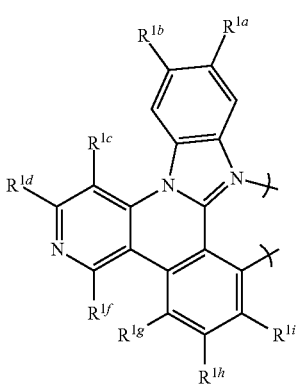
X-22
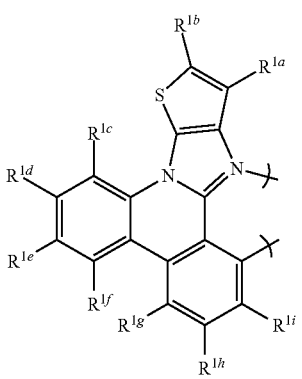
X-23
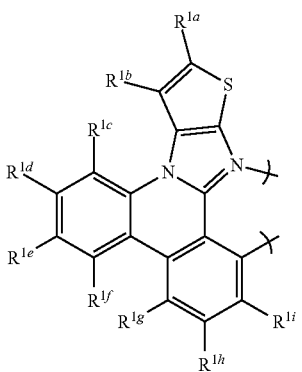

X-24
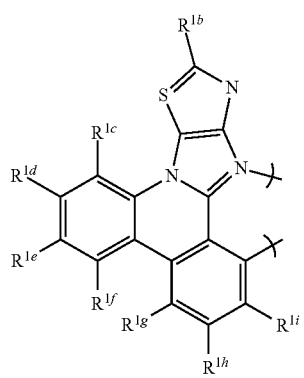
X-25
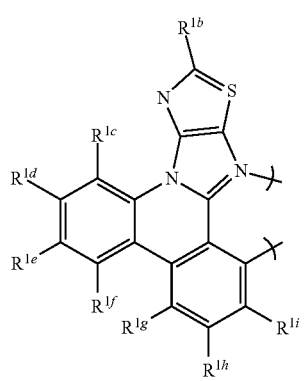
X-26
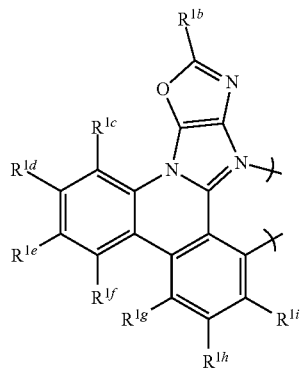
X-27
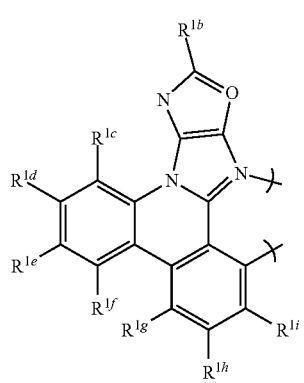
X-28
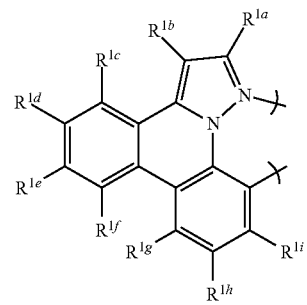
X-29
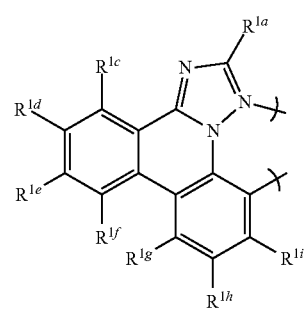
X-30
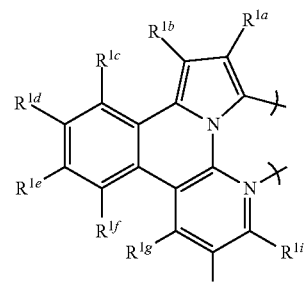
X-31
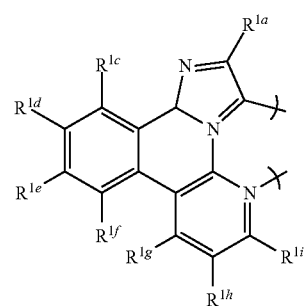
X-32
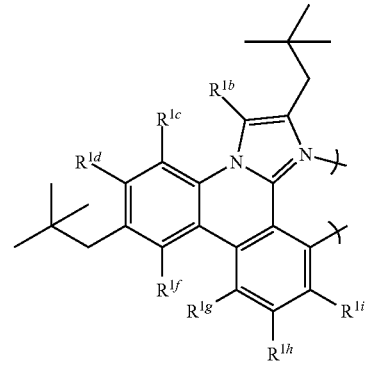

-continued
X-33
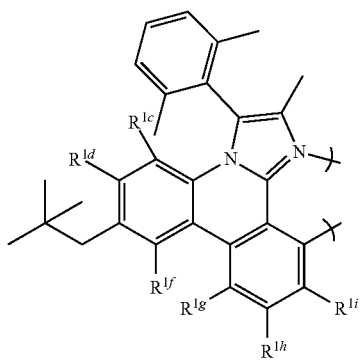
X-34
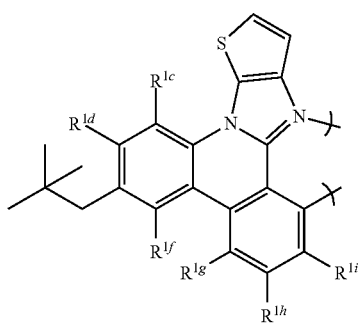
X-35
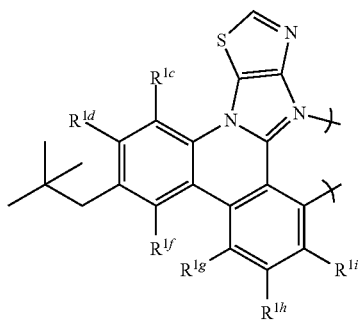
X-36
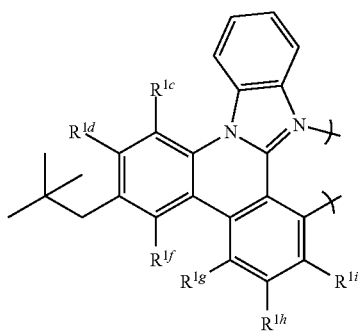
-continued
X-37
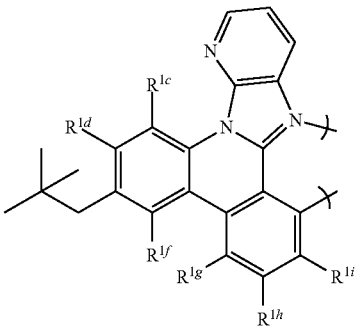
X-38
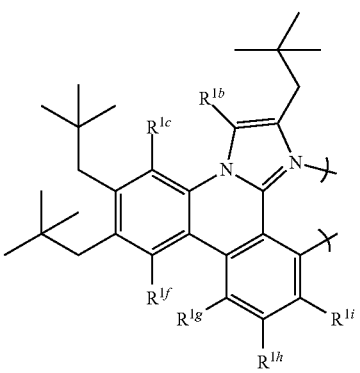
X-39
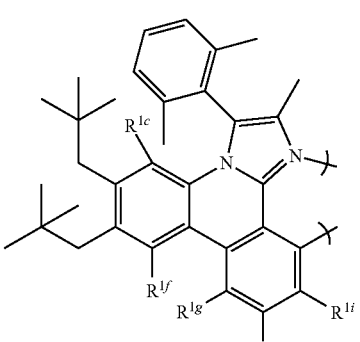
X-40
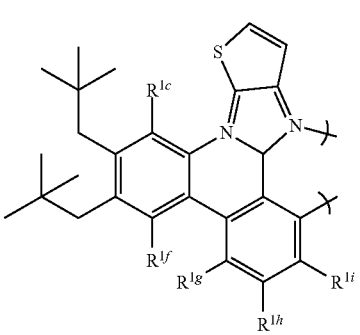

X-41
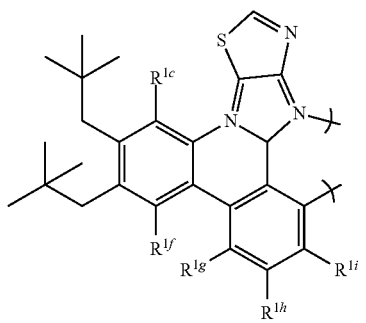
X-42
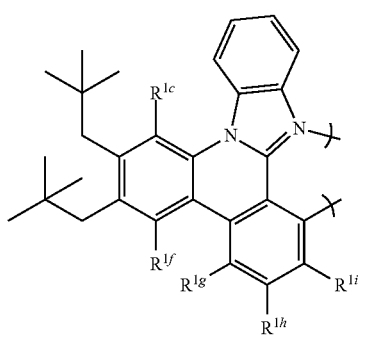
X-43
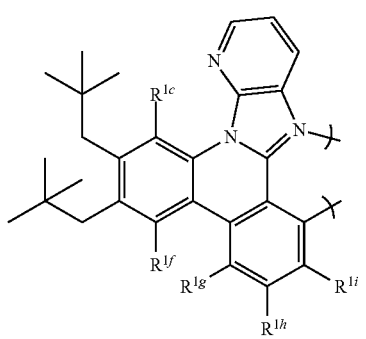
X-44
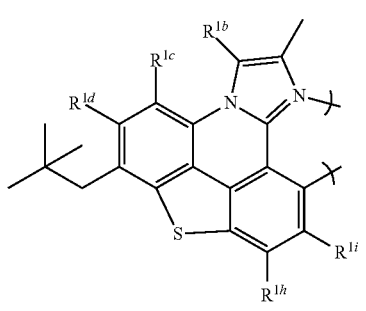
X-45
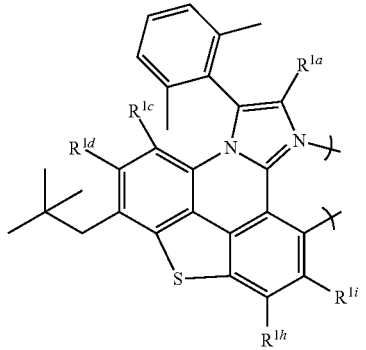
X-46
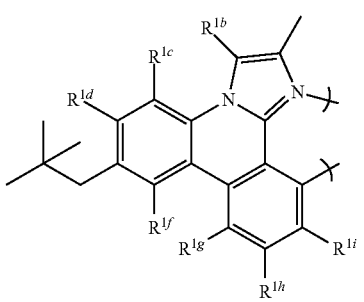
X-47
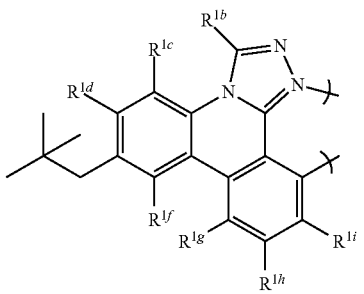
X-48
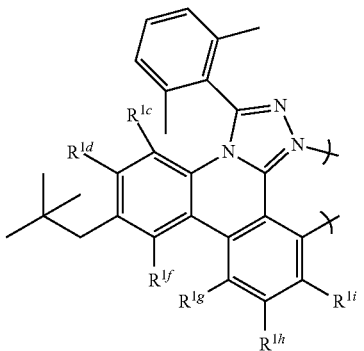
X-49
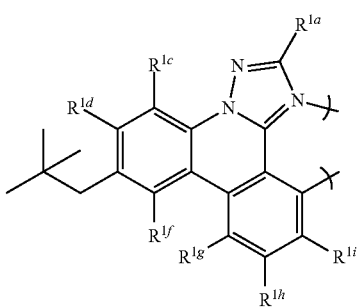
X-50
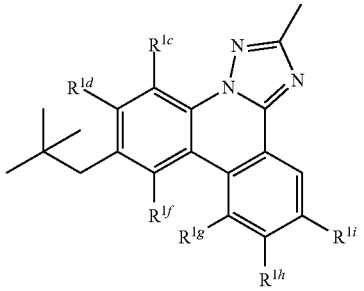

X-51
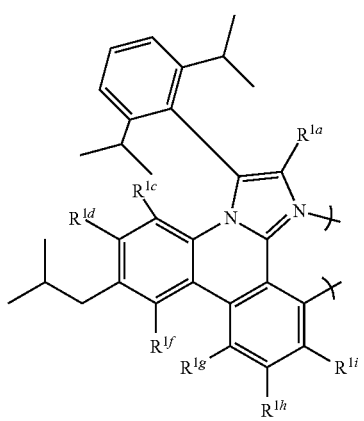
X-52
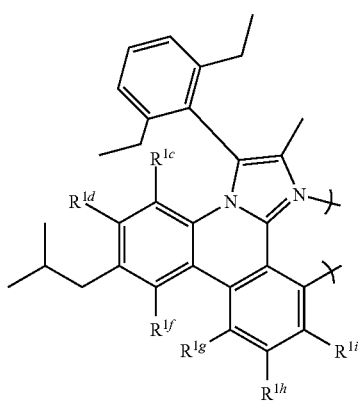
X-53
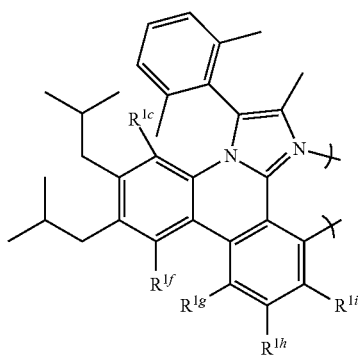
X-54
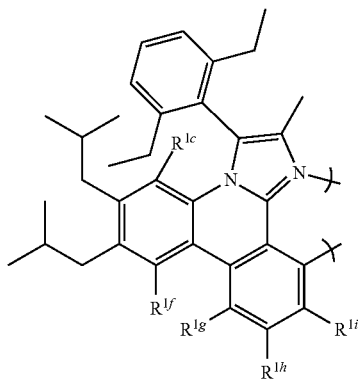
X-55
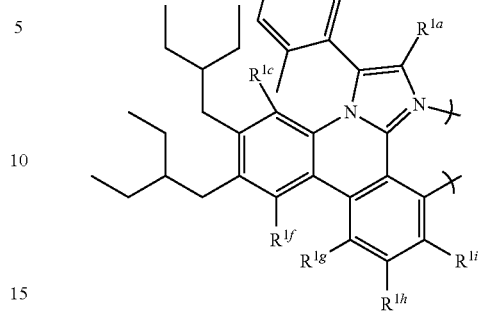
X-56
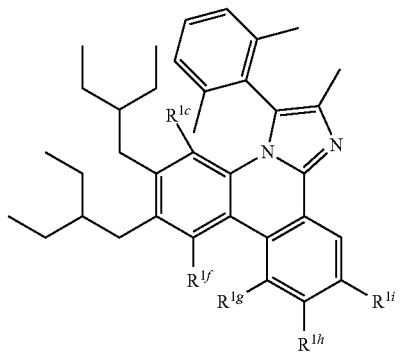
X-57
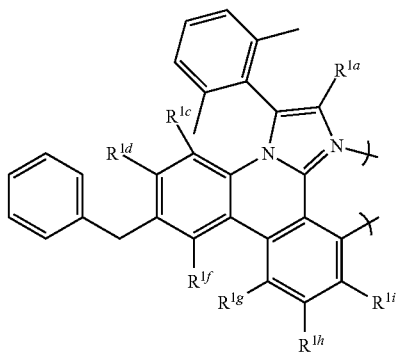
X-58
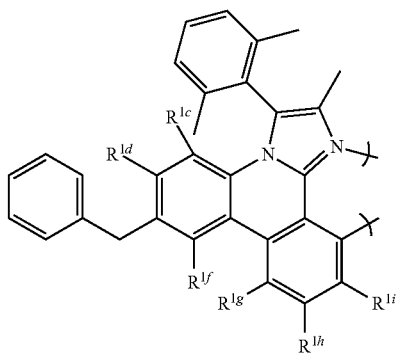

X-59
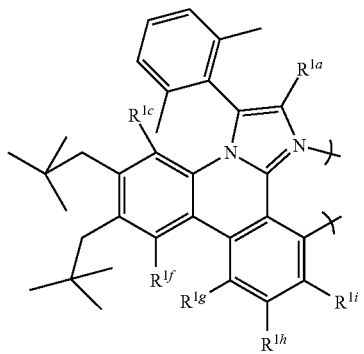
X-60
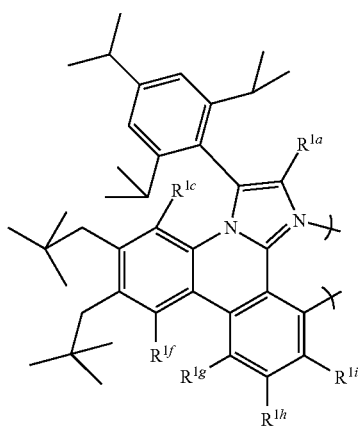
X-61
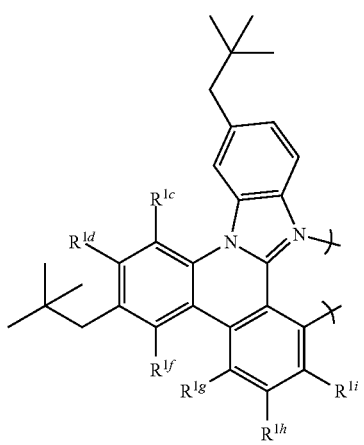
X-62
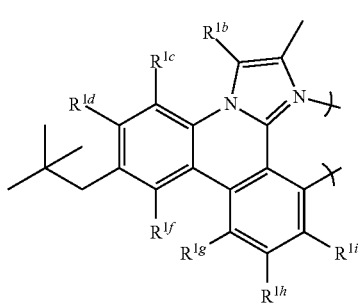
X-63
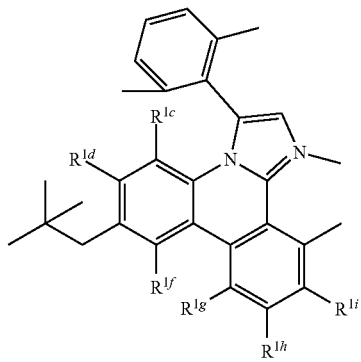
X-64
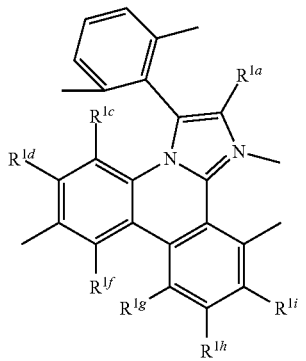
X-65
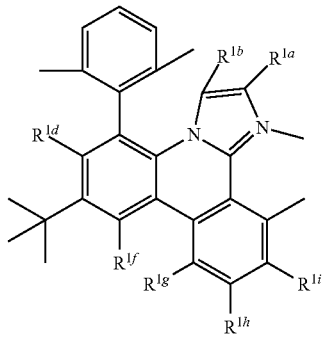
X-66
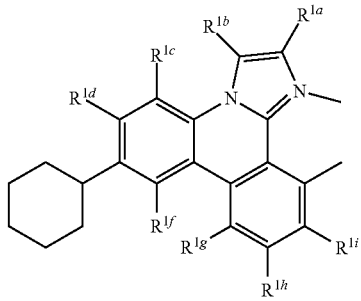

-continued

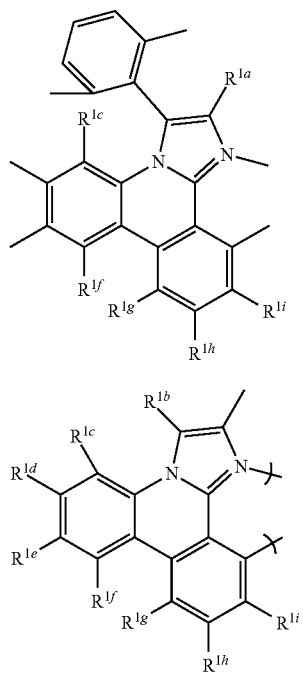

X-67

X-68

$R^{1a}$ to $R^{1i}$ have the same meanings as those defined in formula (A1). It is preferred that all of them represent a hydrogen atom.

The compound represented by formula (A1) or (A3) can be synthesized by various processes such as those described in US2007/0190359 or US2008/0297033.

For example, it can be obtained by cooling, to a temperature not greater than room temperature, or heating (not only ordinary heating but also heating with microwaves is also effective) a ligand or dissociate thereof and a metal compound in a solvent (such as halogen solvent, alcohol solvent, ether solvent, ester solvent, ketone solvent, nitrile solvent, amide solvent, sulfone solvent, sulfoxide solvent, or water) or in a solventless manner in the presence or absence of a base (various inorganic or organic bases such as sodium methoxide, t-butoxy potassium, triethylamine, and potassium carbonate). More specifically, XM-64 can be synthesized by a process described in paragraphs [0132] to [0134] of US2007/0190359 while using 7-methylimidazophenanthridine as a starting raw material. XM-63 can be synthesized by a process described in paragraphs [0281] to [0287] of US2008/0297033.

In the invention, of the compound represented by formula (T-4) and the compound represented by formula (A1) or (A3), the compound represented by formula (T-4) is more preferred.

[Material Selecting Method]

The material selecting method in the invention is a method of selecting an iridium complex upon purifying the iridium complex by sublimation. This method includes selecting an iridium complex represented by the above formula (1) and having a rate of weight loss of 45% or greater when heated to 500° C. at 2° C./min under the degree of vacuum of $1 \times 10^{-3}$ Pa or greater but not greater than $1 \times 10^{-1}$ Pa.

The rate of weight loss is determined based on the following equation:

Rate of weight loss (%)=((Initial weight)−(weight after heating))/(initial weight)×100.

The degree of vacuum can be measured by using a vacuum gauge attached to an apparatus and it is preferably $1.0 \times 10^{-3}$ Pa or greater but not greater than $1 \times 10^{-2}$ Pa. Although no particular limitation is imposed on the degree of vacuum, it can be adjusted, for example, by the valve operation of a vacuum line.

In the invention, an iridium complex having a rate of weight loss of 45% or greater when heated to 500° C. at a rate of 2° C./min under the above conditions is selected. An iridium complex having a rate of weight loss of 48% or greater when heated to 500° C. at a rate of 2° C./min is preferred, with an iridium complex having a rate of weight loss of 55% or greater when heated to 500° C. at a rate of 2° C./min being more preferred. Although no particular limitation is imposed on the rate of weight loss, it can be measured by using, for example, thermogravimetric analysis (TG).

The heating is performed preferably from normal temperature to 500° C., more preferably from 30° C. to 500° C.

The iridium complex preferably undergoes an endothermic change as a thermal change within a range of a rate of weight loss of from 1 to 5 mass % when heated at a rate of 10° C./min under ordinary pressure from the standpoint of excellent sublimation purification efficiency. They can be measured by simultaneous thermogravimetry and differential thermal analysis (TG-DTA).

The iridium complex has preferably been purified by using column chromatography because trace impurities that deteriorate a sublimation property can be removed easily.

The iridium complex has preferably been purified by sublimation because trace impurities that deteriorate a sublimation property can be removed easily.

[Organic Electroluminescence Device]

The device of the invention will next be described in detail.

The organic electroluminescence device of the invention has, on a substrate thereof, a pair of electrodes and a light emitting layer between the electrodes. The light emitting layer is an organic layer and the device may have a plurality of organic layers further.

At least one of the anode and the cathode is preferably transparent or translucent in consideration of the properties of the device.

FIG. 1 illustrates an example of the constitution of the organic electroluminescence device according to the invention. An organic electroluminescence device 10 of FIG. 1 relating to the invention has, on a supporting substrate 12, a light emitting layer 6 sandwiched between an anode 3 and a cathode 9. More specifically, a hole injection layer 4, a hole transport layer 5, a light emitting layer 6, a hole blocking layer 7, and an electron transport layer 8 are stacked one after another in the order of mention between the anode 3 and the cathode 9.

<Constitution of Organic Layers>

No particular limitation is imposed on the layer constitution of the organic layers and it can be selected as needed, depending on the intended use or using purpose of the organic electroluminescence device. The organic layers are formed on the transparent electrode or a back-side electrode. In this case, the organic layer is formed on the front surface or one surface of the transparent electrode or the back-side electrode.

The shape, size, and thickness of the organic layers are not particularly limited and can be selected as needed in accordance with the using purpose.

The following are specific examples of the layer constitution but the layer constitution of the invention is not limited to them.

Anode/hole transport layer/light emitting layer/electron transport layer/cathode Anode/hole transport layer/light emitting layer/blocking layer/electron transport layer/cathode Anode/hole transport layer/light emitting layer/blocking layer/electron transport layer/electron injection layer/cathode Anode/hole injection layer/hole transport layer/light emitting layer/blocking layer/electron transport layer/cathode Anode/hole injection layer/hole transport layer/light emitting layer/blocking layer/electron transport layer/electron injection layer/cathode The device structure, substrate, cathode, and anode of the organic electroluminescence device are described in detail, for example, in Japanese Patent Laid-Open No. 2008-270736 and the description therein can be applied to the invention.

<Substrate>

The substrate to be used in the invention preferably does not scatter or attenuate light emitted from the organic layer. A substrate made of an organic material has preferably excellent heat resistance, size stability, solvent resistance, electrical insulating properties, and processability.

<Anode>

It is usually sufficient that the anode has a function of supplying holes to the organic layer. The shape, structure and size thereof are not particularly limited, and can be selected as needed from known electrode materials, depending on the intended use or using purpose of the luminescence device. As described above, it is usually provided as a transparent anode.

<Cathode>

It is usually sufficient that the cathode has a function as an electrode injecting electrons to the organic layer. The shape, structure and size thereof are not particularly limited, and can be selected as needed from known electrode materials, depending on the intended use or using purpose of the luminescence device.

With regards to the substrate, anode, and cathode, the description in the paragraphs from [0070] to [0089] of Japanese Patent Laid-Open No. 2008-270736 can be applied to the invention.

<Organic Layer>

The organic layer of the invention will next be described.

—Formation of Organic Layer—

In the organic electroluminescence device of the invention, each organic layer can be formed suitably by any of dry film formation processes such as vapor deposition and sputtering, transfer process, printing process, and the like.

(Light Emitting Layer)

<Light Emitting Material>

The light emitting material is preferably the compound represented by formula (1).

The light emitting material is usually contained in an amount of from 0.1 mass % to 50 mass % in the light emitting layer based on the total mass of the compounds constituting the light emitting layer. From the standpoint of durability and external quantum efficiency, the amount is preferably from 1 mass % to 50 mass %, more preferably from 2 mass % to 40 mass %.

Although the thickness of the light emitting layer is not particularly limited, usually a thickness of from 2 nm to 500 nm is preferred. From the standpoint of external quantum efficiency, it is preferably from 3 nm to 200 nm, more preferably from 5 nm to 100 nm.

The light emitting layer may be composed only of a light emitting material or may be a mixed layer of a host material and a light emitting material. The light emitting material may be either a fluorescent material or a phosphorescent material. As a dopant, one or more dopants may be used. The host material is preferably a charge transport material. As the host material, one or more host materials may be used. For example, a mixture of an electron transporting host material and a hole transporting host material may be used. The light emitting layer may contain a material having no charge transport property and emitting no light.

<Host Material>

Examples of the host material include pyrrole, indole, carbazole (for example, CBP (4,4'-di(9-carbazoyl)biphenyl)), azaindole, azacarbazole, triazole, oxazole, oxadiazole, pyrazole, imidazole, thiophene, polyarylalkane, pyrazoline, pyrazolone, phenylenediamine, arylamine, amino-substituted chalcone, styrylanthracene, fluorenone, hydrazone, stilbene, silazane, aromatic tertiary amine compounds, styrylamine compounds, porphyrin compounds, polysilane compounds, poly(N-vinylcarbazole), aniline copolymers, electrically conductive high-molecular oligomers such as thiophene oligomers, polythiophene and the like, organosilanes, carbon films, pyridine, pyrimidine, triazine, imidazole, pyrazole, triazole, oxazole, oxadiazole, fluorenone, anthraquinodimethane, anthrone, diphenylquinone, thiopyran dioxide, carbodiimide, fluorenylidenemethane, distyrylpyrazine, fluorine-substituted aromatic compounds, heterocyclic tetracarboxylic anhydrides such as naphthalene perylene and the like, phthalocyanine, and a variety of metal complexes represented by metal complexes of a 8-quinolinol derivative, metal phthalocyanine, and metal complexes having benzoxazole or benzothiazole as the ligand thereof, and derivatives thereof (which may have a substituent or a condensed ring).

Although the content of the host compound in the invention is not particularly limited, it is preferably 15 mass % or greater but not greater than 98 mass % based on the total mass of the compounds constituting the light emitting layer from the standpoint of emission efficiency and drive voltage.

(Fluorescent Material)

Examples of the fluorescent material usable in the invention include benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, condensed aromatic compounds, perinone derivatives, oxadiazole derivatives, oxazine derivatives, aldazine derivatives, pyralidine derivatives, cyclopentadiene derivatives, bisstyrylanthracene derivatives, quinacridone derivatives, pyrrolopyridine derivatives, thiadiazolopyridine derivatives, cyclopentadiene derivatives, styrylamine derivatives, diketopyrrolopyrrole derivatives, aromatic dimethylidyne compounds, various complexes typified by complexes of a 8-quinolinol derivative or a pyrromethene derivative, polymer compounds such as polythiophene, polyphenylene, and polyphenylenevinylene, and organosilane derivatives.

(Phosphorescent Material)

Examples of the phosphorescent material usable in the invention include, in addition to the compound represented by formula (1), phosphorescent compounds described in patent documents such as U.S. Pat. Nos. 6,303,238B1 and 6,097,147, WO 00/57676, 00/70655, 01/08230, 01/39234A2, 01/41512A1, 02/02714A2, 02/15645A1, 02/44189A1, and 05/19373A2, Japanese Patent Laid-Open Nos. 2001-247859, 2002-302671, 2002-117978, 2003-133074, 2002-235076, 2003-123982, and 2002-170684, EP 1211257, Japanese Patent Laid-Open Nos. 2002-226495, 2002-234894, 2001-247859, 2001-298470, 2002-173674, 2002-203678, 2002-203679, 2004-357791, 2006-256999, 2007-19462, 2007-

84635, and 2007-96259. Of these, more preferred as a light emitting dopant are Ir complexes, Pt complexes, Cu complexes, Re complexes, W complexes, Rh complexes, Ru complexes, Pd complexes, Os complexes, Eu complexes, Tb complexes, Gd complexes, Dy complexes, and Ce complexes, of which Ir complexes, Pt complexes, and Re complexes are especially preferred. Of these, Ir complexes, Pt complexes, and Re complexes each containing at least one coordination mode of a metal-carbon bond, a metal-nitrogen bond, a metal-oxygen bond, and a metal-sulfur bond are preferred. Furthermore, from the standpoint of emission efficiency, running durability, and chromaticity, Ir complexes, Pt complexes and Re complexes each containing a tridentate or higher-dentate ligand are especially preferred.

The content of the phosphorescent material in the light emitting layer is preferably 0.1 mass % or greater but not greater than 50 mass %, more preferably 0.2 mass % or greater but not greater than 50 mass %, still more preferably 0.3 mass % or greater but not greater than 40 mass %, most preferably 20 mass % or greater but not greater than 30 mass %, each based on the total mass of the light emitting layer.

—Hole Injection Layer, Hole Transport Layer—

A hole injection layer and a hole transport layer are layers having a function of receiving holes from an anode or anode side and transporting them to a cathode side.

—Electron Injection Layer, Electron Transport Layer—

An electron injection layer and an electron transport layer are layers having a function of receiving electrons from a cathode or a cathode side and transporting them to an anode side.

The description in the paragraphs from [0165] to [0167] of Japanese Patent Laid-Open No. 2008-270736 can be applied to the hole injection layer, hole transport layer, hole injection layer, and hole transport layer of the invention.

—Hole Blocking Layer—

The hole blocking layer is a layer having a function of preventing the holes, which have been transported from the anode side to the light emitting layer, from passing through to the cathode side. In the invention, the hole blocking layer can be provided as an organic layer adjacent to the light emitting layer on the cathode side.

Examples of organic compounds constituting the hole blocking layer include aluminum complexes such as aluminum (III) bis(2-methyl-8-quinolinato)-4-phenylphenolate (which will be abbreviated as BAlq), triazole derivatives, and phenanthroline derivatives such as 2,9-dimethyl-4,7-diphenyl-1,10-phenanthroline (which will be abbreviated as BCP).

The thickness of the hole blocking layer is preferably from 1 nm to 500 nm, more preferably from 5 nm to 200 nm, still more preferably from 10 nm to 100 nm.

The hole blocking layer may have a single layer structure composed of one or more of the above materials or may have a multilayer structure composed of two or more layers having the same composition or different compositions.

—Electron Blocking Layer—

The electron blocking layer is a layer having a function of preventing the electrons, which have been transported from the cathode side to the light emitting layer, from passing through to the anode side. In the invention, the electron blocking layer can be provided as an organic layer adjacent to the light emitting layer on the anode side.

As the organic compound constituting the electron blocking layer, the hole transport materials exemplified above can be used, for example.

The thickness of the electron blocking layer is preferably from 1 nm to 500 nm, more preferably from 5 nm to 200 nm, still more preferably from 10 nm to 100 nm.

The electron blocking layer may have a single layer structure composed of one or more of the above materials or may be a multilayer structure composed of two or more layers having the same composition or different compositions.

<Protective Layer>

The organic EL device may be entirely protected with a protective layer.

The description in the paragraphs from [0169] to [0170] of Japanese Patent Laid-Open No. 2008-270736 can be applied to the protective layer of the invention.

<Sealing Container>

The organic EL device may be entirely sealed with a sealing container.

The description in the paragraph [0171] of Japanese Patent Laid-Open No. 2008-270736 can be applied to the sealing container of the invention.

[Manufacturing Method of Organic Electroluminescence Device]

The manufacturing method of the organic electroluminescence device of the invention is characterized by that the organic electroluminescence device is manufactured by using an iridium complex selected by using the material selecting method.

[Sublimation Purification]

The iridium complex selected by using the material selecting method is purified by sublimation and then used for the manufacture of an organic electroluminescence device. Another compound to be used for each organic layer of the organic electroluminescence device is also preferably purified by sublimation.

As the sublimation purification method, conventionally known methods can be employed.

[Film Formation Method]

An organic electroluminescence device can be manufactured by forming respective compounds, which have been purified by sublimation, into films successively on a substrate and thus forming organic layers.

The organic layer of the organic electroluminescence device can be formed by any of dry film formation processes such as vapor deposition and sputtering or wet film formation processes (wet processes) such as transfer process, printing process, and spin coating.

The heating temperature is preferably from 200° C. to 400° C., more preferably from 250° C. to 320° C.

Heating time is preferably from 0.1 hour to 350 hours, more preferably from 0.1 hour to 150 hours.

(Drive)

By applying a DC (if necessary, may contain an AC component) voltage (generally from 2 volts to 15 volts) or a DC current between the anode and the cathode, the organic electroluminescence device can be caused to emit light.

For driving of the organic electroluminescence device, the driving methods described in Japanese Patent Laid-Open Nos. 148687/1990, 301355/1994, 29080/1993, 134558/1995, 234685/1996, and 241047/1996, Japanese Patent No. 2784615, and U.S. Pat. Nos. 5,828,429 and 6,023,308 can be employed.

The luminescence device of the invention can have an improved light collection efficiency by various known contrivances. For example, the luminescence device of the invention can have an improved light collection efficiency and an improved external quantum efficiency by processing the shape of the substrate surface (for example, by forming a minute rugged pattern), by controlling the refractive indices of the substrate, an ITO layer, and the organic layer, or by controlling the thicknesses of the substrate, ITO layer and organic layer.

The luminescence device may employ a so-called top emission system in which light is collected from the anode side.

The organic EL device of the invention may have a resonator structure. For example, the organic EL device may be a device obtained by stacking, on a transparent substrate, a multilayer-film mirror composed of two or more films with different refractive indices, a transparent or translucent electrode, a light emitting layer, and a metal electrode one after another. Light generated in the light emitting layer repeats reflection between the multilayer-film mirror and the metal electrode, which serve as reflector plates, to cause resonance.

In another preferred embodiment, a transparent or translucent electrode and a metal electrode on a transparent substrate function as reflector plates, respectively, and light generated in the light emitting layer repeats reflection to cause resonance.

In order to form the resonant structure, effective refractive indices of two reflector plates and an optical path length determined by the refractive index and the thickness of the respective layer(s) provided between the reflector plates are adjusted to be optimum values for achieving a desired resonant wavelength. A calculation formula in the first aspect is described in Japanese Patent Laid-Open No. 180883/1997, while a calculation formula in the second aspect is described in Japanese Patent Laid-Open No. 2004-127795.

(Intended Use of Luminescence Device)

The luminescence device can be suitably utilized for light emission apparatuses, pixels, display devices, displays, backlights, electrophotography, illumination light sources, recording light sources, exposure light sources, read light sources, markers, signboards, interiors, optical communications and so on. In particular, the device can be used preferably for apparatuses to be driven in a region having a high luminous brightness such as illumination apparatuses and display apparatuses.

EXAMPLES

The present invention will hereinafter be described in further detail by Examples. It should however be borne in mind that the scope of the invention is not limited by the following specific examples.

[Synthesis of Iridium Complex]

Synthesis of Compound (1)-2

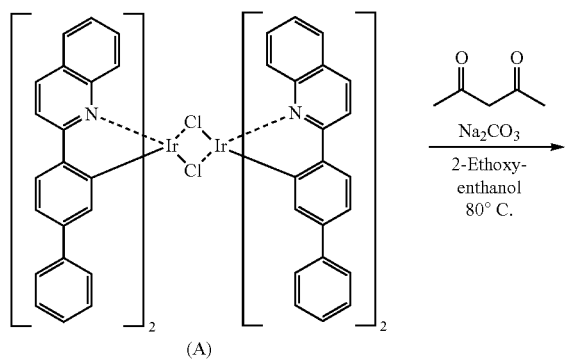

(A)

-continued

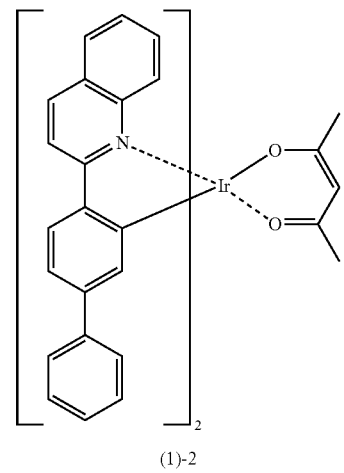

(1)-2

Figure 4:
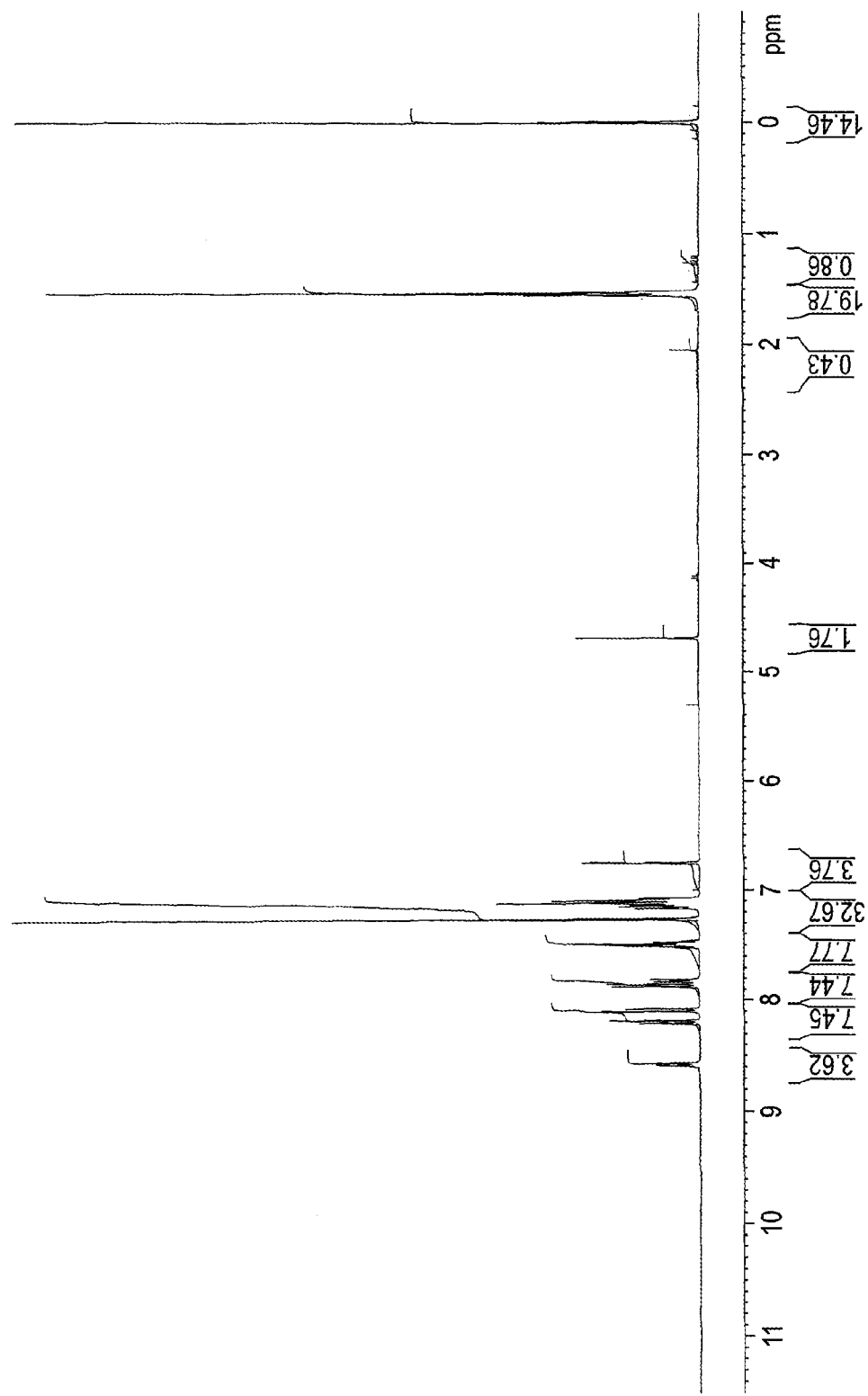
FIG. 4 shows a 300 MHz $^1$H-NMR (in CDCl$_3$) spectrum of Compound (1)-2.
Figure 5:
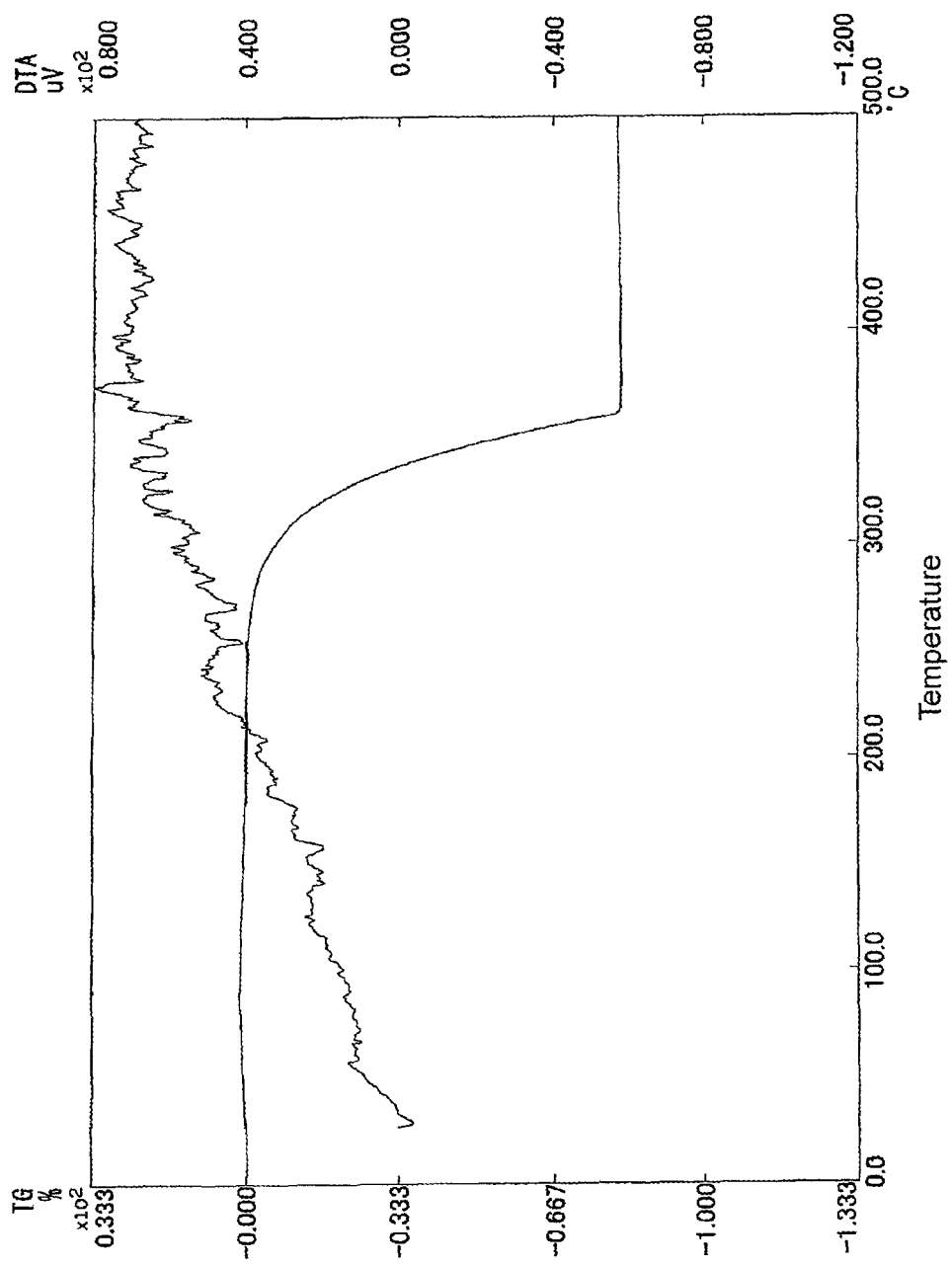
FIG. 5 shows a TG/DTA curve of Compound (1)-2 under vacuum.

A 300-ml three-necked flask was charged with 2.0 g of Compound (A), 38.4 ml of 2-ethoxyethanol, 1.34 g of $Na_2CO_3$, and 0.40 ml of acetylacetone. The resulting mixture was heated to 80° C. while stirring in a nitrogen atmosphere. Four hours later, the reaction mixture was cooled to room temperature and then 80 ml of water was added. The resulting mixture was stirred for 30 minutes. The precipitate thus formed was then filtered and washed with water, 2-propanol, and hexane. The crystals thus obtained were charged in a 200-ml eggplant flask, to which 100 ml of water was added. The resulting mixture was stirred at room temperature for one hour. The crystals obtained by filtration were dried to yield 1.88 g of red crystals. After 1.5 g of the crystals were charged in a 200-ml eggplant flask and 100 ml of THF was added, the resulting mixture was stirred. The insoluble component was filtered and dried to yield 0.79 g of red crystals. To 0.5 g of the red crystals weighed was added 25 ml of methylene chloride to dissolve the former in the latter and the resulting solution was purified by open silica gel column chromatography using methylene chloride as an eluent. The fraction thus obtained was concentrated. The precipitate formed by adding methanol to the concentrate was filtered and dried to obtain Compound (1)-2 in the form of deep red crystals. The identification of the compound was performed by 300 MHz $^1$H-NMR (in $CDCl_3$). The 300 MHz $^1$H-NMR (in $CDCl_3$) spectrum of Compound (1)-2 is shown in FIG. 4.

Sublimation purification was carried out by using "TRS-1" (trade name; product of ULVAC-RIKO, Inc), reducing the pressure to $7.0 \times 10^{-2}$ Pa, and increasing the temperature to 330° C. The red crystals attached to the glass tube were collected with a spatula. The resulting sublimation purification product was designated as Compound (1)-1.

Synthesis of Compound (1)-3

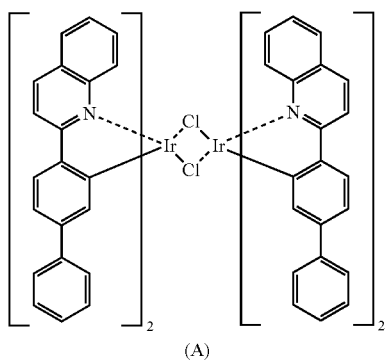
(A)

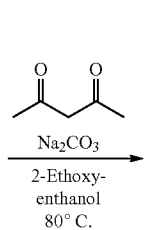

Na₂CO₃

2-Ethoxy-
enthanol
80° C.

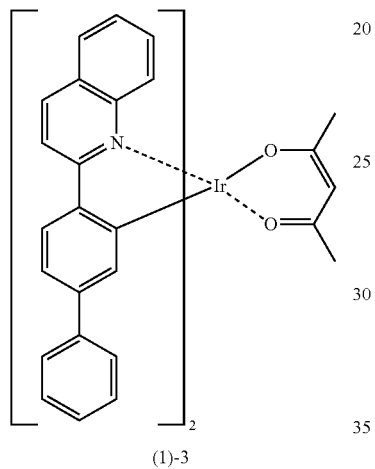
(1)-3

A 200-ml three-necked flask was charged with 4.0 g of Compound (A), 77 ml of 2-ethoxyethanol, 2.7 g of Na₂CO₃, and 0.80 ml of acetylacetone. The resulting mixture was heated to 80° C. while stirring in a nitrogen atmosphere. Two hours later, the reaction mixture was cooled to room temperature. After the reaction mixture was allowed to stand for one day, 50 ml of water was added. The resulting mixture was stirred for 15 minutes. The precipitate thus formed was then filtered and washed with water. The crystals were taken out and charged in a 300-ml eggplant flask, to which 150 ml of water was added. After stirring for 15 minutes, the reaction mixture was filtered. Crystals thus obtained were washed with water, 2-propanol, and hexane and then, dried to yield 3.91 g of dark red crystals. After 3.0 g of the crystals were charged in a 300-ml eggplant flask and 150 ml of methylene chloride was added to dissolve the crystals therein. The black insoluble component was removed by filtration and the filtrate was concentrated to 20 ml. The red solution thus obtained was purified by silica gel column chromatography using methylene chloride. After the red solution thus obtained was concentrated to 20 ml, 100 ml of methanol was added. The purified crystals were taken out by filtration and dried to yield 2.4 g of Compound (1)-3 in the form of red crystals.

Sublimation purification was carried out by using "TRS-1" (trade name; product of ULVAC-RIKO, Inc), reducing the pressure to $7.0 \times 10^{-2}$ Pa, and increasing the temperature to 325° C. The red crystals attached to the glass tube were collected with a spatula.

Synthesis of Compound (1)-4

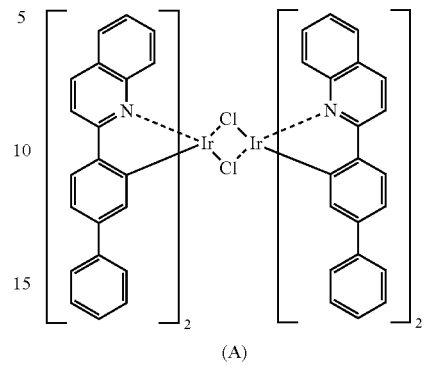
(A)

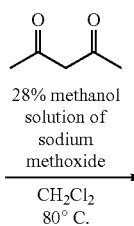

28% methanol
solution of
sodium
methoxide

CH₂Cl₂
80° C.

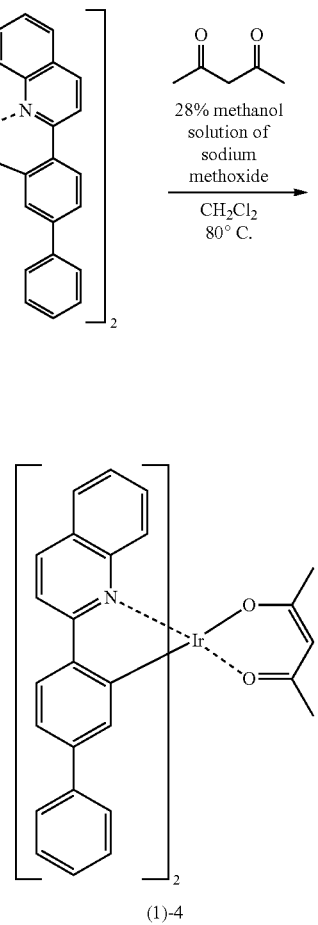
(1)-4

A 500-ml three-necked flask was charged with 5.0 g of Compound (A), 100 ml of CH₂Cl₂, 3.3 ml of acetylacetone, and 6.11 g of a 28% methanol solution of sodium methoxide. The resulting mixture was heated to 50° C. while stirring in a nitrogen atmosphere. Three hours later, the reaction mixture was cooled to room temperature. Water and hexane were added, followed by filtration. The filtrate was transferred to a separatory funnel and a separating operation was performed by adding ethyl acetate to the filtrate. After removal of the aqueous layer, water was added to the remaining organic layer. The mixture was shaken up for washing. Then, washing was conducted twice with a saturated aqueous solution of sodium chloride. The aqueous layers were taken out, combined, and then transferred to a separatory funnel. CH₂Cl₂ was added to the funnel and back extraction was performed. The organic layers thus obtained were combined, dried over sodium sulfate, and then filtered. The filtrate was concentrated to obtain 4 g of Compound (1)-4 in the form of red crystals.

Sublimation purification was carried out by using "TRS-1" (trade name; product of ULVAC-RIKO, Inc), reducing the pressure to $7.0 \times 10^{-2}$ Pa, and increasing the temperature to 325° C. The red crystals attached to the glass tube were collected with a spatula.

Synthesis of Compound (2)=TM-51

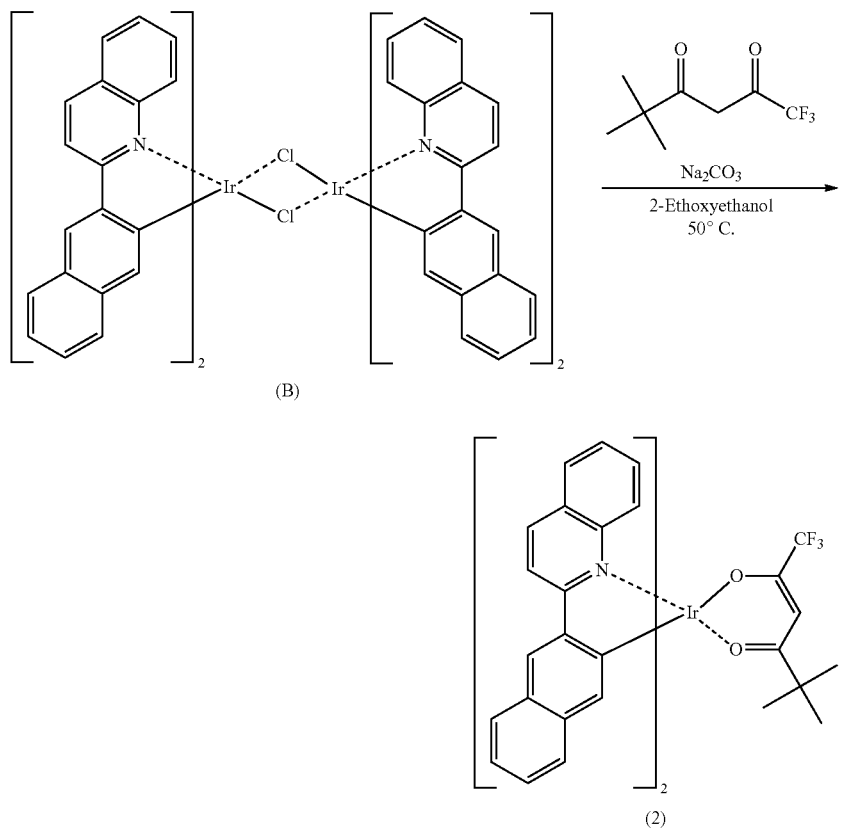

Figure 11:
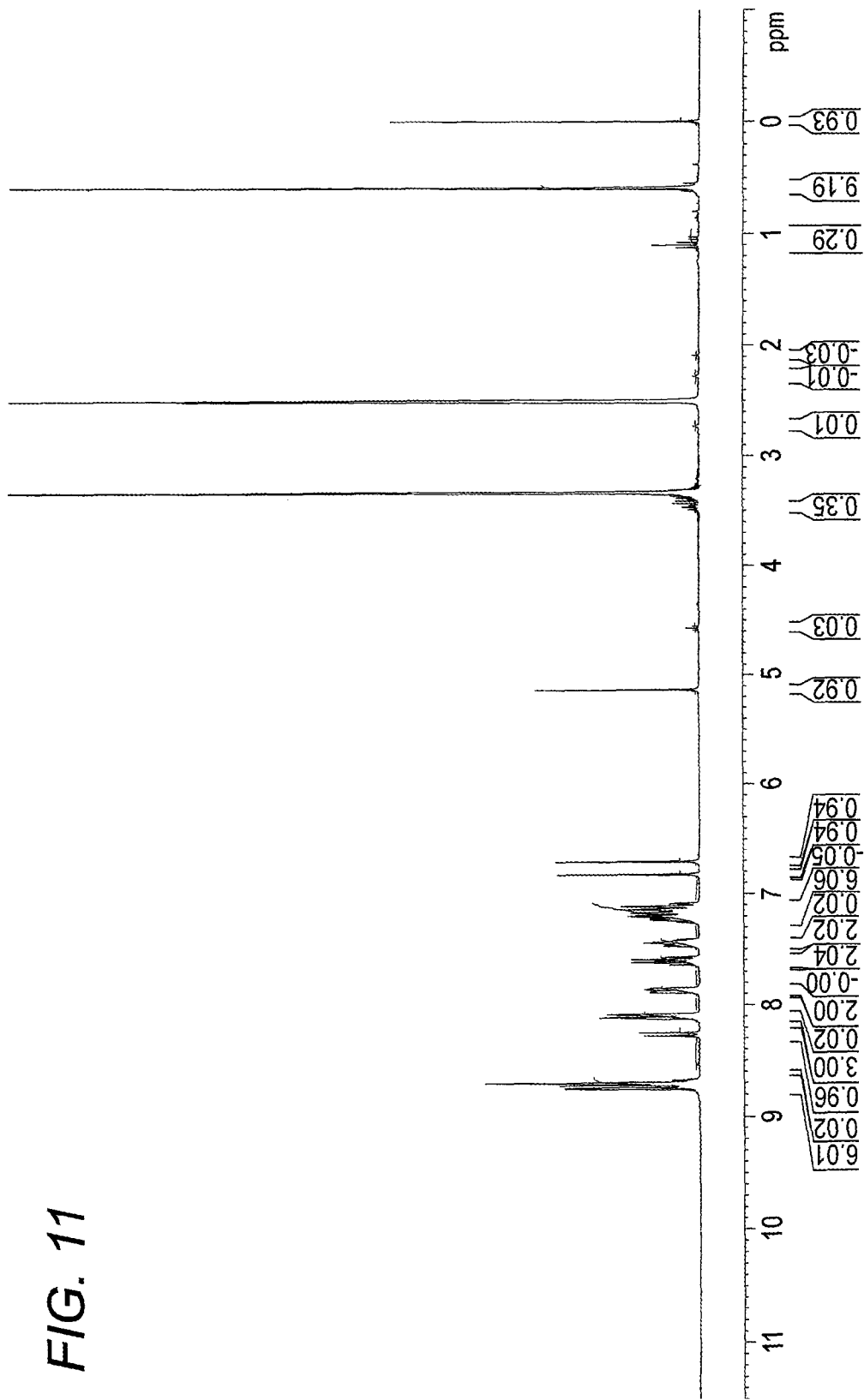
FIG. 11 shows a $^1$H-NMR (in d$_6$-DMSO) spectrum of Compound (2)
Figure 12:
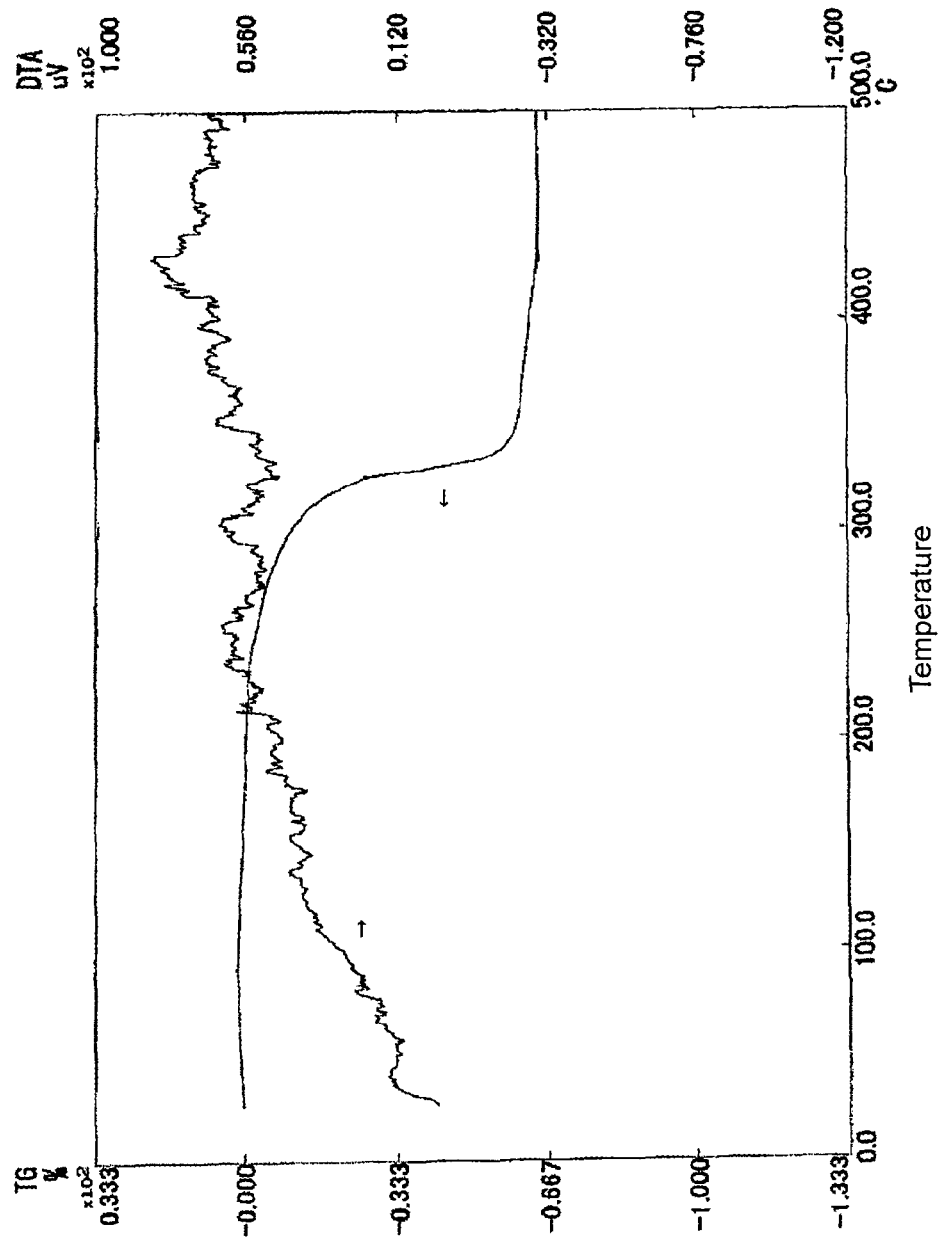
FIG. 12 shows a TG/DTA curve of Compound (2) under vacuum.

A 100-ml three-necked flask was charged with 0.8 g of Compound (B), 33 ml of 2-ethoxyethanol, and 0.58 g of Na$_2$CO$_3$. After addition of 0.17 ml of 1,1,1-trifluoro-5,5-dimethyl-2,4-hexanedione, the resulting mixture was heated to 50° C. while stirring in a nitrogen atmosphere. Twenty minutes later, 0.3 ml of 1,1,1-trifluoro-5,5-dimethyl-2,4-hexanedione was added further. After stirring for further one hour, the reaction mixture was cooled to room temperature. Water (65 ml) was added to the cooled reaction mixture, followed by stirring for 3 minutes. The crystals obtained by filtering the reaction mixture were washed successively with water, 2-propanol, and hexane and dried to yield 0.89 g of Compound (2). The identification of the compound was performed by $^1$H-NMR (in d$_6$-DMSO). The $^1$H-NMR (in d$_6$-DMSO) spectrum of Compound (2) is shown in FIG. 11

Sublimation purification was carried out by using "TRS-1" (trade name; product of ULVAC-RIKO, Inc), reducing the pressure to $7.0 \times 10^{-2}$ Pa, and increasing the temperature to 320° C. The red crystals attached to the glass tube were collected with a spatula.

Synthesis of Compound (3)=TM-50

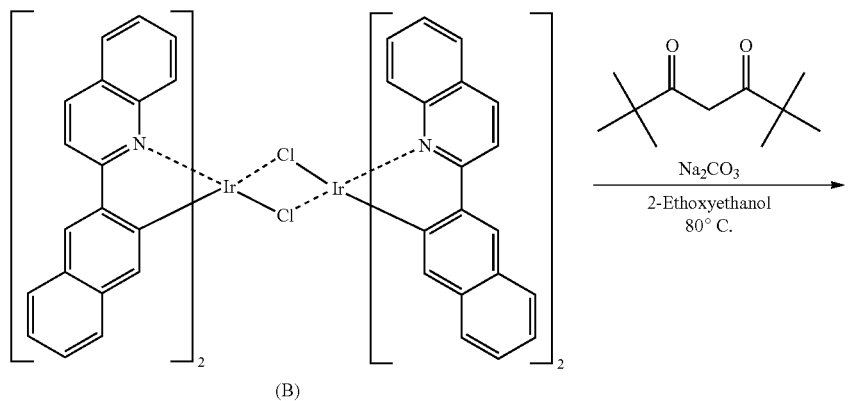

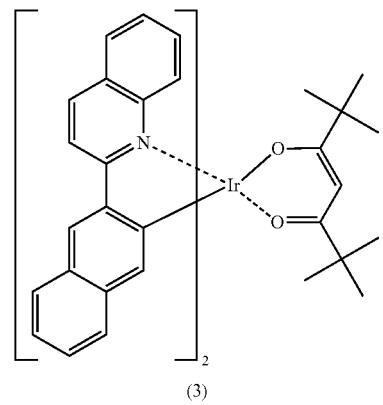

(3)

Figure 16:
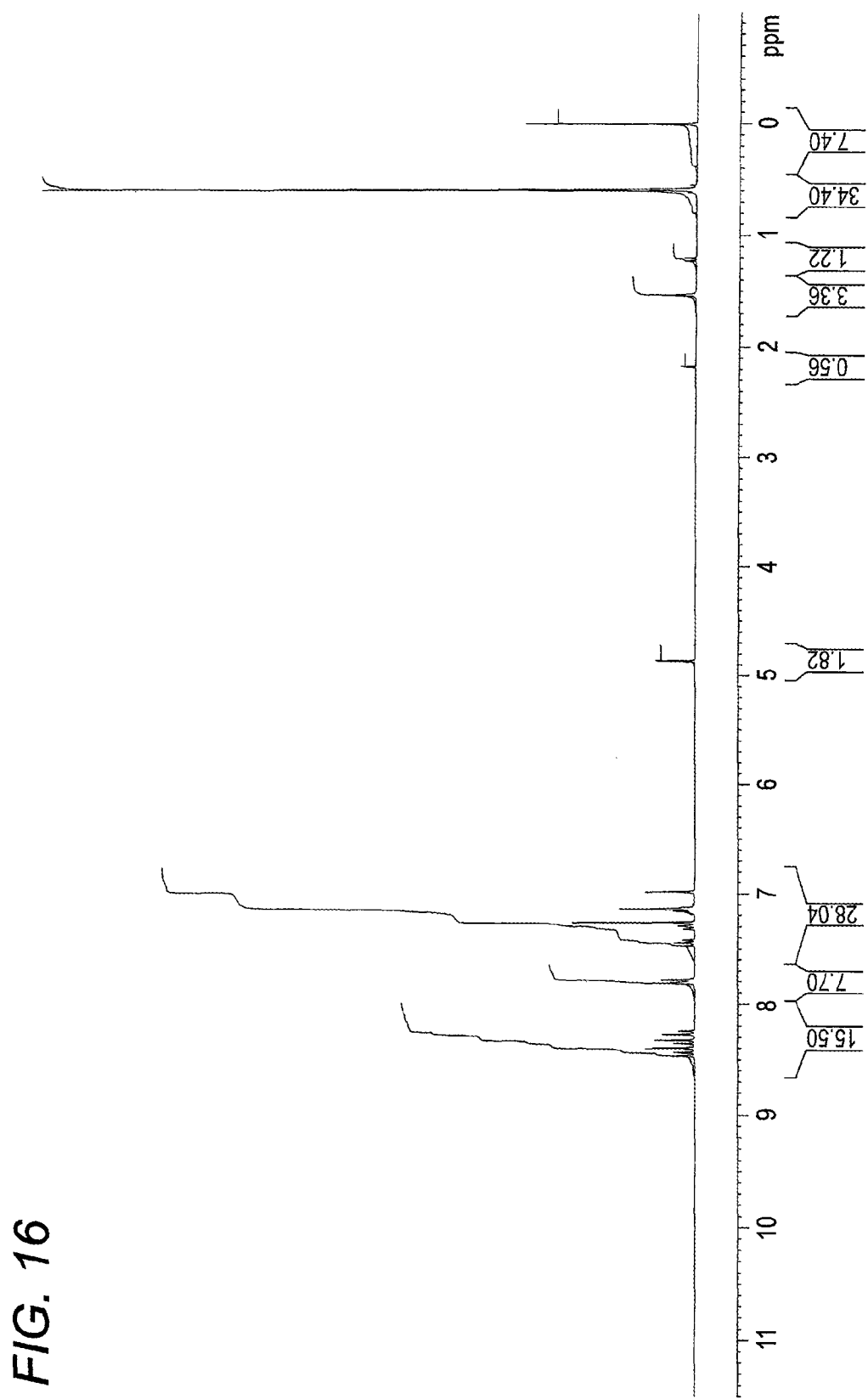
FIG. 16 shows a 300 MHz $^1$H-NMR (in CDCl$_3$) spectrum of Compound (3)

After a 100-ml three-necked flask was charged with 0.5 g of Compound (B), 10.3 ml of 2-ethoxyethanol, and 0.28 ml of dipivaloylmethane, 360 mg of $Na_2CO_3$ was added. The resulting mixture was heated under reflux while stirring in a nitrogen atmosphere. Two hours later, the reaction mixture was cooled to room temperature. Water (250 ml) was added and the mixture was stirred for 10 minutes. The crystals obtained by filtering the reaction mixture were washed successively with water, ethanol and hexane and dried to yield 0.46 g of dark red crystals. The resulting crystals (0.4 g) was transferred to a 100-ml eggplant flask and after addition of 50 ml of 2-propanol, the mixture was washed under boiling. After cooling to room temperature, the reaction mixture was filtered. The crystals were taken out, washed with 3 ml of 2-propanol, and dried to yield 316 mg of Compound (3) in the form of red crystals. The identification of the compound was performed by 300 MHz $^1$H-NMR (in $CDCl_3$). The 300 MHz $^1$H-NMR (in $CDCl_3$) spectrum of Compound (3) is shown in FIG. 16

Sublimation purification was carried out by using "TRS-1" (trade name; product of ULVAC-RIKO, Inc), reducing the pressure to $7.0 \times 10^{-2}$ Pa, and increasing the temperature to 310° C. The red crystals attached to the glass tube were collected with a spatula.

Synthesis of Compound (4)=TM-48

Figure 17:
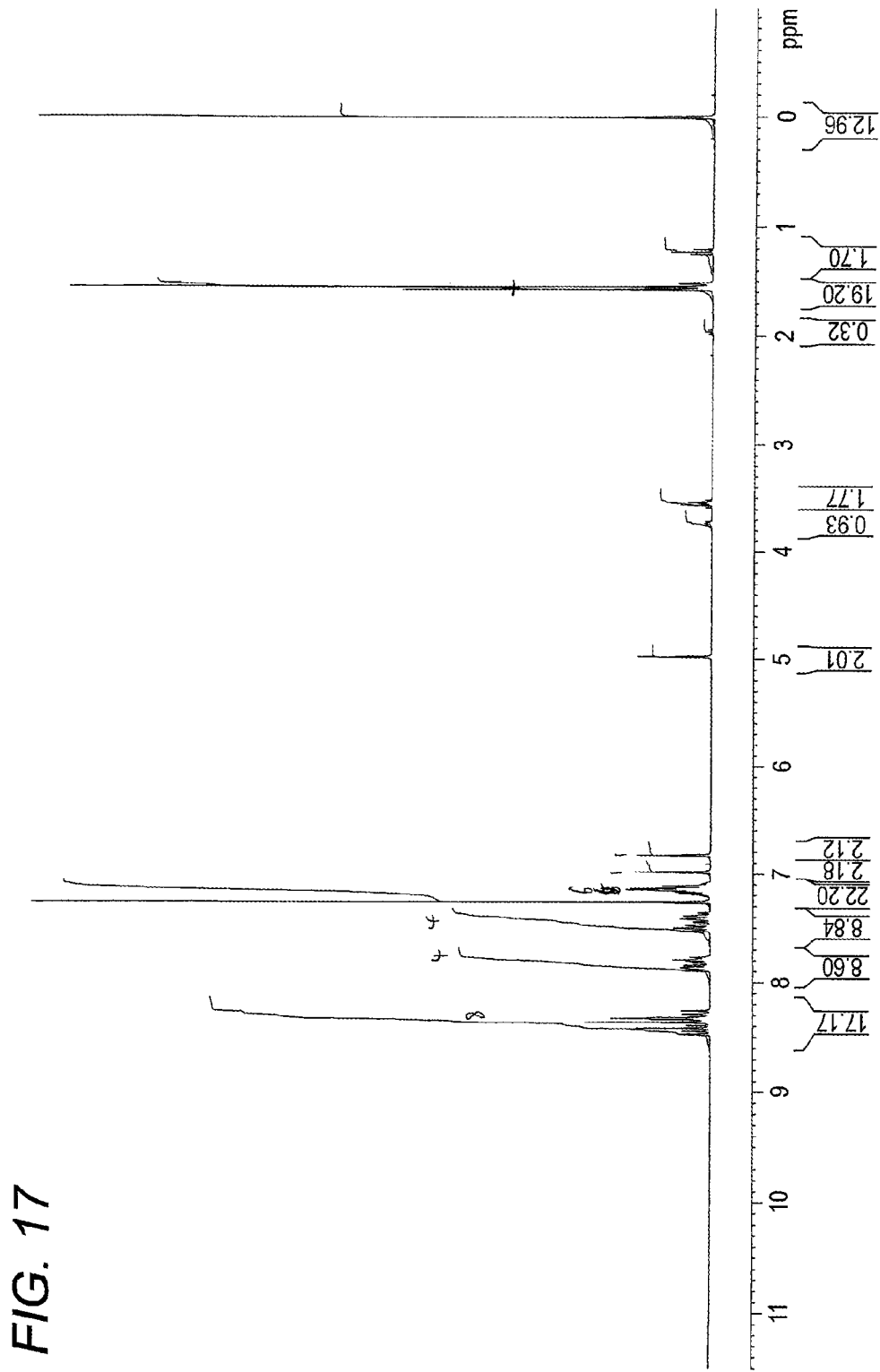
FIG. 17 shows a 300 MHz $^1$H-NMR (in CDCl$_3$) spectrum of Compound (4)
Figure 18:
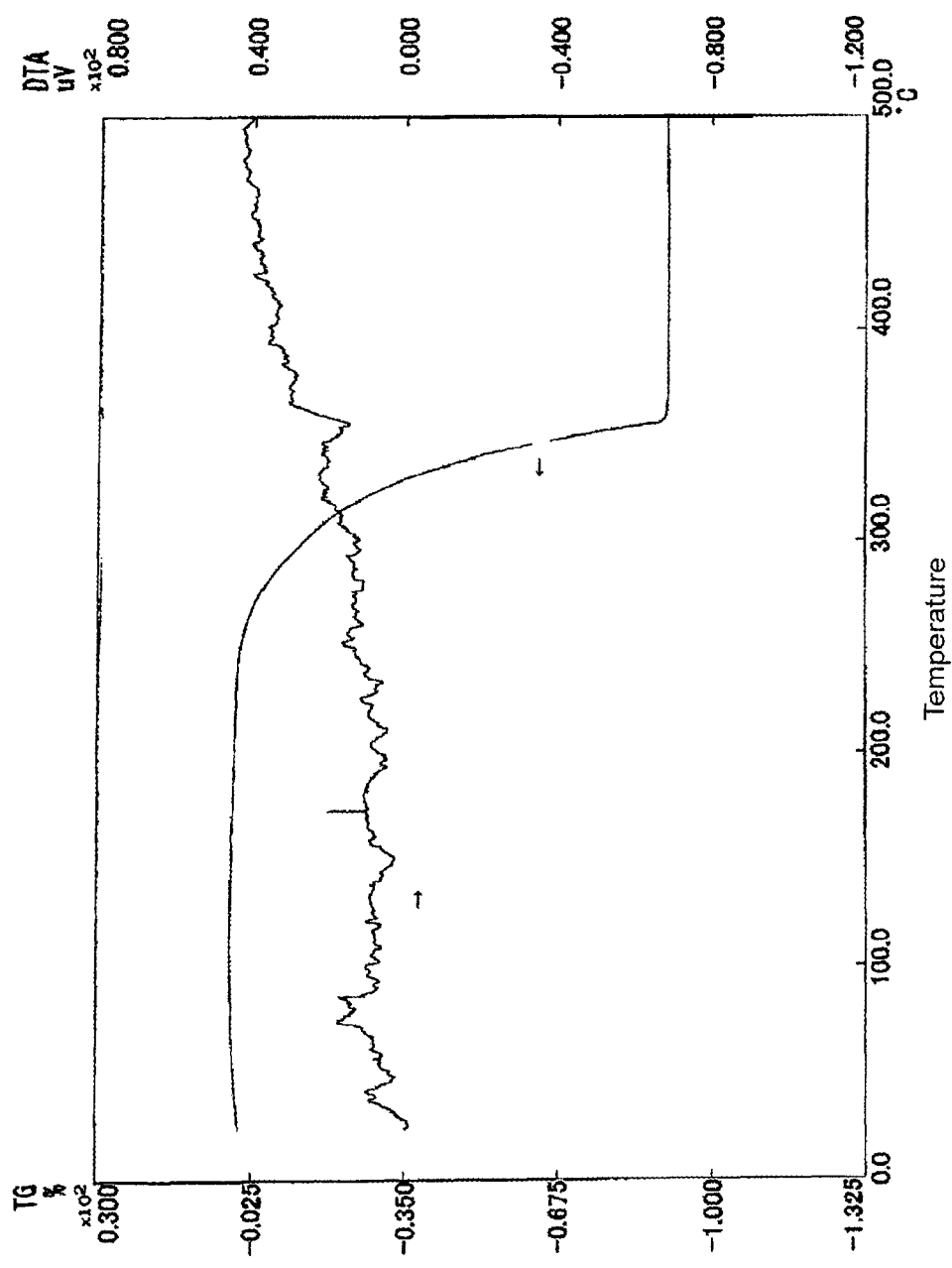
FIG. 18 shows a TG/DTA curve of Compound (4) under vacuum.

After a 100-ml three-necked flask was charged with 300 mg of Compound (B), 6 ml of 2-ethoxyethanol, and 0.17 ml of 1,1,1-trifluoro-2,4-pentanedione, 215 mg of $Na_2CO_3$ was added. The resulting mixture was heated under reflux while stirring in a nitrogen atmosphere. One hour and a half later, the reaction mixture was cooled to room temperature. Water (80 ml) was added and the mixture was stirred for 20 minutes. The crystals obtained by filtering the reaction mixture were washed successively with water, 2-propanol and hexane and dried to yield 0.22 g of Compound (4) in the form of red crystals. The identification of the compound was performed by 300 MHz $^1$H-NMR (in $CDCl_3$). The 300 MHz $^1$H-NMR (in $CDCl_3$) spectrum of Compound (4) is shown in FIG. 17.

Sublimation purification was carried out by using "TRS-1" (trade name; product of ULVAC-RIKO, Inc), reducing the pressure to $7.0 \times 10^{-2}$ Pa, and increasing the temperature to 340° C. The red crystals attached to the glass tube were collected with a spatula.

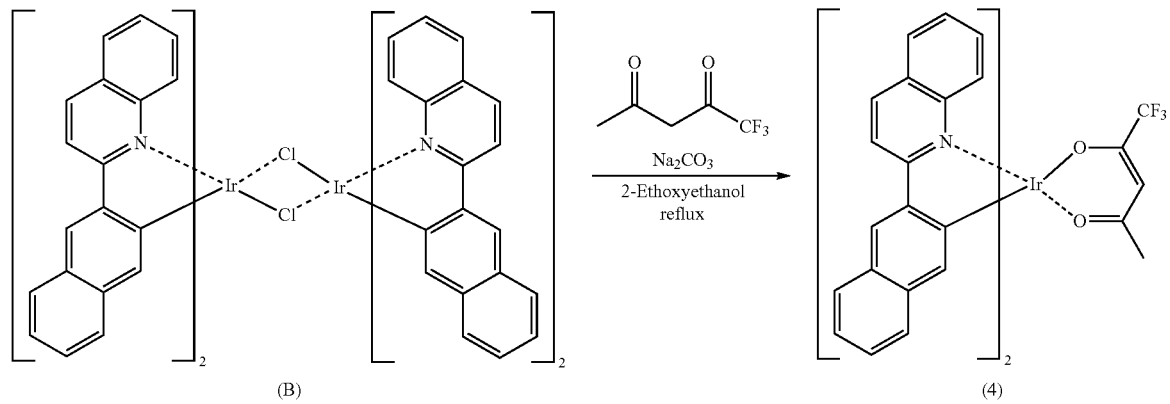

(B)     (4)

Synthesis of Compound (5)=TM-49

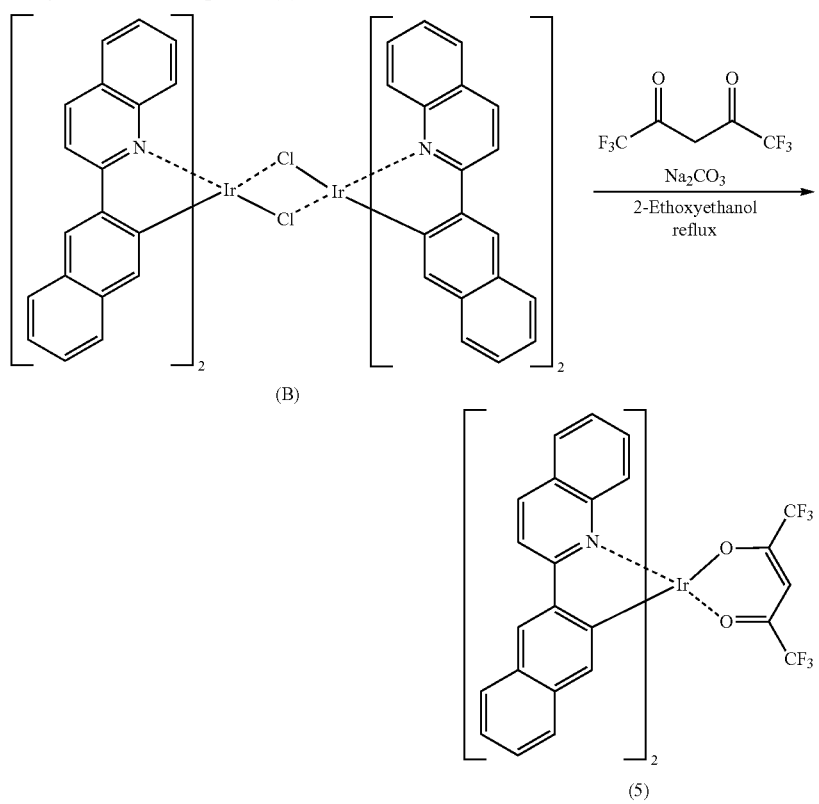

Figure 20:
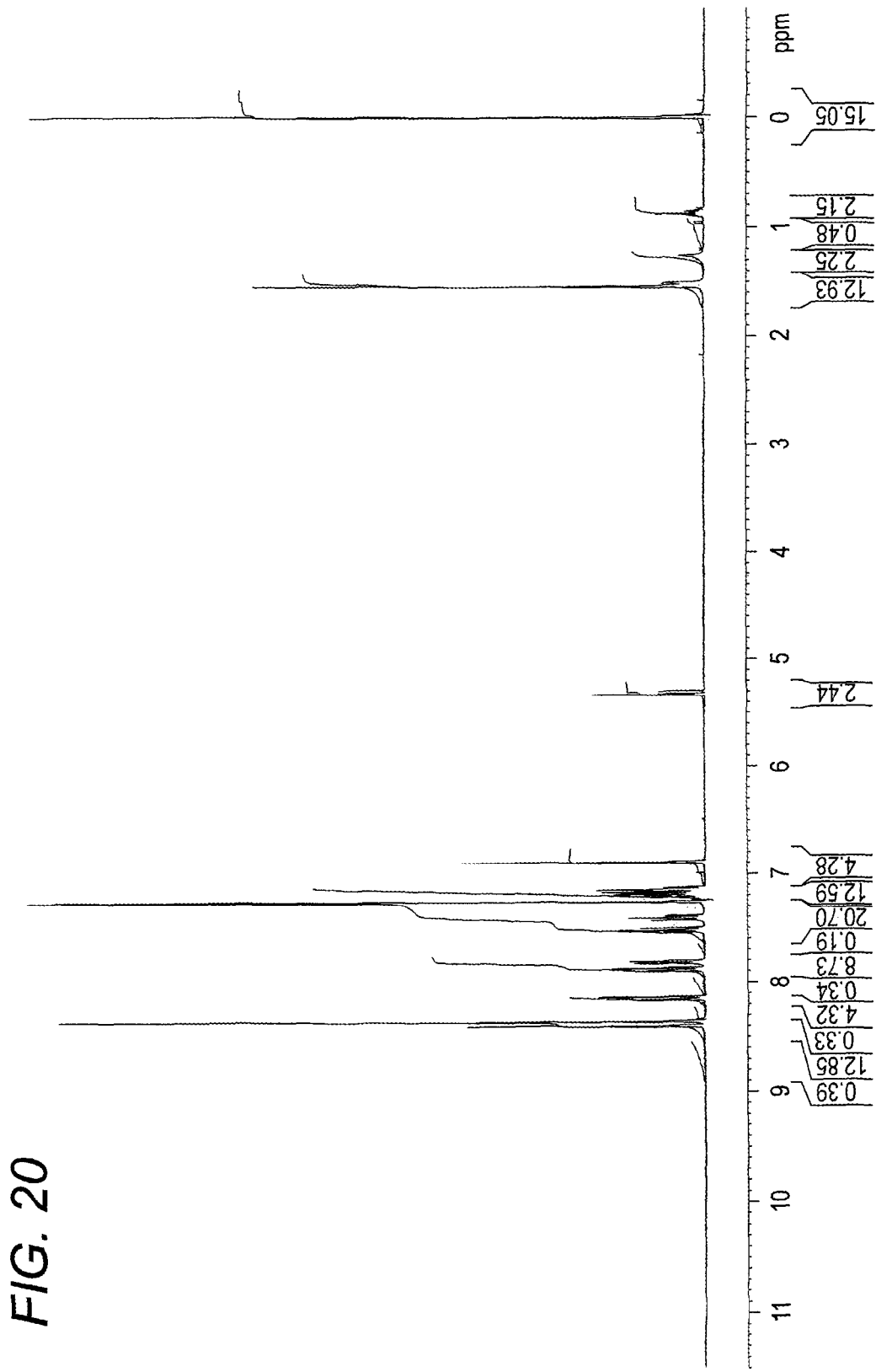
FIG. 20 shows a 300 MHz $^1$H-NMR (in CDCl$_3$) spectrum of Compound (5)
Figure 21:
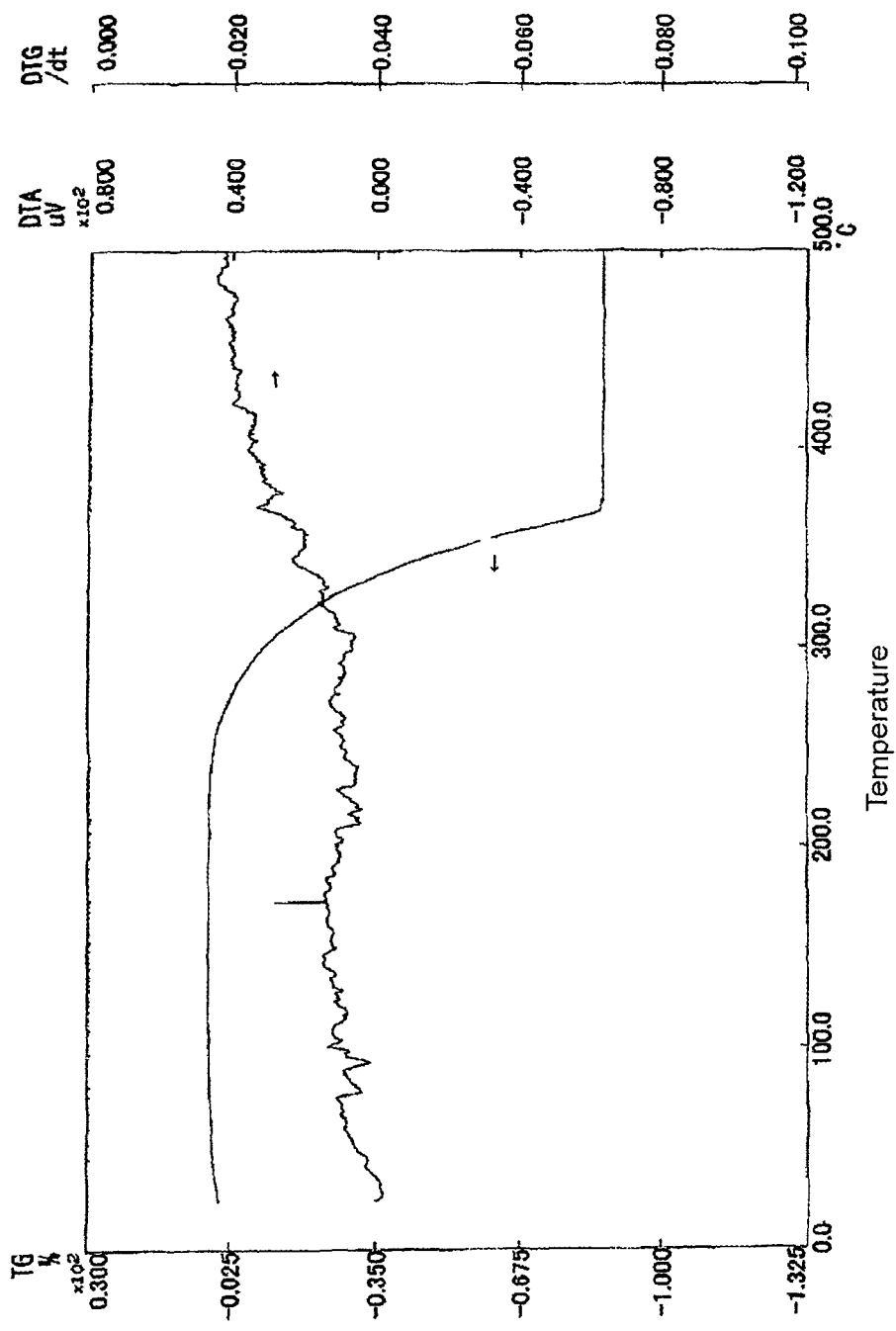
FIG. 21 shows a TG/DTA curve of Compound (5) under vacuum.

After a 100-ml three-necked flask was charged with 1.0 g of Compound (B), 20.6 ml of 2-ethoxyethanol, and 0.29 ml of 1,1,1,5,5,5-hexafluoro-2,4-pentanedione, 719 mg of $Na_2CO_3$ was added. The resulting mixture was heated under reflux while stirring in a nitrogen atmosphere. Eight hours later, the reaction mixture was cooled to room temperature. The crystals obtained by filtering the reaction mixture were washed successively with water, 2-propanol, and hexane to yield 1.00 g of red crystals. The resulting crystals were transferred to a 200-ml eggplant flask and after addition of 100 ml of 2-propanol, the resulting mixture was washed under boiling and dried to yield 0.88 g of red crystals. 0.65 g of the resulting crystals were weighed and purified by short column purification using methylene chloride. Hexane was added to the resulting red solution. The precipitate thus formed was filtered, taken out, and dried to yield 0.46 g of Compound (5) in the form of reddish brown crystals. The identification of the compound was performed by 300 MHz $^1$H-NMR (in $CDCl_3$). The 300 MHz $^1$H-NMR (in $CDCl_3$) spectrum of Compound (5) is shown in FIG. 20.

Sublimation purification was carried out by using "TRS-1" (trade name; product of ULVAC-RIKO, Inc), reducing the pressure to $7.0\times10^{-2}$ Pa and increasing the temperature to 330° C. The red crystals attached to the glass tube were collected with a spatula.

<Synthesis of Comparative Compounds>
Synthesis of Compound (1)-5

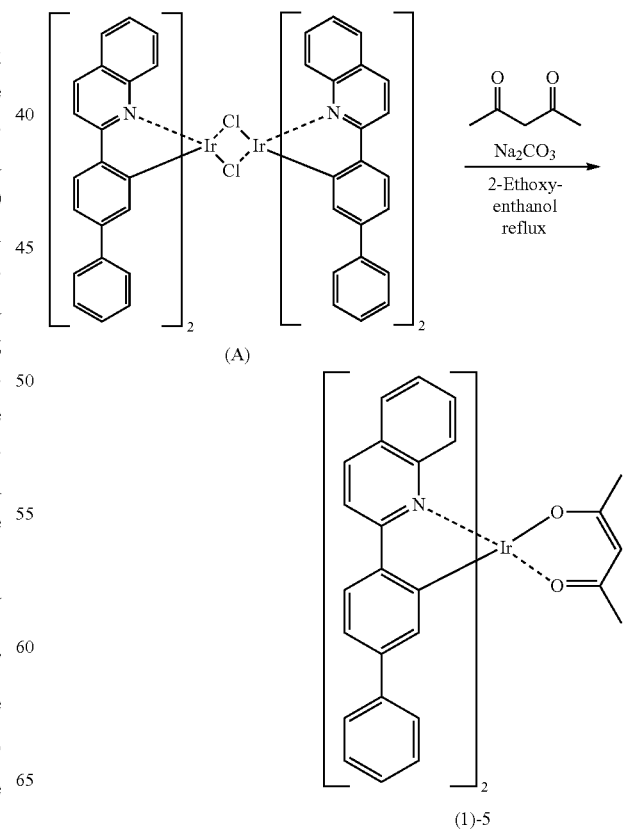

A 100-ml three-necked flask was charged with 1.0 g of Compound (A), 19.2 ml of 2-ethoxyethanol, 672 mg of $Na_2CO_3$, and 0.36 ml of acetylacetone. The resulting mixture was heated under reflux while stirring in a nitrogen atmosphere. Two hours later, the reaction mixture was cooled to room temperature. Water (50 ml) was added and stirring was performed for further 10 minutes. Then, the precipitate thus formed was filtered, washed with water, 2-propanol, and hexane to yield dark red crystals. The crystals were charged in a 100-ml eggplant flask, to which 50 ml of 2-propanol was added, followed by washing under boiling. The reaction mixture was cooled to room temperature and then filtered. The crystals thus obtained were washed with 2-propanol and hexane to yield 0.60 g of Compound (1)-5 in the form of dark red crystals.

Sublimation purification was carried out by using "TRS-1" (trade name; product of ULVAC-RIKO, Inc), reducing the pressure to $7.0\times10^{-2}$ Pa and increasing the temperature to 325° C. The crystals attached to the glass tube were collected with a spatula.

Synthesis of Compound (1)-6

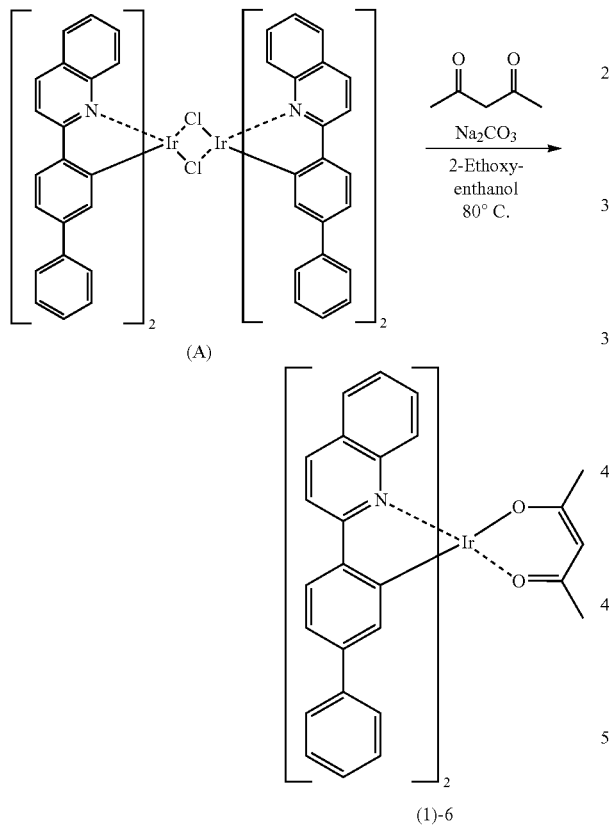

(1)-6

A 100-ml three-necked flask was charged with 1.5 g of Compound (A), 29 ml of 2-ethoxyethanol, 1.0 g of $Na_2CO_3$, and 0.30 ml of acetylacetone. The resulting mixture was heated to 50° C. while stirring in a nitrogen atmosphere. Three hours later, the reaction mixture was cooled to room temperature. After the reaction mixture was allowed to stand for 2 days, 0.15 ml of acetylacetone was added. The resulting mixture was heated to 50° C. while stirring in a nitrogen atmosphere. Seven hours later, the reaction mixture was cooled to room temperature. Water (50 ml) was added and stirring was performed for 3 minutes. Then, the precipitate thus formed was filtered, washed with water, 2-propanol, and hexane to yield dark red crystals. The crystals were charged in a 100-ml eggplant flask, to which 50 ml of 2-propanol was added, followed by stirring under heating at 50° C. The reaction mixture was cooled to room temperature and then filtered. The crystals thus obtained were washed with 2-propanol and hexane. The dark red crystals thus obtained were vacuum dried to yield 0.60 g of Compound (1)-6.

Sublimation purification was carried out by using "TRS-1" (trade name; product of ULVAC-RIKO, Inc), reducing the pressure to $7.0\times10^{-2}$ Pa, and increasing the temperature to 325° C. The red crystals attached to the glass tube were collected with a spatula.

Synthesis of Compound (1)-7

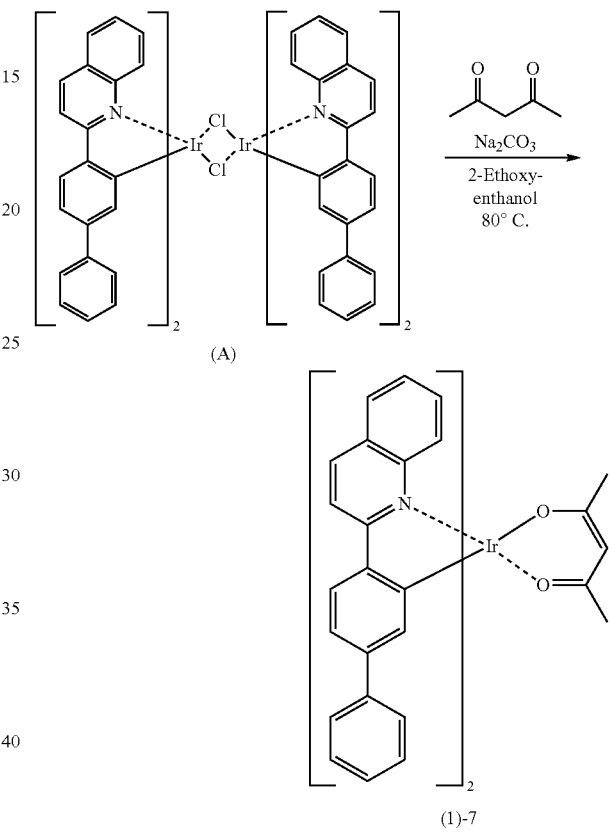

(1)-7

A 200-ml three-necked flask was charged with 5.0 g of Compound (A), 29 ml of 2-ethoxyethanol, 1.01 g of $Na_2CO_3$, and 0.30 ml of acetylacetone. The resulting mixture was heated to 50° C. while stirring in a nitrogen atmosphere. Five hours later, the reaction mixture was cooled to room temperature. After the reaction mixture was allowed to stand for 2 days, 0.15 ml of acetylacetone was added. The resulting mixture was heated to 50° C. in a nitrogen atmosphere and stirred for seven hours. The reaction mixture was cooled to room temperature. Water (50 ml) was added and stirring was performed for 3 minutes. Then, the precipitate thus formed was filtered, washed with water, 2-propanol, and hexane. The crystals thus obtained were charged in a 200-ml eggplant flask, to which 50 ml of 2-propanol was added. The resulting mixture was heated to 50° C. and stirred for 4 hours. The reaction mixture was cooled to room temperature and then filtered. The crystals thus obtained were washed with 2-propanol and hexane and dried to yield 1.28 g of Compound (1)-7.

Sublimation purification was carried out by using "TRS-1" (trade name; product of ULVAC-RIKO, Inc), reducing the pressure to $7.0\times10^{-2}$ Pa and increasing the temperature to 325° C. The red crystals attached to the glass tube were collected with a spatula.

Synthesis of Compound (6)

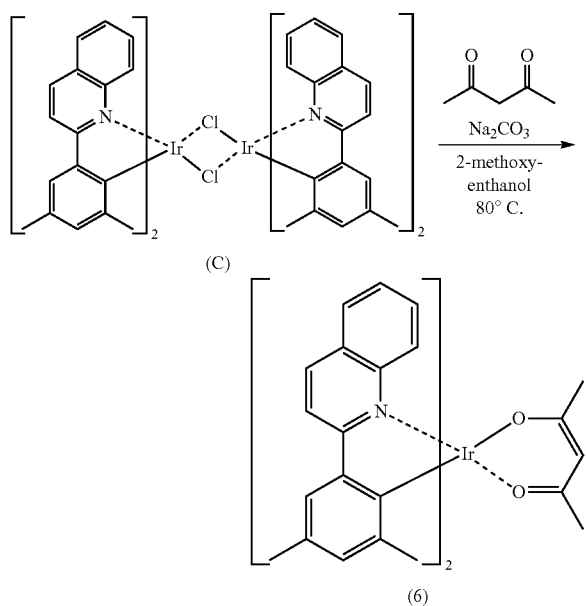

A 100-ml eggplant flask was charged with 0.5 g of Compound (C), 1 ml of acetylacetone, and 10 ml of 2-methoxyethanol. Sodium carbonate (0.5 g) was added to the resulting mixture while stirring. After the reaction mixture was heated under reflux for 2 hours, it was returned to room temperature. Distilled water was then added. The precipitate thus obtained was filtered and washed with distilled water to yield a red precipitate. The precipitate was dissolved in toluene. The resulting solution was subjected to silica gel column chromatography with hexane as an eluent and purified while changing the mixing ratio of the eluent gradually to hexane/ethyl acetate=50/1 and then, to 10/1. The red solution thus obtained was concentrated under reduced pressure, followed by the addition of ethyl acetate and hexane to yield 0.3 g of Compound (6).

Sublimation purification was carried out by using "TRS-1" (trade name; product of ULVAC-RIKO, Inc), reducing the pressure to $7.0 \times 10^{-2}$ Pa and increasing the temperature to 260° C. The red crystals attached to the glass tube were collected with a spatula.

A gradual endothermic change was observed from the illustrated TG/DTA curve of Compound (6) under ordinary pressure in a range of from 280 to 330° C. at around a rate of weight loss of 5 mass %.

[TG/DTA Measurement Under Vacuum]

The compounds obtained in Examples 1 to 8 and Comparative Examples 1 to 3 were each measured for evaporate rate. The measurement was performed by using "VAP-9000" (trade name; product of ULVAC-RIKO, Inc) at a heating rate of 2° C./min in a range of from 30 to 500° C. under vacuum. The temperature control was started after confirming that the degree of vacuum became $1.0 \times 10^{-2}$ Pa. A rate of weight loss was determined from the remaining amount of the compound when the temperature was raised to 500° C.

The TG/DTA curves of Compounds (1)-1, (1)-2, (1)-3, (1)-4, (2), (3), (4), (5), (1)-5, (1)-6, (1)-7, and (6) under vacuum are shown in FIGS. 2, 5, 7, 9, 12, 14, 18, 21, 23, 25, 27, and 29, respectively.

[TG/DTA Measurement Under Ordinary Pressure]

The compounds shown in Examples 1 to 8 and Comparative Examples 1 to 3 were each measured for TG/DTA. The measurement was performed by using "EXSTAR6000" (trade name; product of Seiko Instruments Inc.) at a heating rate of 10° C./min under ordinary pressure in a range of from 30° C. to 500° C. under $N_2$ flow (flow rate: 200 ml/min). With regards to a change in heat quantity upon starting of decomposition, an apparent change in heat quantity in a range of a weight loss of 1 mass % or greater was read out. In particular, the DTA curve within a range of weight loss of from 1 to 5 mass % showed an increase with respect to the base line, it was read as an exothermic change and when the curve showed a decrease, it was read as an endothermic change.

The TG/DTA curves of Compounds (1)-1, (1)-2, (1)-3, (1)-4, (2), (3), (4), (5), (1)-5, (1)-6, (1)-7, and (6) under ordinary pressure are shown in FIGS. 3, 6, 8, 10, 13, 15, 19, 22, 24, 26, 28, and 30, respectively.

Figure 3:
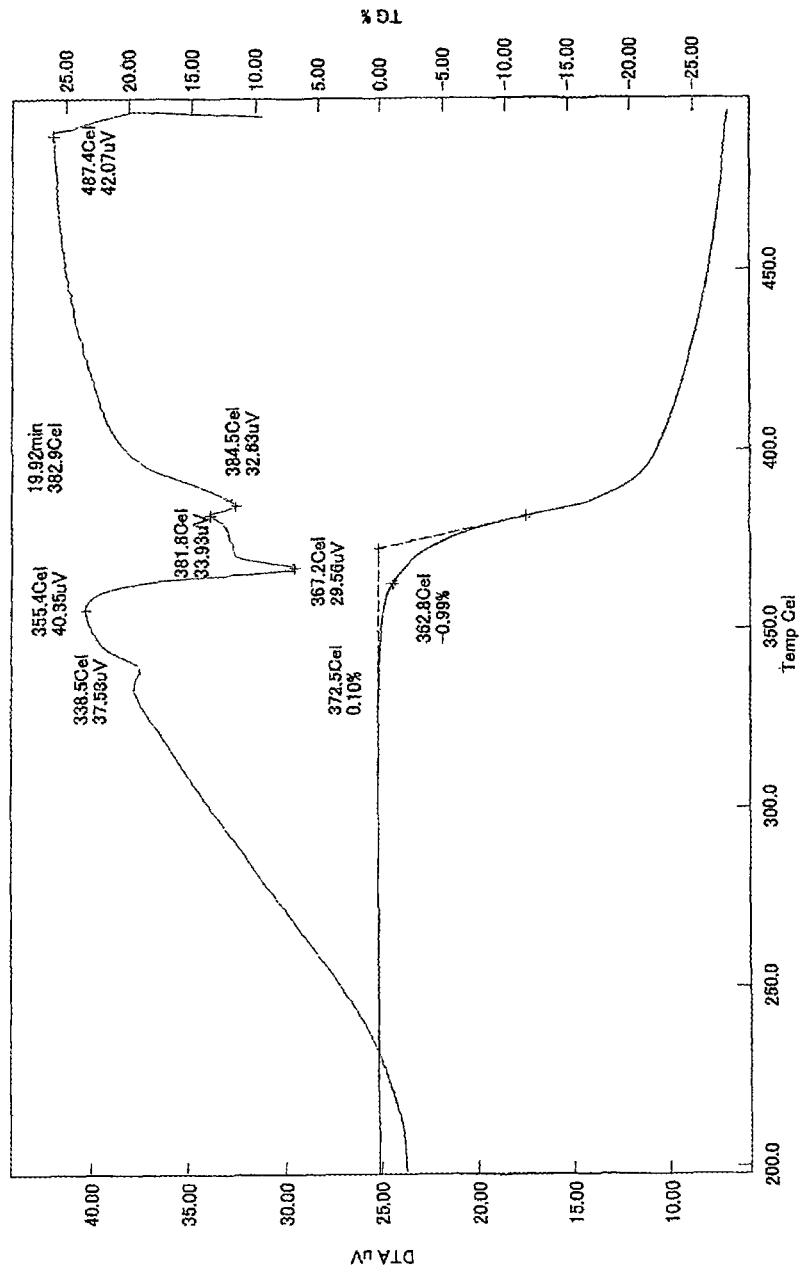
FIG. 3 shows a TG/DTA curve of Compound (1)-1 under ordinary pressure.

From the TG/DTA curve of Compound (1)-1 under ordinary pressure which was shown in FIG. 3, an endothermic change was observed at around 340° C. at which a weight loss started.

Figure 6:
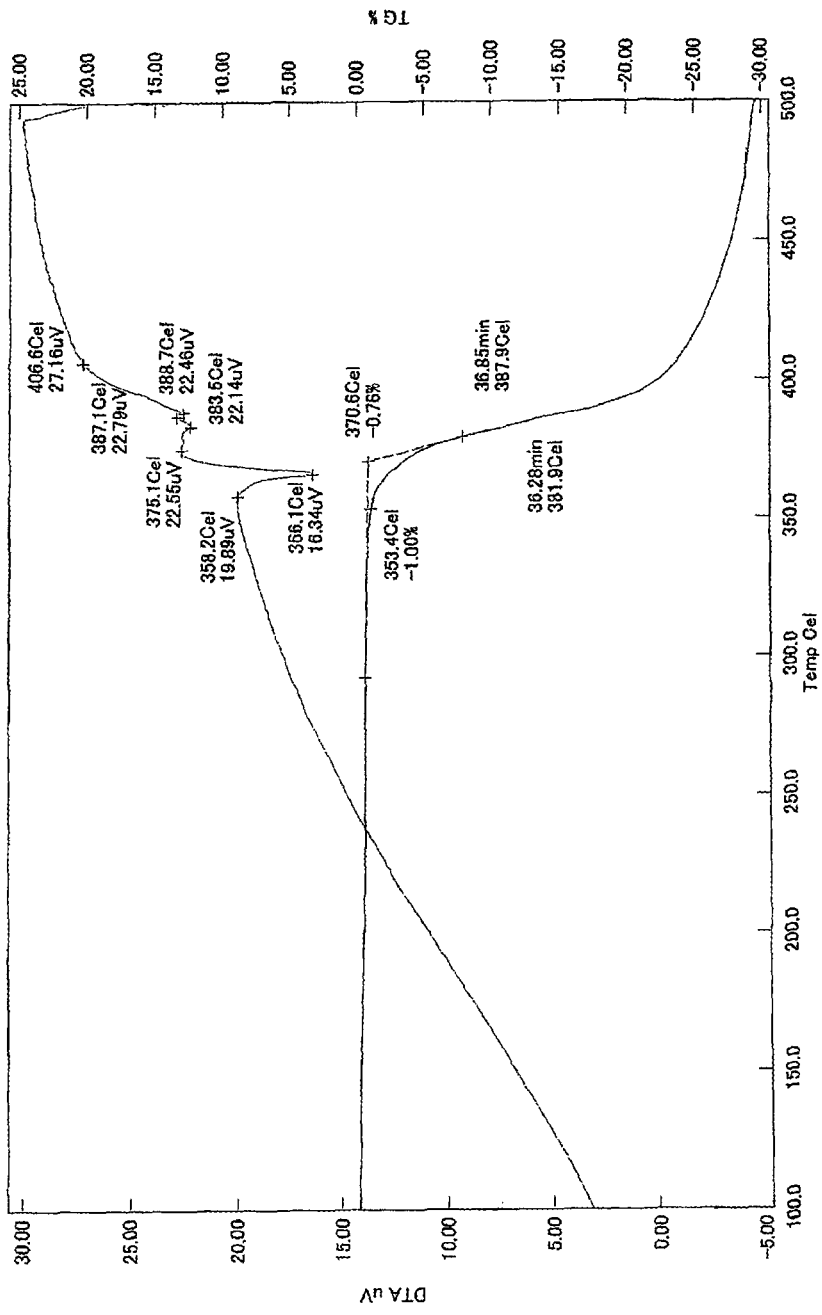
FIG. 6 shows a TG/DTA curve of Compound (1)-2 under ordinary pressure.
Figure 7:
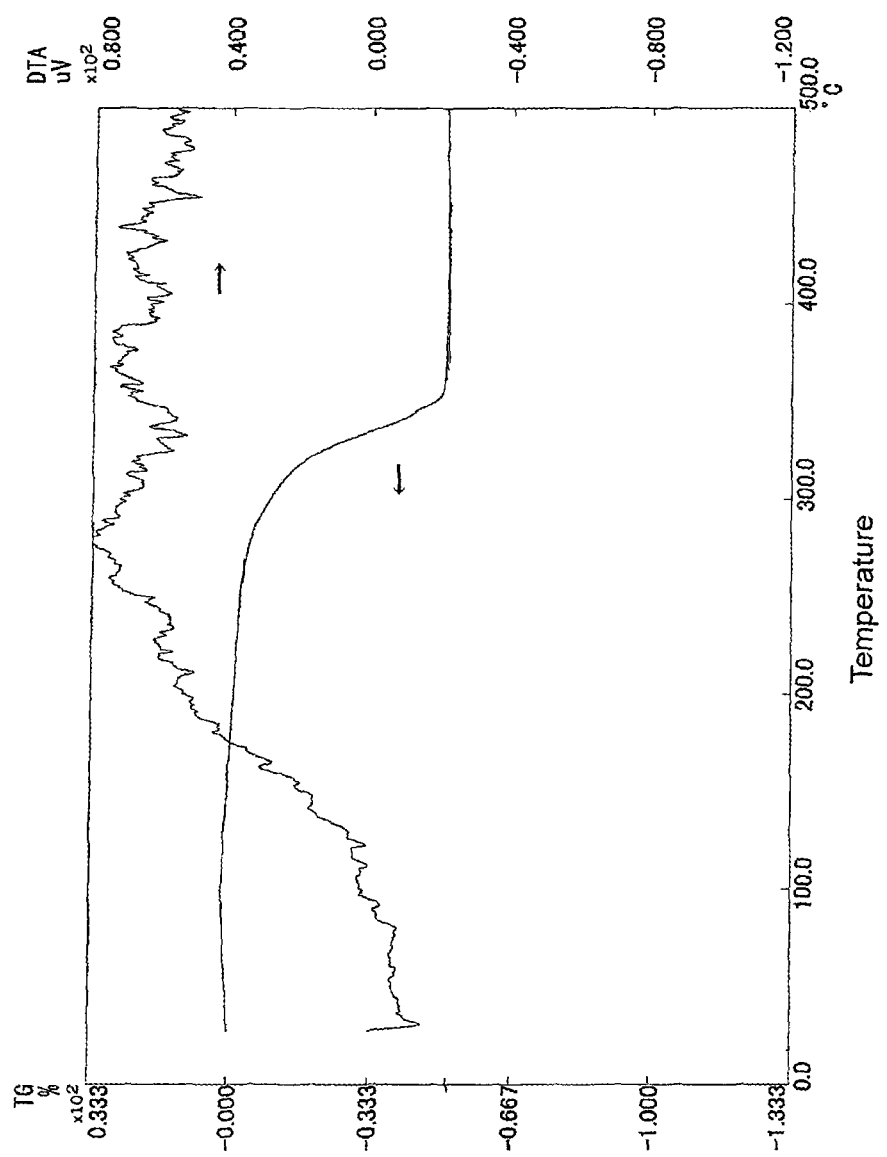
FIG. 7 shows a TG/DTA curve of Compound (1)-3 under vacuum.

From the TG/DTA curve of Compound (1)-2 under ordinary pressure which was shown in FIG. 6, an endothermic change was observed at around 350° C. at which a weight loss started.

Figure 8:
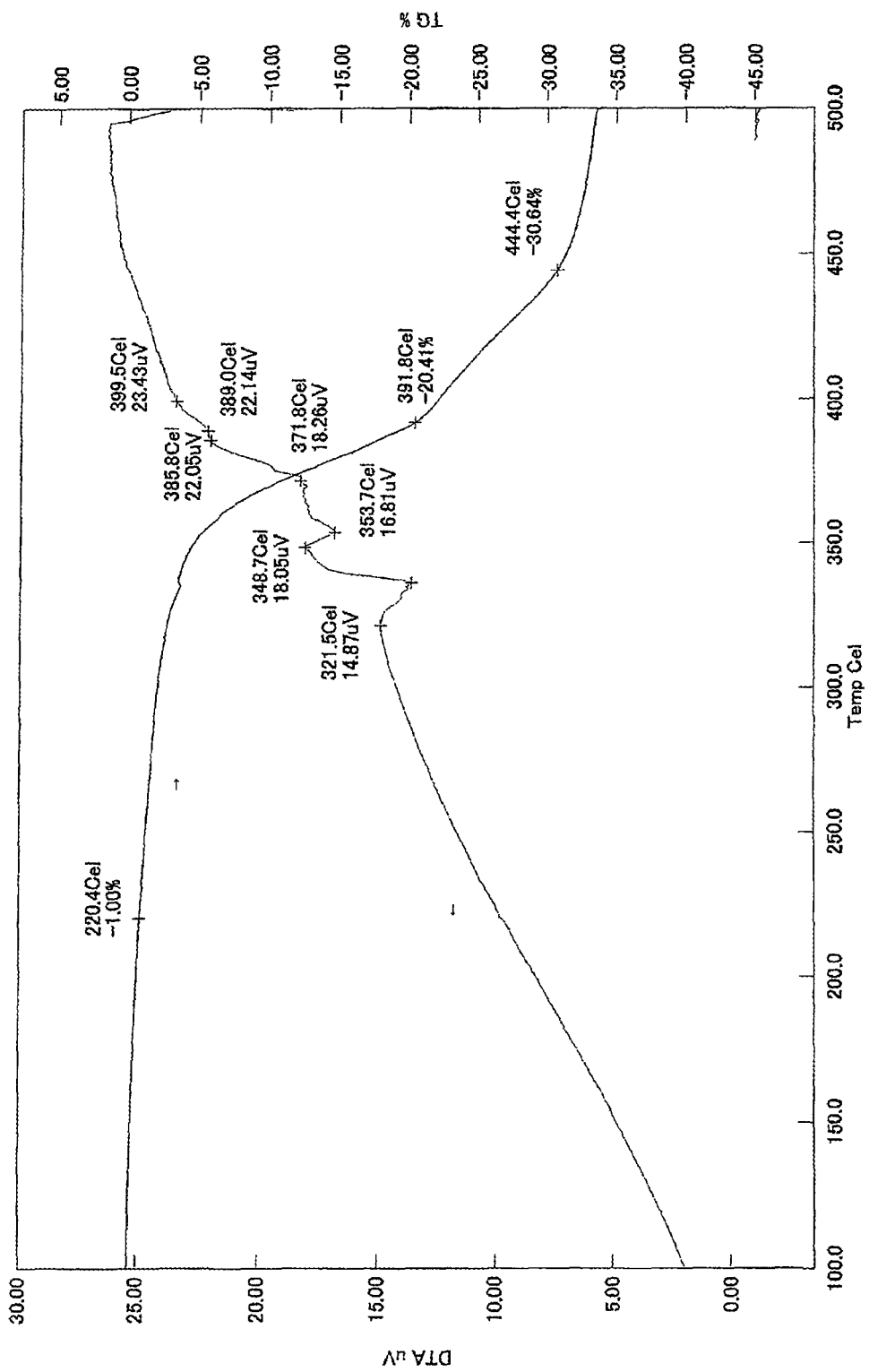
FIG. 8 shows a TG/DTA curve of Compound (1)-3 under ordinary pressure.
Figure 9:
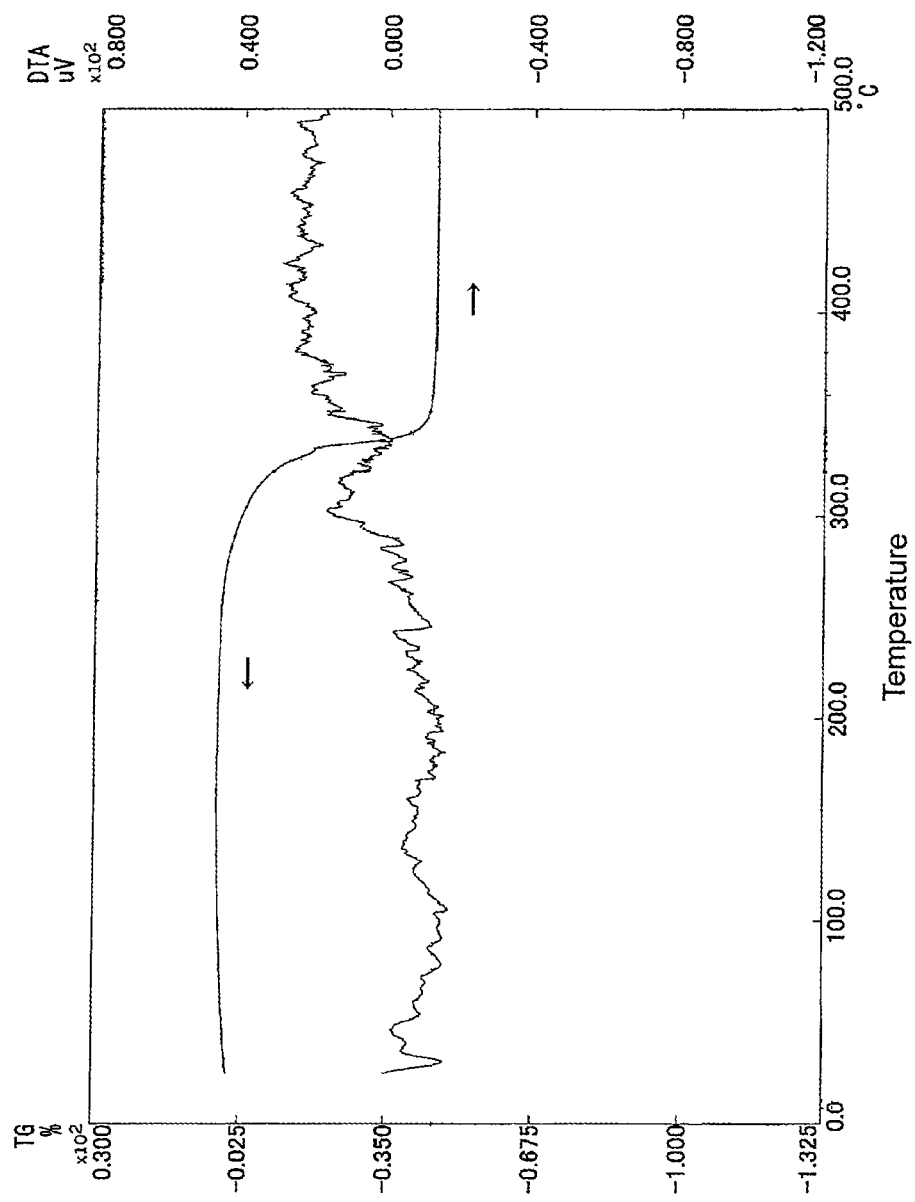
FIG. 9 shows a TG/DTA curve of Compound (1)-4 under vacuum.

From the TG/DTA curve of Compound (1)-3 under ordinary pressure which was shown in FIG. 8, an endothermic change was observed in a temperature range of from 200 to 350° C. in which a weight loss occurred.

Figure 10:
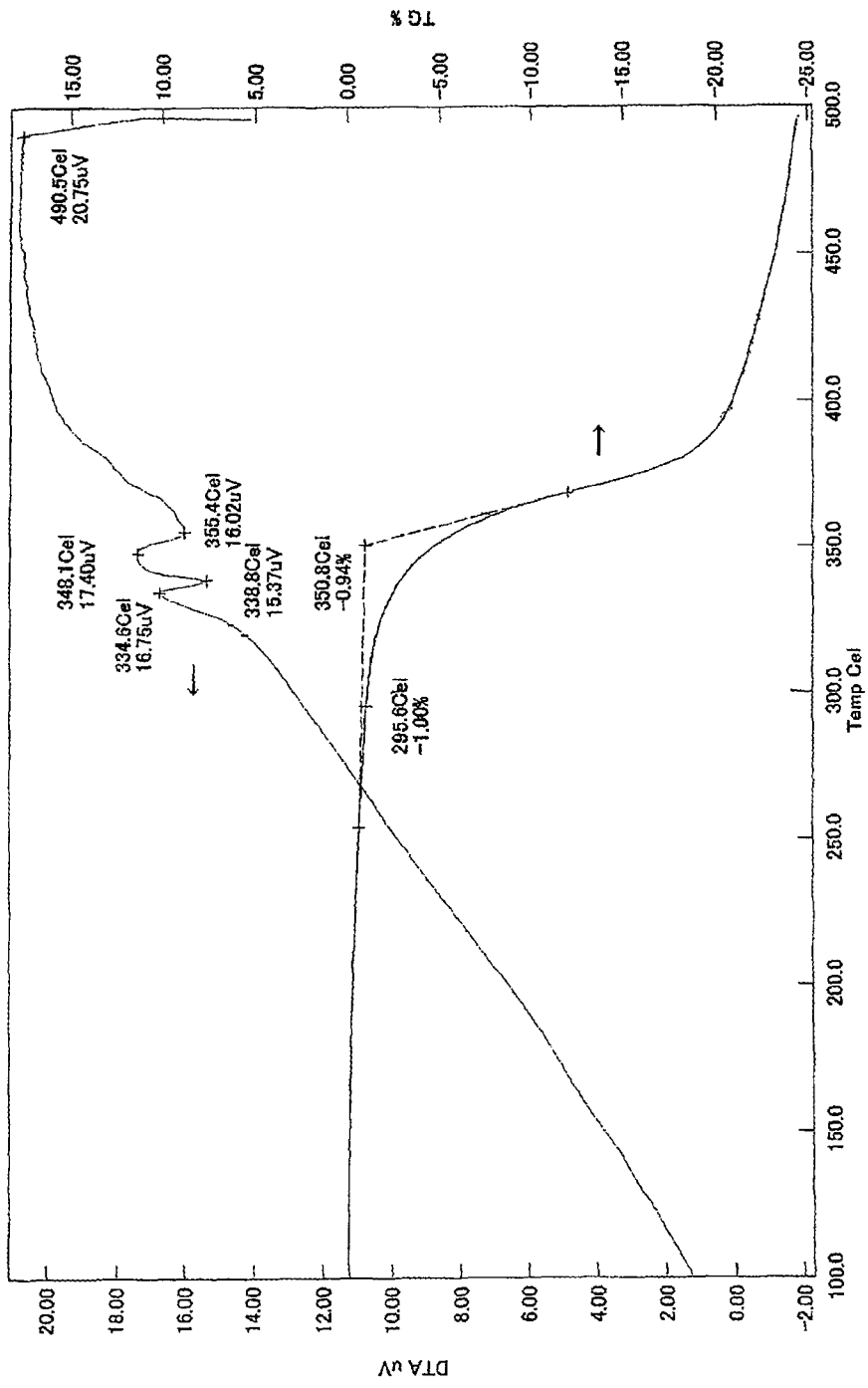
FIG. 10 shows a TG/DTA curve of Compound (1)-4 under ordinary pressure.

From the TG/DTA curve of Compound (1)-4 under ordinary pressure which was shown in FIG. 10, an exothermic change was observed at around 300° C. at which a weight loss started.

Figure 13:
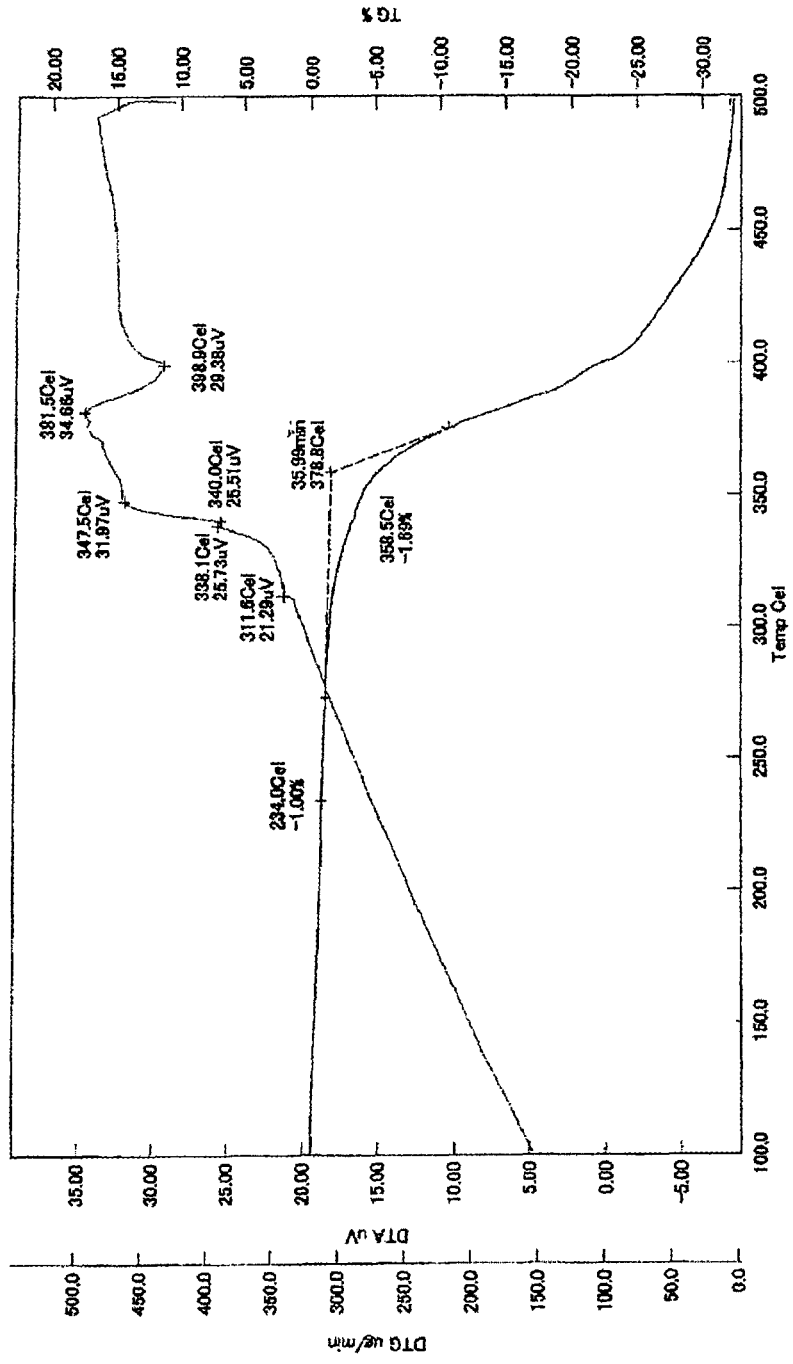
FIG. 13 shows a TG/DTA curve of Compound (2) under ordinary pressure.
Figure 14:
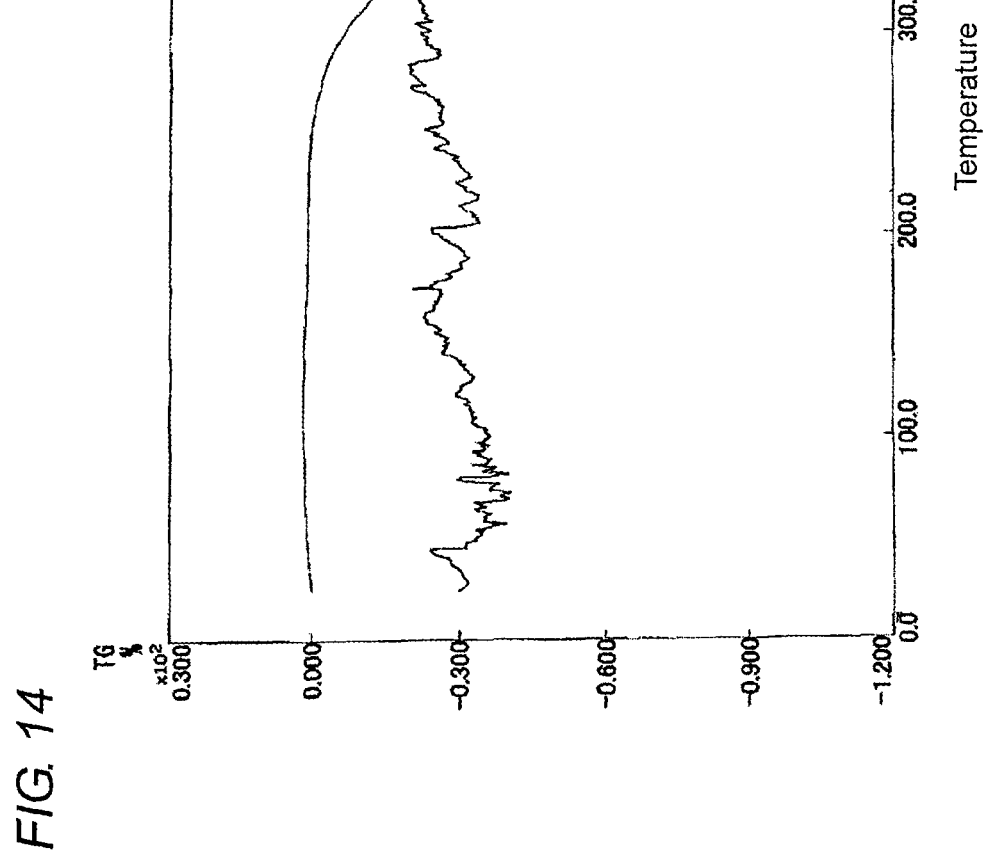
FIG. 14 shows a TG/DTA curve of Compound (3) under vacuum.

From the TG/DTA curve of Compound (2) under ordinary pressure which was shown in FIG. 13, a slight exothermic change was observed at around 300° C. at which a weight loss started.

Figure 15:
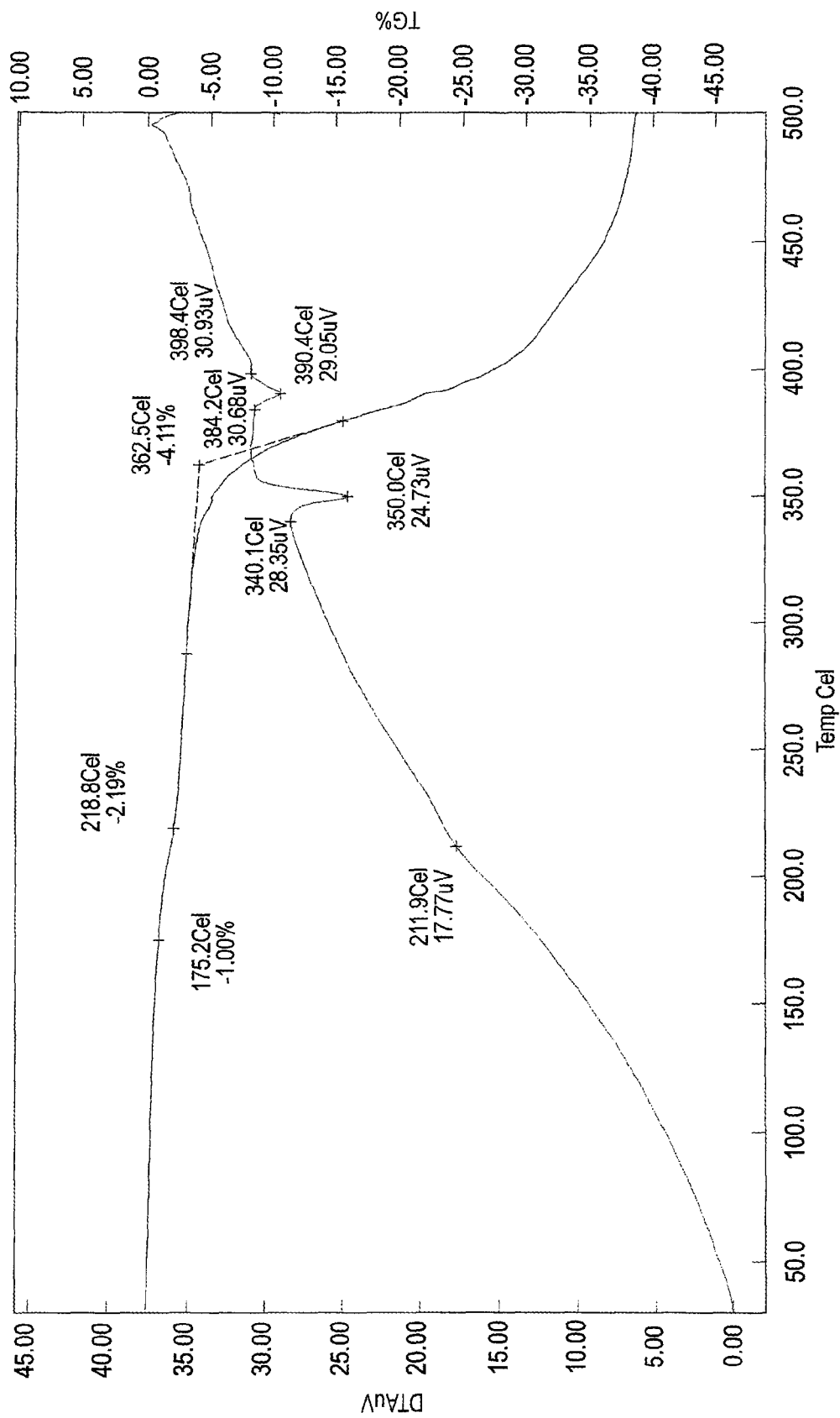
FIG. 15 shows a TG/DTA curve of Compound (3) under ordinary pressure.

From the TG/DTA curve of Compound (3) under ordinary pressure shown in FIG. 15, an exothermic change was observed at around 200° C. at which a weight loss started.

Figure 19:
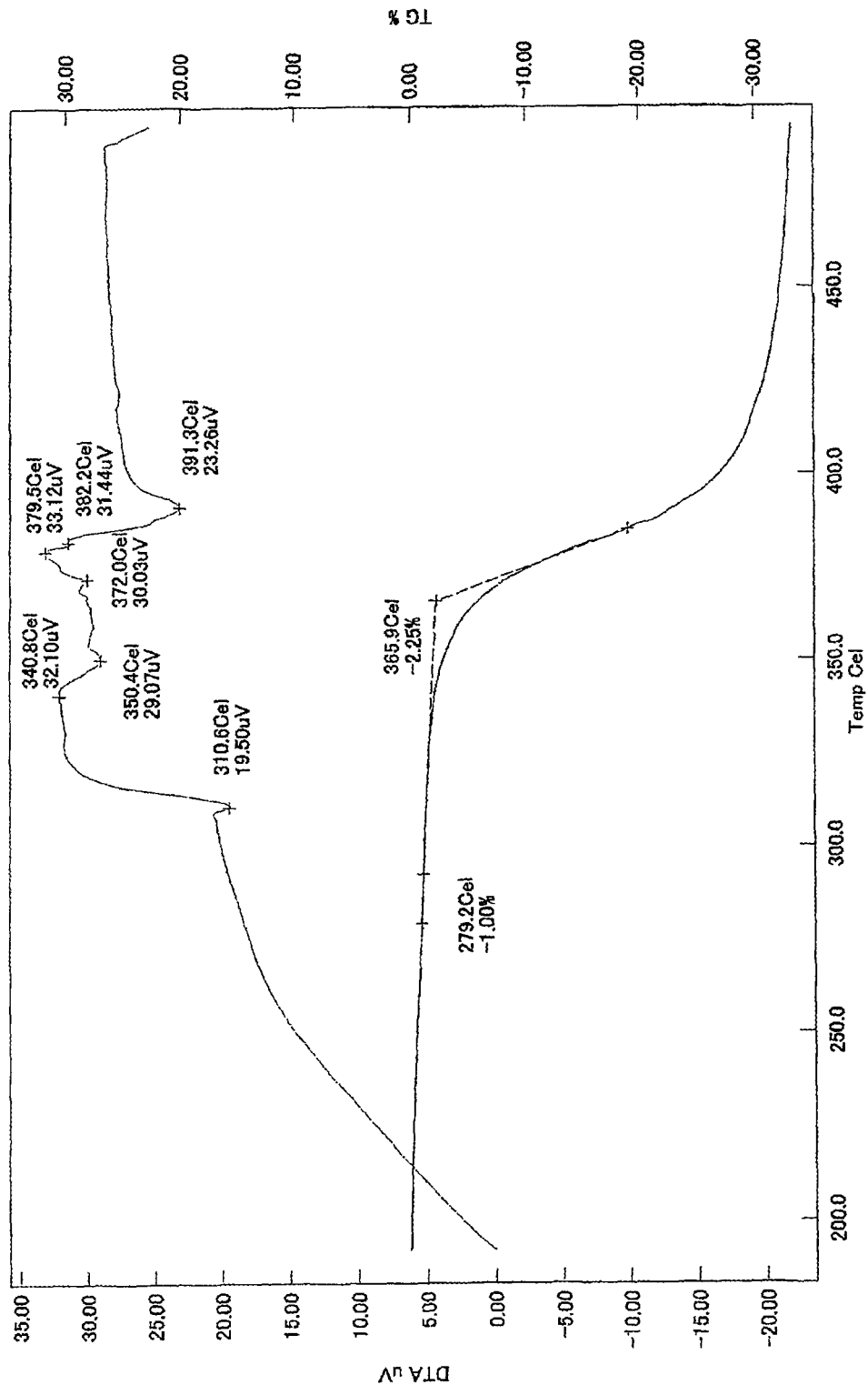
FIG. 19 shows a TG/DTA curve of Compound (4) under ordinary pressure.

From the TG/DTA curve of Compound (4) under ordinary pressure which was shown in FIG. 19, a gradual exothermic behavior was observed in a temperature range of from 250 to 300° C. in which a weight loss started.

Figure 22:
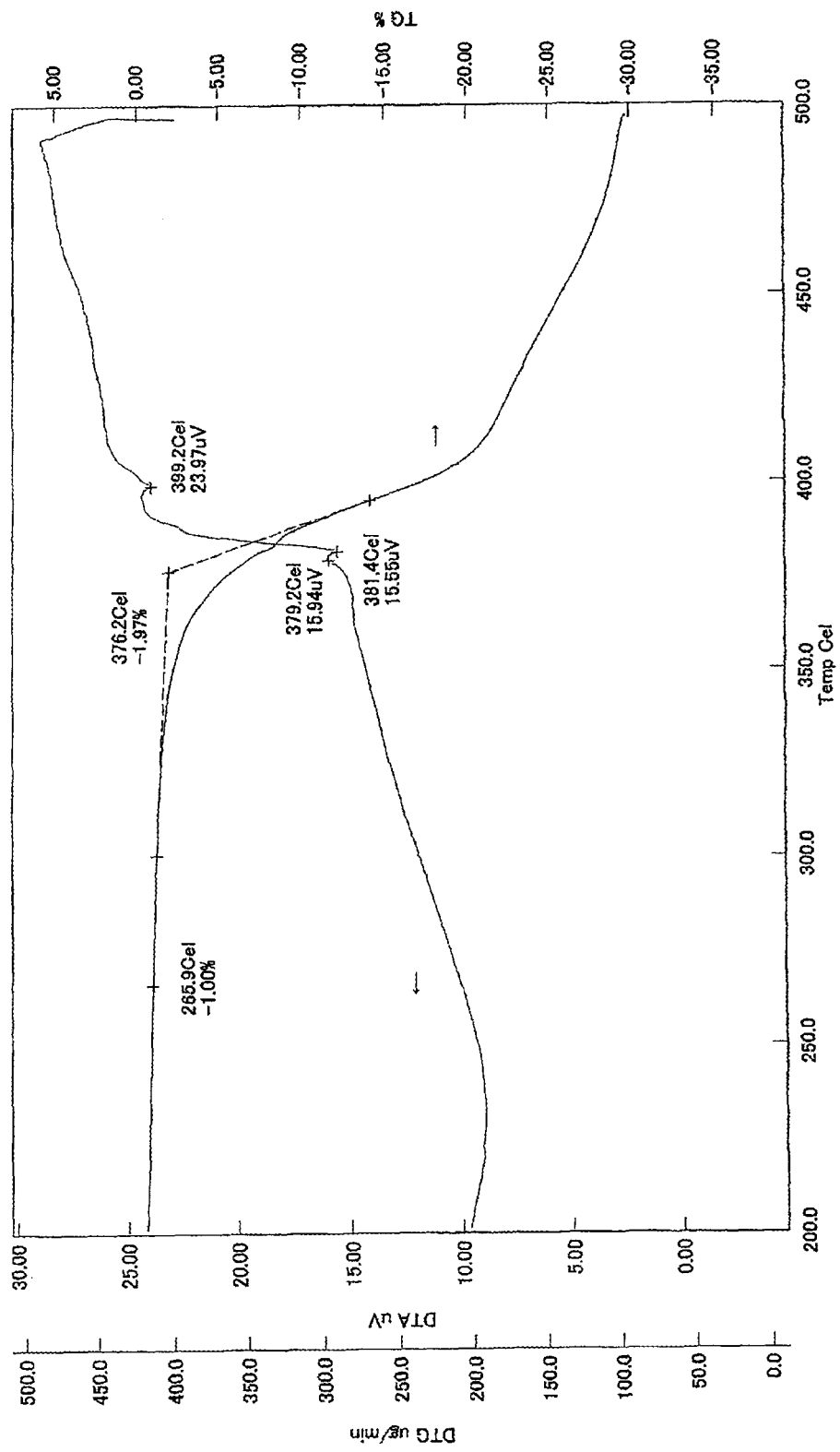
FIG. 22 shows a TG/DTA curve of Compound (5) under ordinary pressure.
Figure 23:
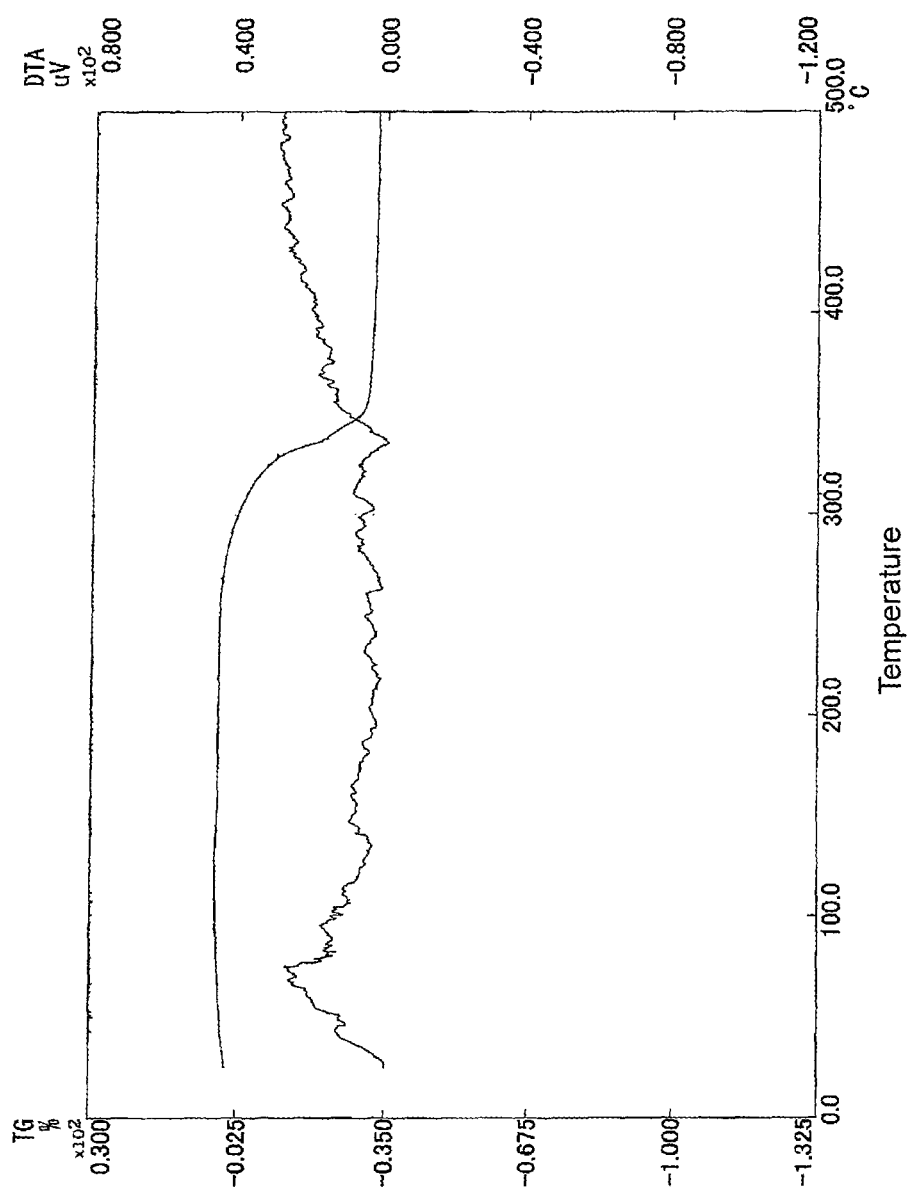
FIG. 23 shows a TG/DTA curve of Compound (1)-5 under vacuum.

From the TG/DTA curve of Compound (5) under ordinary pressure which was shown in FIG. 22, an exothermic change was observed until a weight loss reached 5 mass % occurred.

Figure 24:
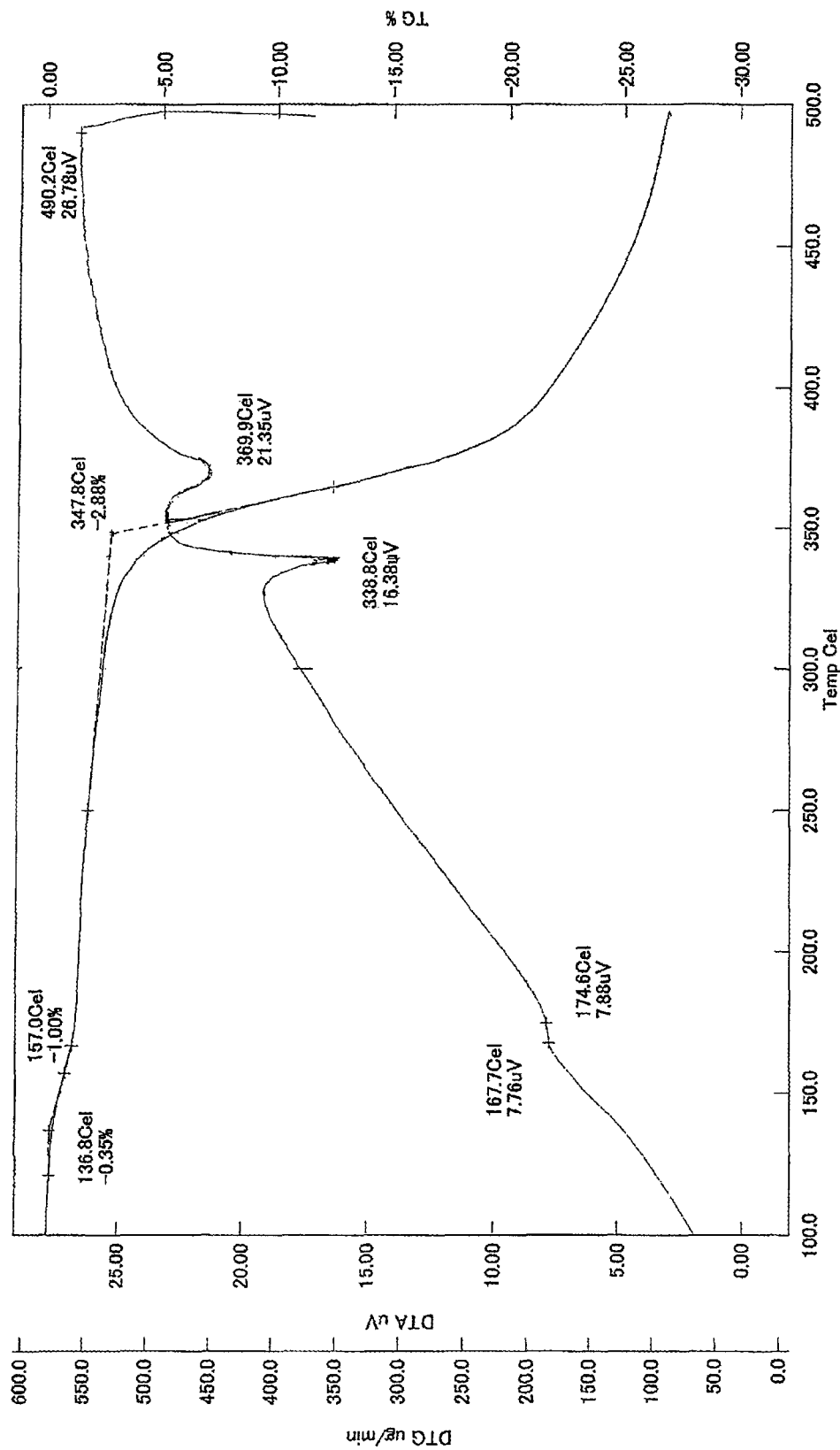
FIG. 24 shows a TG/DTA curve of Compound (1)-5 under ordinary pressure.
Figure 25:
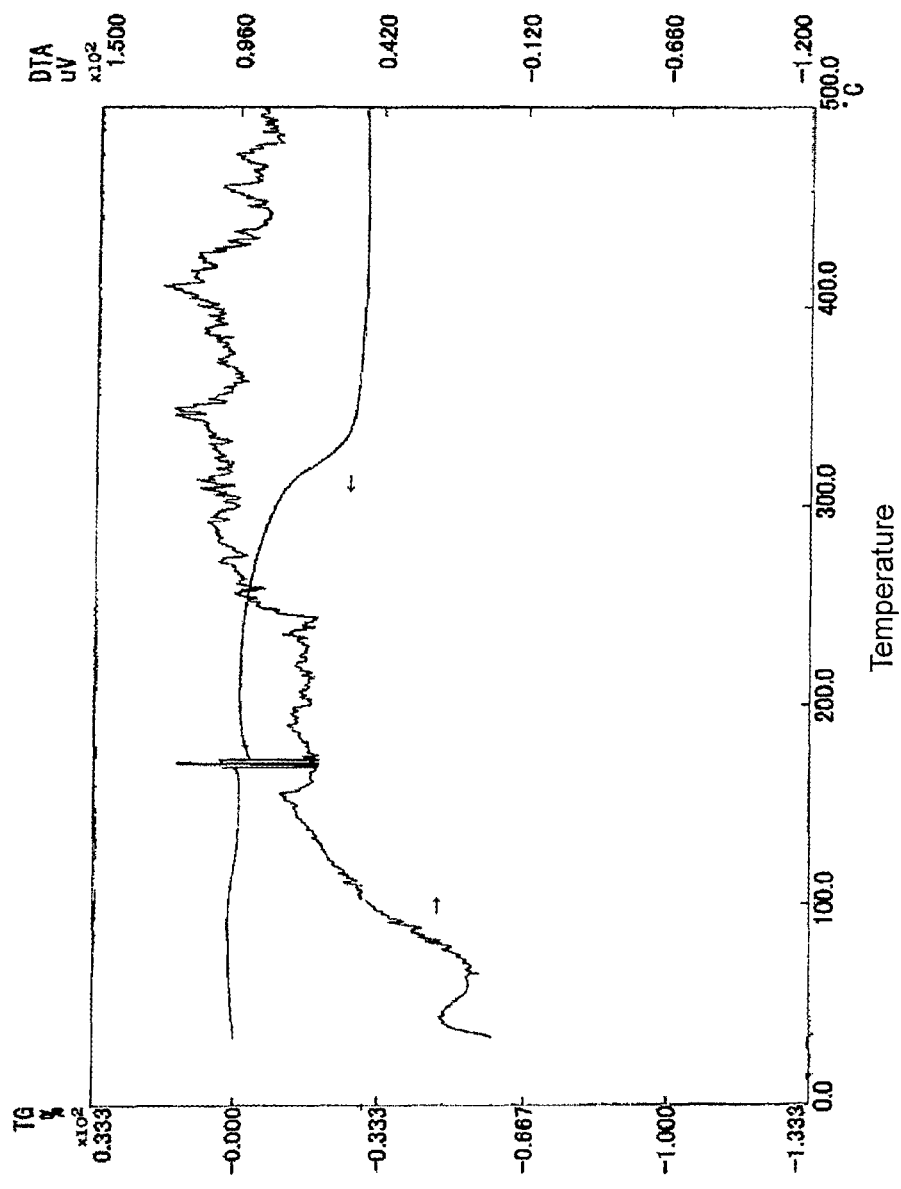
FIG. 25 shows a TG/DTA curve of Compound (1)-6 under vacuum.

From the TG/DTA curve of Compound (1)-5 under ordinary pressure which was shown in FIG. 24, an exothermic change was observed at around 150° C. at which a weight loss started.

Figure 26:
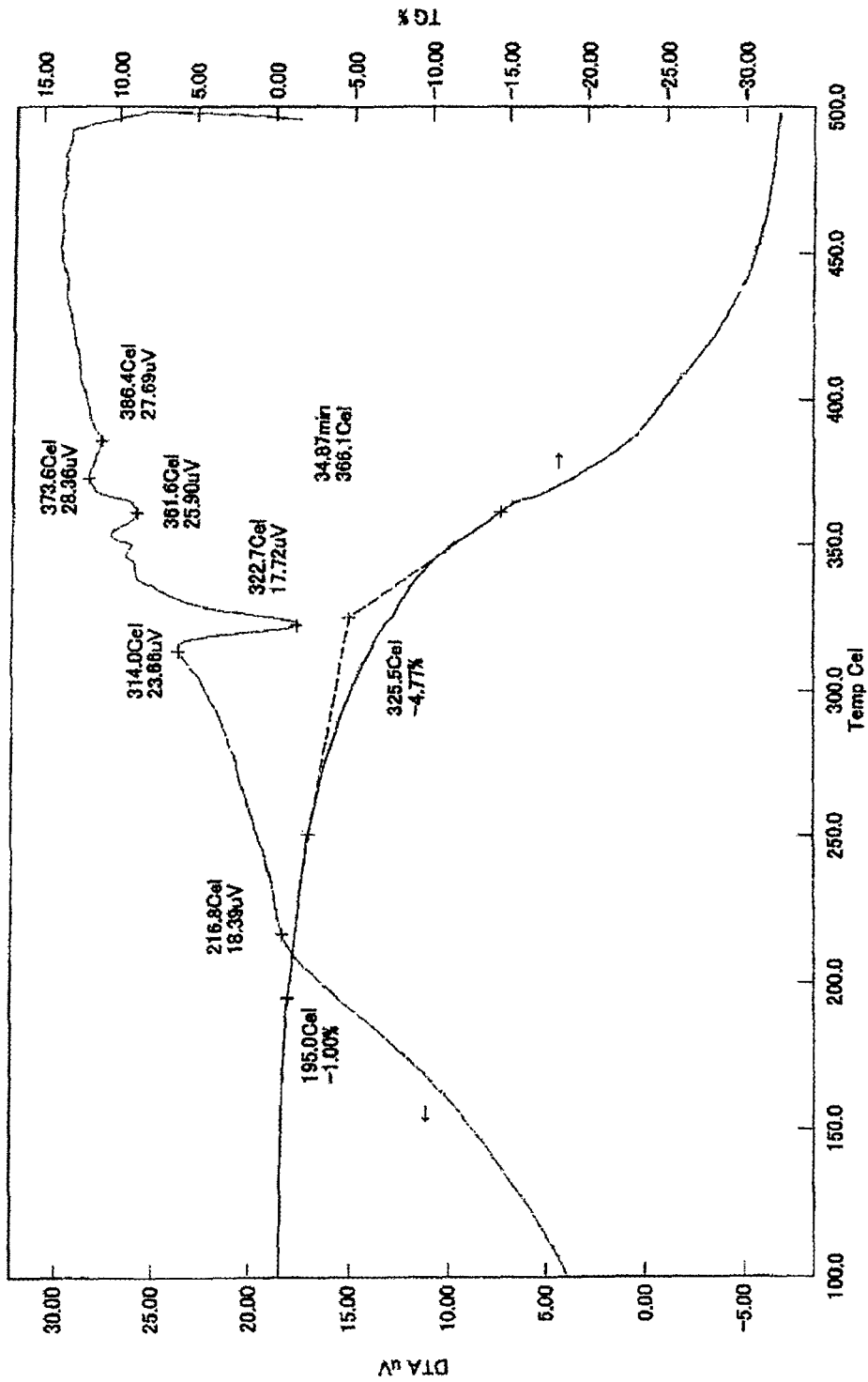
FIG. 26 shows a TG/DTA curve of Compound (1)-6 under ordinary pressure.
Figure 27:
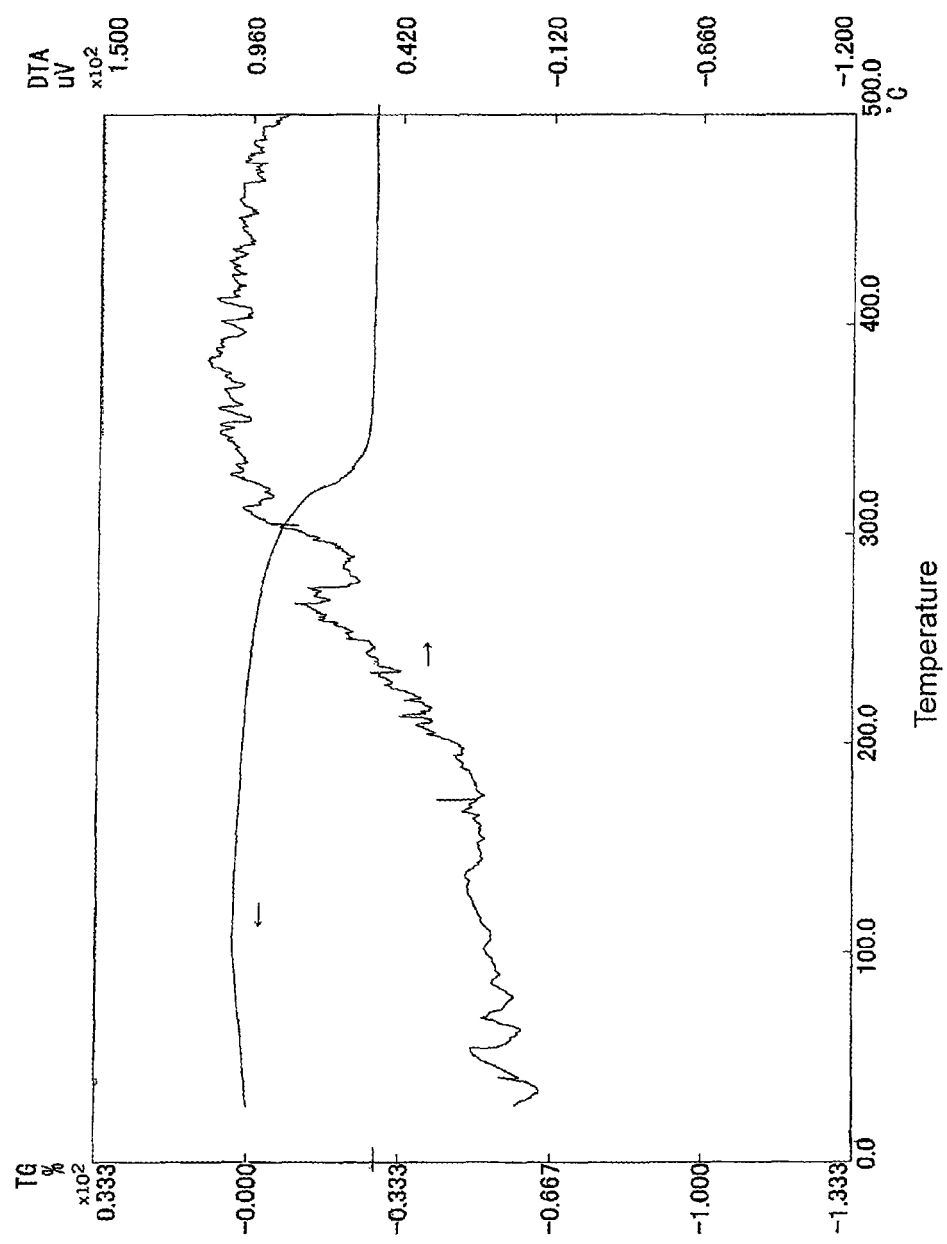
FIG. 27 shows a TG/DTA curve of Compound (1)-7 under vacuum.

From the TG/DTA curve of Compound (1)-6 under ordinary pressure shown in FIG. 26, an exothermic change was observed at around 200° C. at which a weight loss started.

Figure 28:
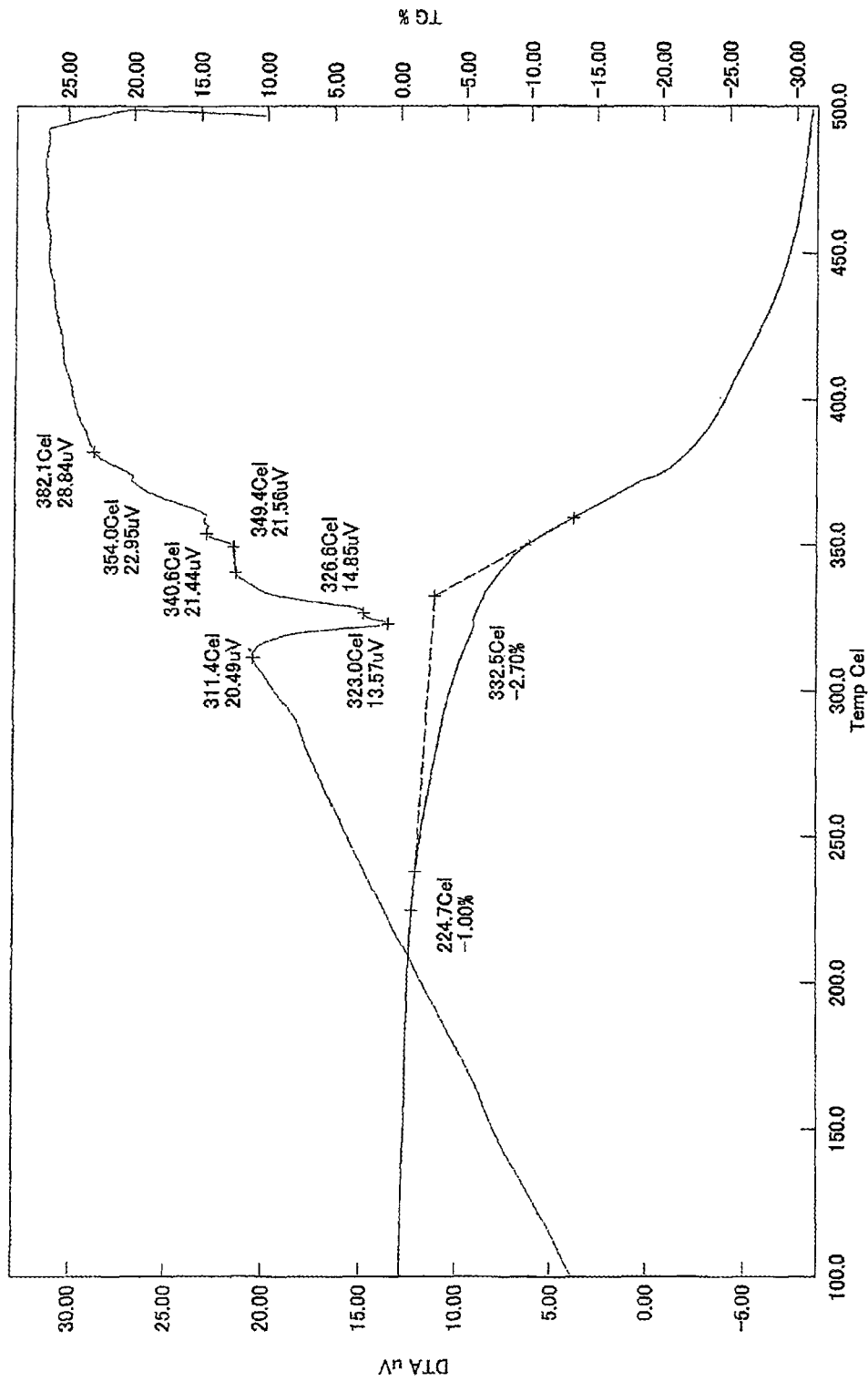
FIG. 28 shows a TG/DTA curve of Compound (1)-7 under ordinary pressure.
Figure 29:
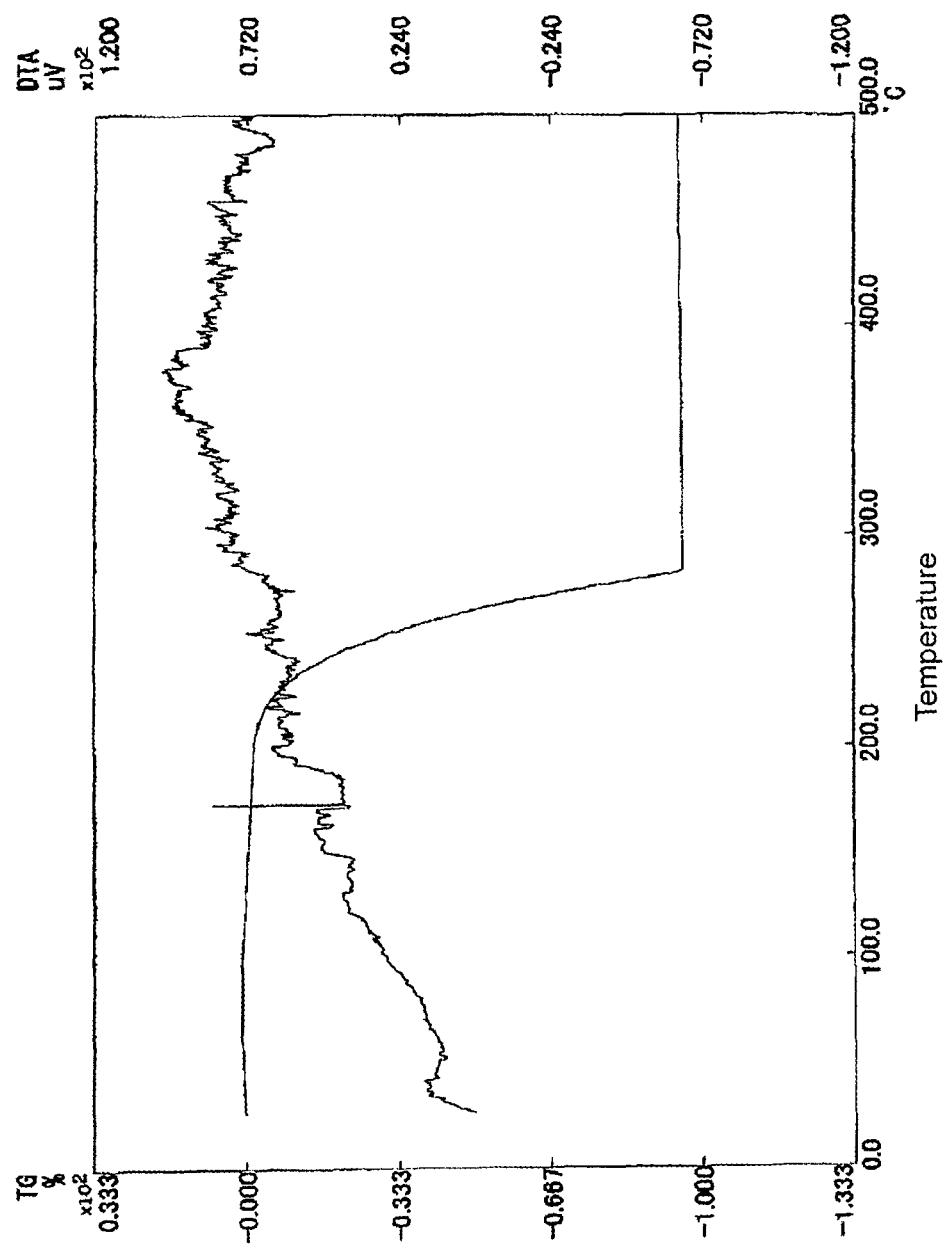
FIG. 29 shows a TG/DTA curve of Compound (6) under vacuum.
Figure 30:
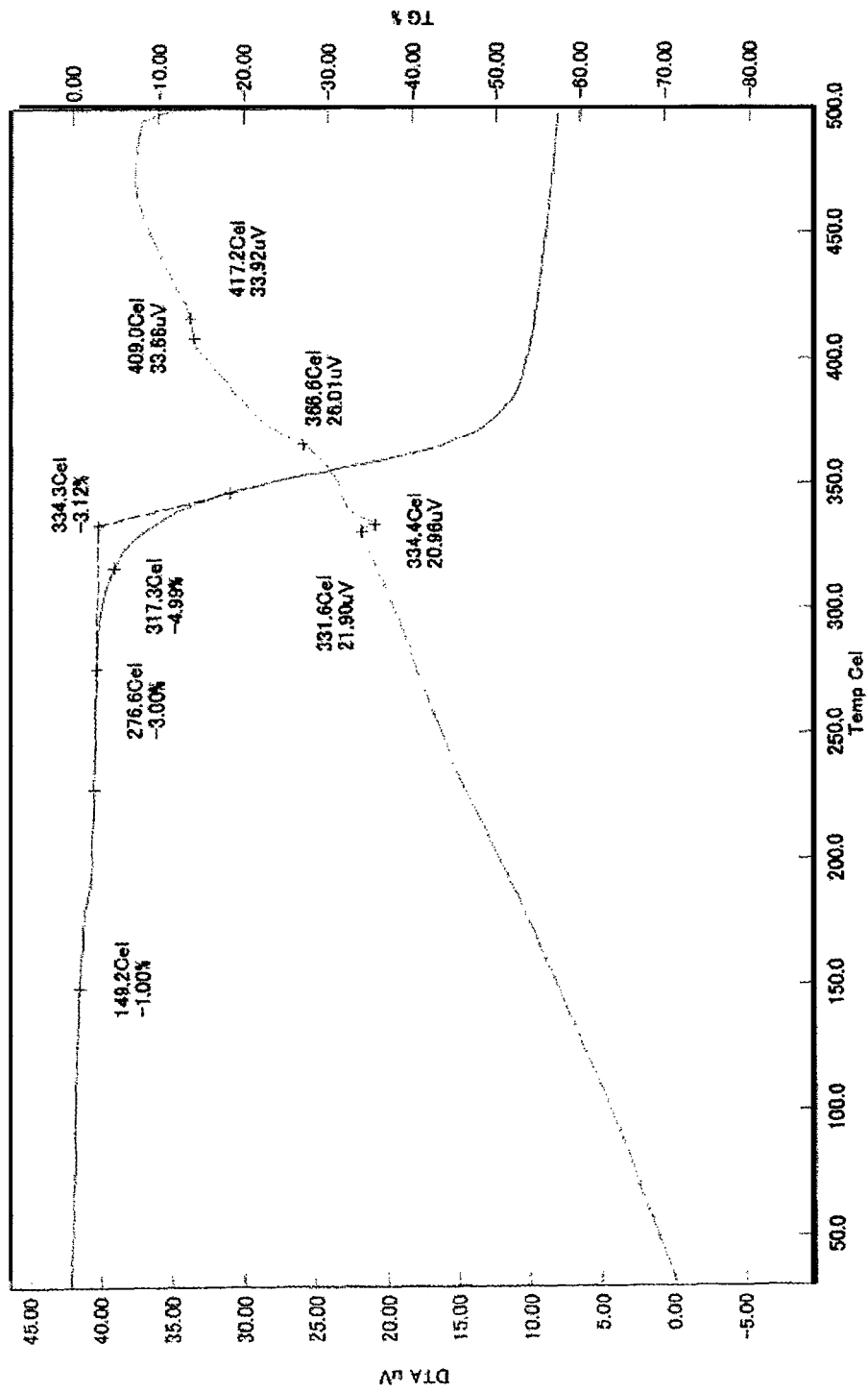
FIG. 30 shows a TG/DTA curve of Compound (6) under ordinary pressure.

From the TG/DTA curve of Compound (1)-7 under ordinary pressure which was shown in FIG. 28, a slight exothermic change was observed in a temperature range of from 300 to 310° C. at around a weight loss of 5 mass %.

[Measurement of Sublimation Purification Yield]

As described above, sublimation purification was performed by using "TRS-1" (trade name; product of ULVAC-RIKO, Inc). The sublimation purification was performed by reducing the pressure to $7.0 \times 10^{-2}$ Pa and increasing the temperature to 310 to 330° C. Red crystals attached to the glass tube were collected by using a spatula. The following are Compounds (1) to (6). Compounds (1)-1 to (1)-7 have a structure similar to that of Compound (1).

(1)

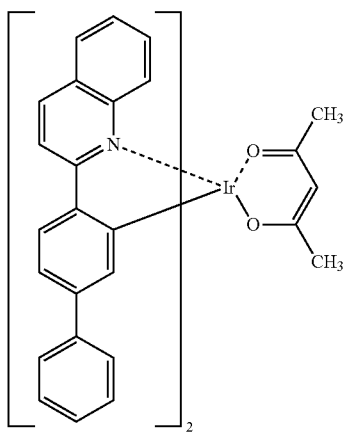

(TM-26)

(2)

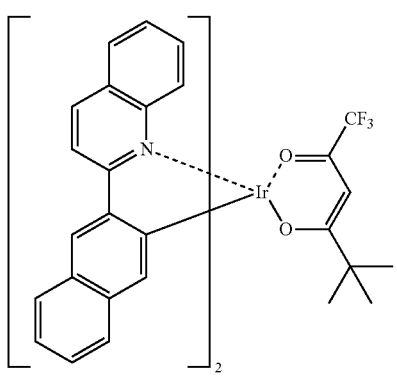

(TM-32)

(3)

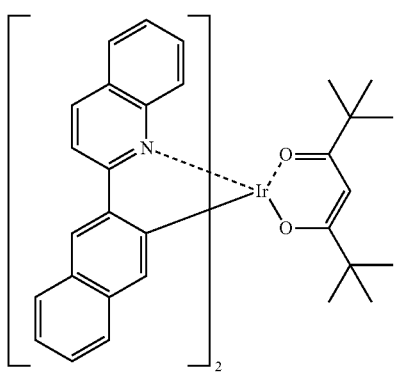

(TM-31)

(4)

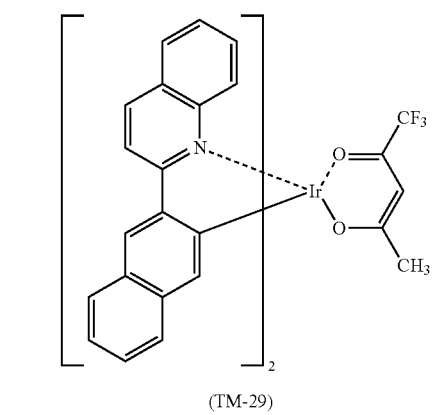

(TM-29)

(5)

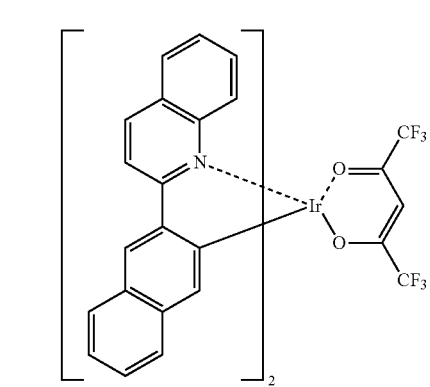

(TM-30)

(6)

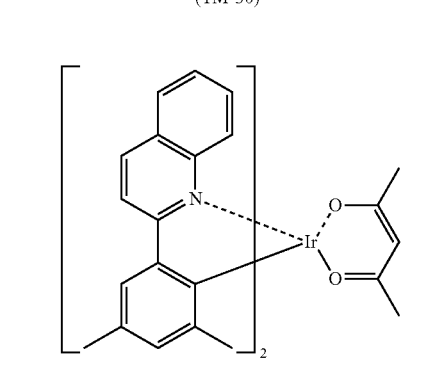

(TM-27)

TABLE 1

| Example | Compound | Rate of weight loss (%) after vacuum TG measurement | Thermal change at around weight-loss starting temperature upon ordinary pressure TG/DTA measurement | Sublimation purification yield (%) [Note 1] |
|---------|----------|-----|--------------------|---|
| Ex. 1 | Compound (1)-1 | 95 | Endothermic change | A |
| Ex. 2 | Compound (1)-2 | 83 | Endothermic change | A |
| Ex. 3 | Compound (1)-3 | 48 | Endothermic change | A |
| Ex. 4 | Compound (2) | 69 | Exothermic change | B |
| Ex. 5 | Compound (3) | 66 | Exothermic change | B |
| Ex. 6 | Compound (4) | 91 | Exothermic change | B |
| Ex. 7 | Compound (5) | 87 | Exothermic change | B |

TABLE 1-continued

| Example | Compound | Rate of weight loss (%) after vacuum TG measurement | Thermal change at around weight-loss starting temperature upon ordinary pressure TG/DTA measurement | Sublimation purification yield (%)[Note 1] |
|---|---|---|---|---|
| Ex. 8 | Compound (1)-4 | 46 | Exothermic change | C |
| Ex. 9 | Compound (6) | 94 | Endothermic change | A |
| Comp. Ex. 1 | Compound (1)-5 | 33 | Exothermic change | D |
| Comp. Ex. 2 | Compound (1)-6 | 30 | Exothermic change | D |
| Comp. Ex. 3 | Compound (1)-7 | 21 | Exothermic change | D |

Note 1)
A: 60% or greater,
B: 40% or greater but less than 60%,
C: 20% or greater but less than 40%,
D: less than 20%

Each of the compounds showed a purity of 98% or greater in purity measurement using HPLC (detection wavelength: 254 nm). It has been found from Table 1 that a good sublimation purification yield is achieved when the rate of weight loss is 45% or greater after vacuum TG measurement. It has also been found that a rate of weight loss after vacuum TG measurement does not simply affect the sublimation purification yield but the sublimation purification yield becomes better when a thermal change around a weight-loss starting temperature (when a weight loss of 1 mass % or greater occurs) determined by ordinary pressure TG/DTA measurement is an endothermic change.

Industrial Applicability

According to the present invention, it is possible to manufacture organic electroluminescence devices at a low cost.

The present application claims foreign priority based on Japanese Patent Application Nos. JP2009-201160 and JP2009-223454, filed Aug. 31 and Sep. 28, 2009, respectively, the contents of which is incorporated herein by reference.

The invention claimed is:

1. A method for selecting an iridium complex represented by the following formula (1) comprising:
   selecting the iridium complex represented by the following formula (1) and having a rate of weight loss of 45% or greater when the iridium complex is heated to 500° C. at 2° C./min under a degree of vacuum of from $1 \times 10^{-3}$ Pa to $1 \times 10^{-1}$ Pa; and
   carrying out a sublimation purification of the iridium complex:

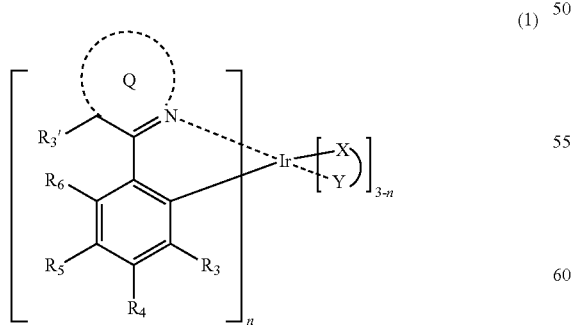

wherein
   each of $R_3$, $R_4$, $R_5$, $R_6$, and $R_3'$ independently represents a hydrogen atom an alkyl group, an alkenyl group, an alkynyl group, —CN, —$CF_3$, —$C_nF_{2n+1}$, a trifluorovinyl group, —$CO_2R$, —C(O)R, —$NR_2$, —$NO_2$, —OR, a halogen atom, an aryl group, or a heteroaryl group and may further have a substituent Z, wherein each of Rs independently represents a hydrogen atom, an alkyl group, an alkenyl group, an alkynyl group, a heteroalkyl group, an aryl group, or a heteroaryl group and may further have a substituent; each of Zs independently represents a halogen atom —R', —OR', —N(R')$_2$, —SR', —C(O)R', —C(O)OR', —C(O)N(R')$_2$—, —CN, —$NO_2$, —$SO_2$, —SOR', —$SO_2R'$, or —$SO_3R'$, each of R's independently represents a hydrogen atom, an alkyl group, a perhaloalkyl group, an alkenyl group, an alkynyl group, a heteroalkyl group, an aryl group, or a heteroaryl group;

$R_3'$ and $R_6$ may be linked to form a ring via a linking group selected from —$CR_2$—$CR_2$—, —CR=CR—, —$CR_2$—, O—, —NR—, —O—$CR_2$—, —NR—$CR_2$—, and —N=CR—, wherein each of Rs independently represents a hydrogen atom, an alkyl group, an alkenyl group, an alkynyl group, a heteroalkyl group, an aryl group or a heteroaryl group and may further have a substituent;

$R_3$ and $R_4$ may be coupled to each other to form a condensed four- to seven-membered ring and the condensed four- to seven-membered ring is a cycloalkane ring, cycloheteroalkane ring, aromatic hydrocarbon ring, or heteroaromatic ring and may further have a substituent, wherein cycloheteroalkane ring has 1-30 carbon atom and a nitrogen atom, an oxygen atom, or sulfur atom as a heteroatom, and wherein heteroaromatic ring is selected from the group consisting of imidazolyl, pyrazolyl, pyridyl, pyrazyl, pyrimidyl, triazinyl, quinolyl, isoquinolinyl, pyrrolyl, indolyl, furyl, thienyl, benzoxazolyl, benzimidazolyl, benzthiazolyl, carbazolyl, and azepinyl;

$R_4$ and $R_5$ may be coupled to each other to form a five- or six-membered ring, wherein the ring may further have a substituent;

the ring Q represents 6-membered heteroaryl ring having one nitrogen atom as heteroatom which is fused to a 6-membered aryl ring coordinated to iridium;

(X-Y) represents acetylacetonate or picolinate, or derivatives thereof; and n stands for an integer from 1 to 3.

2. The method according to claim 1, wherein when the iridium complex is heated at 10° C./min under ordinary pressure, the iridium complex shows an endothermic change as a thermal change in a range of a rate of weight loss of from 1 to 5 mass %.

3. The method according to claim 1, wherein the ring Q is condensed and at least one of $R_3$, $R_4$, $R_5$, and $R_6$ represents a methyl group or a phenyl group, with the proviso that when at least one of $R_3$, $R_4$, $R_5$, and $R_6$ represents a phenyl group, the phenyl group may further have a substituent or the phenyl group may be coupled to the ring Q via a single bond.

4. The method according to claim 1, wherein the iridium complex is represented by the following formula (T-4):

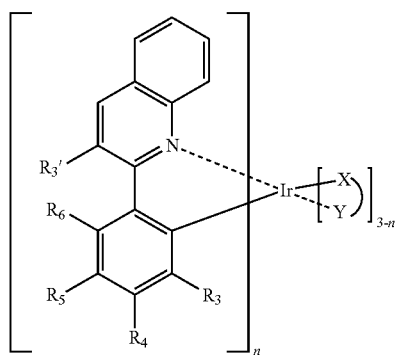

(T-4)

wherein $R_3{}'$ represents a hydrogen atom, an alkyl group, a heteroalkyl group, an aryl group, or a heteroaryl group and may further have a substituent Z;

each of $R_3$, $R_4$, $R_5$, and $R_6$ independently represents a hydrogen atom, an alkyl group, an alkenyl group, an alkynyl group, —CN, —CF$_3$, —C$_n$F$_{2n+1}$, a trifluorovinyl group, —CO$_2$R, —C(O)R, —NR$_2$, —NO$_2$, —OR, a halogen atom, an aryl group, or a heteroaryl group and may further have a substituent Z, wherein each of Rs independently represents a hydrogen atom, an alkyl group, an alkenyl group, an alkynyl group, a heteroalkyl group, an aryl group, or a heteroaryl group and may further have a substituent;

each of Zs independently represents a halogen atom, —R', —OR', —N(R')$_2$, —SR', —C(O)R', —C(O)OR', —C(O)N(R')$_2$—, —CN, —NO$_2$, —SO$_2$, —SOR', —SO$_2$R', or —SO$_3$R', each of R's independently represents a hydrogen atom, an alkyl group, a perhaloalkyl group, an alkenyl group, an alkynyl group, a heteroalkyl group, an aryl group, or a heteroaryl group;

$R_4$ and $R_5$ may be coupled to each other to form a five- or six-membered ring, wherein the ring may further have a substituent;

(X-Y) represents acetylacetonate or picolinate, or derivatives thereof; and n stands for an integer from 1 to 3.

5. The method according to claim 1, wherein the iridium complex is purified by column chromatography.

* * * * *